(12) United States Patent
Kim et al.

(10) Patent No.: US 7,604,874 B2
(45) Date of Patent: Oct. 20, 2009

(54) ORGANIC COMPOUNDS FOR ELECTROLUMINESCENCE AND ORGANIC ELECTROLUMINESCENT DEVICES USING THE SAME

(75) Inventors: Ji-Eun Kim, Jinhae (KR); Se-Hwan Son, Daejeon (KR); Jae-Soon Bae, Daejeon (KR); Youn-Gu Lee, Seoul (KR); Kong-Kyeum Kim, Daejeon (KR); Jae-Chol Lee, Daejeon (KR); Jun-Gi Jang, Daejeon (KR); Sung-Gap Im, Gunpo (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/585,909

(22) Filed: Oct. 25, 2006

(65) Prior Publication Data

US 2007/0037012 A1      Feb. 15, 2007

Related U.S. Application Data

(62) Division of application No. 10/431,349, filed on May 6, 2003, now Pat. No. 7,485,733.

(30) Foreign Application Priority Data

May 7, 2002    (KR) ............... 10-2002-0025084
Feb. 19, 2003  (KR) ............... 10-2003-0010439

(51) Int. Cl.
*C09K 11/06*    (2006.01)
(52) U.S. Cl. ............ 428/690; 428/917; 313/504; 313/506; 252/301.16; 252/500
(58) Field of Classification Search ............ 428/690, 428/917; 313/504, 506
See application file for complete search history.

(56) References Cited

U.S. PATENT DOCUMENTS

| 4,356,429 A | 10/1982 | Tang et al. |
| 4,720,432 A | 1/1988 | VanSlyke et al. |
| 4,736,032 A | 4/1988 | Fox et al. |

(Continued)

FOREIGN PATENT DOCUMENTS

EP    0 926 216 A1    6/1999

(Continued)

OTHER PUBLICATIONS

Hamada, et al. Organic light-emitting diodes using a gallium complex., Apr. 20, 1998, American Institute of Physics, vol. 72, No. 16.

(Continued)

*Primary Examiner*—D. Lawrence Tarazano
*Assistant Examiner*—Camie S Thompson
(74) *Attorney, Agent, or Firm*—McKenna Long Aldridge LLP

(57) ABSTRACT

Disclosed is a novel group of compounds having a general structure of anthracene body substituted with at least one thiophenyl group, which can be further substituted with various substituent groups. These new compounds are generally compatible with organic electroluminescence. Also disclosed are organic electroluminescent devices and method of making the same. The organic electroluminescent devices include at least one of the compounds in various layers thereof. Organic electroluminescent devices employing the new compounds in their light-emitting layers show outstanding stability.

44 Claims, 4 Drawing Sheets

U.S. PATENT DOCUMENTS

| | | | |
|---|---|---|---|
| 5,026,894 | A | 6/1991 | Tour et al. |
| 5,059,863 | A | 10/1991 | Tashiro et al. |
| 5,061,569 | A | 10/1991 | VanSlyke et al. |
| 5,227,252 | A | 7/1993 | Murayama et al. |
| 5,256,945 | A | 10/1993 | Imai et al. |
| 5,432,014 | A | 7/1995 | Sano et al. |
| 5,516,577 | A | 5/1996 | Matsuura et al. |
| 5,540,999 | A | 7/1996 | Yamamoto et al. |
| 5,609,970 | A | 3/1997 | Kolb et al. |
| 5,811,833 | A | 9/1998 | Thompson |
| 5,817,431 | A | 10/1998 | Shi et al. |
| 5,840,217 | A | 11/1998 | Lupo et al. |
| 5,998,803 | A | 12/1999 | Forrest et al. |
| 6,020,078 | A | 2/2000 | Chen et al. |
| 6,074,734 | A | 6/2000 | Kawamura et al. |
| 6,312,836 | B1 | 11/2001 | Bulovic et al. |
| 6,355,365 | B1 | 3/2002 | Hotta et al. |
| 6,361,886 | B2 | 3/2002 | Shi et al. |
| 6,383,666 | B1 | 5/2002 | Kim et al. |
| 6,458,475 | B1 | 10/2002 | Adachi et al. |
| 2002/0048687 | A1 | 4/2002 | Hosokawa et al. |
| 2002/0048887 | A1 | 4/2002 | Hwang et al. |

FOREIGN PATENT DOCUMENTS

| | | |
|---|---|---|
| EP | 1-087-066 | 3/2001 |
| EP | 1 182 183 A1 | 2/2002 |
| EP | 1 645 552 A1 | 4/2006 |
| JP | 05-202356 | 8/1993 |
| JP | 06-240243 | 8/1994 |
| JP | 06-306357 | 11/1994 |
| JP | 6-306357 | 11/1994 |
| JP | 07-166160 | 6/1995 |
| JP | 1996-269445 | 10/1996 |
| JP | 09-199276 | 7/1997 |
| JP | 1998-017860 | 1/1998 |
| JP | 11-067449 | 3/1999 |
| JP | 11-111460 | 4/1999 |
| JP | 11-219788 | 8/1999 |
| JP | 11-233263 | 8/1999 |
| JP | 00-058267 | 2/2000 |
| JP | 2000-053676 | 2/2000 |
| JP | 06-009952 | 3/2000 |
| JP | 2000-182772 | 6/2000 |
| JP | 2000-515926 | 11/2000 |
| JP | 2001-076879 | 3/2001 |
| JP | 2001-123157 | 5/2001 |
| JP | 2002-059676 | 2/2002 |
| JP | 2002-060742 | 2/2002 |
| JP | 3971310 B1 | 6/2007 |
| WO | WO 00/58315 | 10/2000 |
| WO | WO 01/72673 A1 | 10/2001 |
| WO | WO 02/088274 A1 | 11/2002 |

OTHER PUBLICATIONS

Murata, et al. Organic light-emitting devices with saturated red emission using 6, 13-dephenylpentacene., Apr. 16, 2001, American Institute of Physics, vol. 78, No. 16.

Shi, et al. Doped organic electroluminescent devices with improved stability., Mar. 31 1997, American Institute of Physics, vol. 70, No. 13.

Adachi, et al., High-efficiency organic electrophosphorescent devices with tris (2-phenypyridine) iridium doped into electron-transporting materials., Aug. 7, 2000, American Institute of Physics, vol. 77, No. 6.

Adachi, et al. High efficiency red electrophosphorescence devices., Mar. 12, 2001, American Institute of Physics, vol. 78, No. 11.

Burrows et al. Operating lifetime of phosphorescent organic light emitting., May 1, 2000, American Institute of Physics., vol. 76, No. 18.

Baldo et al. Very high-efficiency green organic light-emitting devices based on electrophosphorescene., Jul. 5, 1999, American Institute of Physics., vol. 75, No. 1.

Baldo, et al. Improved energy transfer in electrophosphorescent devices., Jan. 18, 1999, American Institute of Physics., vol. 74, No. 3.

Hamada, et al. Organic light-emitting diodes using 3-or 5-hydroxyflavone-metal complexes., Dec. 8, 1997, American Institute of Physics., vol. 71, No. 23.

Gigli, et al. High-efficiency oligothiopene-based light-emitting diodes., Jul. 26, 1999, American Institute of Physics., vol. 75, No. 4.

Kido et al. Fabrication of highly efficient organic electroluminescent devices., Nov. 9, 1998, American Institute of Physic., vol. 75, No. 4.

Yang, et al. Photoluminescence and electroluminescence properties of dye-doped polymer system., 1997, Elsevier Science S.A., Synthetic Metals., 335-336.

Watanabe et al. Optimization of emitting efficiency in organic LEDs., 1997 Elsevier Science S.A., Synthetic Metals., 203-207.

Liedenbaum., Low voltage of large area polymer LEDs., 1997, Elsevier Science S.A. Synthetic Metals., 109-111.

Hide, et al. Conjugated Polymers as solid-state laser materials., 1997, Elsevier Science S.A., Synthetic Metals., 35-40.

Muckl ,et al. Transient electroluminescence measurements on organic heterolayer light emitting diodes., 2000 Elsevier Science S.A. Synthetic Metals., 91-94.

Baldo, et al. Nature, High-efficiency florescent organic light-emitting devices using a phosphorescent sensitizer, 2000, vol. 402,750-753.

Birnstock, et al., Applied Physics Letters, Screen-printed passive matrix displays based on light-emitting polymers, vol. 78, No. 24., Jun. 2001, 3905-3907.

Chang, et al. Dual-color polymer light-emitting pixels processed by hybrid inkjet printing, Nov. 1989, vol. 73, No. 18, 2561-2563, Applied Physics Letters, 78, 24, 2001, 3905- 3907.

Wurther et al., Synthesis and Energy Transfer Properties of Terminally Substituted Oligothiophenes, Feb. 1995, American Chemical Society, pp. 8090-8099.

Shoustikov et al., Orange and red organic light-emitting devices using aluminum tris(5-hydroxyquinoxaline), 1997, Elsevier Science S.A., Sythetic Metals., 217-221.

Tokito et al., strongly modified emission from organic elelctroluminescent device with a microcavity., 1997. Elsevier Science S.A. Sythetic Metals., 49-52.

Wakimoto et al., Stability characteristics of quinacridone and coumarin molecules as guest dopants in the organic LEDs., 1997, Elsevier Science S.A., Sythetic Metals., 15-19.

Ma et al., Bright blue electroluminescent devices utiliaing poly (N—vinylcarbazole) doped with fluorescent dye., 1997, Elsevier Science S.A., Sythetic Metals., 331-332.

Sano et al., Organic eletroluminescent devices doped condensed polycyclic aromatic compounds., 1997, Elsevier Science S.A., Sythetic Metals., 27-30.

Mitschke et al., The electroluminescence of organic materials., 2000, The Royal Society of Chemistry, 1471-1507.

Barbarella et al., Modified Oligothiophenes with High Photo and Electroluminescence Efficiencies., 1999, Advanced Materals, 11, No. 16.

Schmitz et al., Polymeric Light-Emitting Diodes Based on Poly(p-phenylene ethynylene), Poly(triphenyldiamine), and Spiroquinoxaline., 2001, Advanced Functional Materials, 11, No. 1.

Lamansky et al., Synthesis and Characterization of Phosphorescent Cyclometalated Iridium Complexes., 2001. Dept. of Chemistry. University of Southern California, 1704-1711.

Lamansky et al., Highly Phosphorescent Bis-Cyclometalated Iridium Complexes: Synthesis, Photophysical Characterization, and Use in Organic Light Emitting Diodes., 2001, American Chemical Society, 123, 4304-4312.

Tsutsui et al., High Quantum Efficiency in Organic Light-Emitting Devices with Iridium-Complex as a Triplet Emissive Center., 1999, Japanese Journal fo Applied Physics., vol. 38, L1502-L1504.

Naito et al., Molecular Design for Nonpolymeric Organic Dye Glasses with Thermal Stability Relations between Thermodynamic Parameters and Amorphous Properties., 1993, The Journal of Physical Chemistry, vol. 97, No. 23, 6240-6248.

Barth et al., Electron mobility in tris(8-hydroxy-quinoline)aluminum thin filims determined via transient eletroluminescence from single- and multilayer organic light-emitting diodes., Apr. 1, 2001, Journal of Applied Physics, vol. 89, No. 7, 3711-3719.

Adachi et al., Organic electroluminescence of silole-incorporated polysilane., 2000, Journal of Luminescence, vol. 87 89, 1174-1176.

Clarkson et al., Sprans with four aromatic radicals on the spiro carbon atom., 1930, The Chemistry Laboratory of the Unoversity of Michigan. vol. 52, 2881-2891.

Frank Wurthner, et al., "Synthesis and Energy Transfer Properties of Terminally Substituted Oligothiophenes," J. Am. Chem. Soc. 1995, 117, 8090-8099.

Emele, P., et al., "Dual fluorescence of 9-anthryl-substituted oligothiophenes in nonpolar environment" Chemical Physics 131 (1994) pp. 417-424.

Meyer, D.U., et al., "Time-resolved dual fluorescence and transiet absorption of 9-anthryl oligothiophenes" Chemical Physics 208 (1996) pp. 149-163.

ORGANIC COMPOUNDS FOR ELECTROLUMINESCENCE AND ORGANIC ELECTROLUMINESCENT DEVICES USING THE SAME

This application is a divisional application of U.S. patent application Ser. No. 10/431,349 filed on May 6, 2003, now U.S. Pat. No. 7,485,733 which claims priority to Korean Application No. 10-2003-0010439 filed on Feb. 19, 2003 and Korean Application No. 10-2002-0025084 filed on May 7, 2002, all of which are incorporated by reference, as if fully set forth herein.

BACKGROUND OF THE INVENTION

1. Field of the Invention

The present invention generally relates to organic electroluminescence. More particularly, the present invention pertains to novel organic compounds having electroluminescent (hereinafter referred to as "EL") characteristics and an organic EL device using the organic EL compounds.

2. Description of the Related Art

Organic electroluminescence is one of the instances in which electric current is converted into visible light by internal processes of certain organic molecules. The organic electroluminescence has been applied in display technology, particularly flat panel display technology. Display devices using organic electroluminescence are referred to as an organic EL device or organic EL display. Unlike liquid crystal displays (LCD) requiring an independent light source, organic EL devices generate its own light. Generally, this technology is advantageous over LCD technology in its low power consumption, faster response time, higher brightness level, unlimited viewing angle, and so forth.

The organic EL technology uses various organic compounds. Certain compounds are used for the purpose of generating visible light. Other compounds are used for assisting the light emission by another compounds rather than generating their own light. In order to improve characteristics of the organic EL devices or manufacturing processes thereof, potential new organic compounds are researched.

SUMMARY OF THE INVENTION

One aspect of the present invention provides a compound of Formula I:

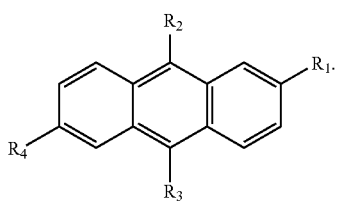

Formula I

At least one of R1 through R4 is represented by Formula II:

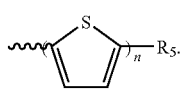

Formula II

In the above-formulas "n: is an integer from 1 to 10. R5 and each of R1-R4 that is not Formula II are preferably non double-spiral identical or different substituent groups chosen from the group consisting of: hydrogen; halo; hydroxyl; mercapto; cyano; nitro; carbonyl; carboxyl; formyl; substituted or unsubstituted C1-C20 alkyl; substituted or unsubstituted C2-C10 alkenyl; substituted or unsubstituted C2-C7 alkynyl; substituted or unsubstituted aryl; substituted or unsubstituted heteroaryl; substituted or unsubstituted C3-C7 cycloalkyl, in which a carbon atom in the ring can optionally be replaced by an oxygen, nitrogen or sulfur atom; substituted or unsubstituted C4-C7 cycloalkenyl, in which a carbon atom in the ring can be optionally replaced by an oxygen, nitrogen or sulfur atom; substituted or unsubstituted C1-C20 alkoxy; substituted or unsubstituted C2-C10 alkenyloxy; substituted or unsubstituted C2-C7 alkynyloxy; substituted or unsubstituted aryloxy; substituted or unsubstituted C1-C20 alkylamine; substituted or unsubstituted C2-C10 alkenylamine; substituted or unsubstituted C2-C7 alkynylamine; substituted or unsubstituted arylamine; substituted or unsubstituted alkylarylamine; substituted or unsubstituted C1-C20 alkylsilyl; substituted or unsubstituted C2-C10 alkenylsilyl; substituted or unsubstituted C2-C7 alkynylsilyl; substituted or unsubstituted arylsilyl; substituted or unsubstituted alkylarylsilyl; substituted or unsubstituted C1-C20 alkylboranyl; substituted or unsubstituted C2-C10alkenylboranyl; substituted or unsubstituted C2-C7 alkynylboranyl; substituted or unsubstituted arylboranyl; substituted or unsubstituted alkylarlboranyl; substituted or unsubstituted C1-C20 alkylthio; substituted or unsubstituted C2-C10 alkenylthio; substituted or unsubstituted C2-C7 alkynylthio; and substituted or unsubstituted arylthio groups.

In the above-formulas, wherein R5 and each of R1-R4 that is not represented by Formula II are preferably non double-spiral substituent groups chosen from the group consisting of: hydrogen, cyano, nitro, substituted or unsubstituted C1-20 alkyl, substituted or unsubstituted C2-C10 alkenyl, substituted or unsubstituted C3-C7 cycloalkyl, substituted or unsubstituted C4-C7 cycloalkenyl, substituted or unsubstituted aryl, substituted or unsubstituted heteroaryl, substituted or unsubstituted C1-C20 alkoxy, substituted or unsubstituted aryloxy, substituted or unsubstituted C1-C20 alkylamine, substituted or unsubstituted arylamine, substituted or unsubstituted alkylarylamine, substituted or unsubstituted C1-C20 alkylsilyl; substituted or unsubstituted arylsilyl; substituted or unsubstituted alkylarylsilyl, substituted or unsubstituted C1-C20 alkylboranyl, substituted or unsubstituted arylboranyl, substituted or unsubstituted alkylarylboranyl, substituted or unsubstituted C1-C20 alkylthio, and substituted or unsubstituted arylthio groups. The substituent groups are further mono- or poly-substituted with identical or different substituent groups selected from the group consisting of: halo, hydroxyl, mercapto, cyano, nitro, amino, carbonyl, carboxyl, formyl, C1-C20 alkyl, C2-10 alkenyl, C2-C7 alkynyl, aryl, heteroaryl, C3-C7 cycloalkyl, 3-7 membered heterocyclic saturated or unsaturated ring, acryl, C1-C20 alkoxy, C2-C10 alkenyloxy, C2-C7 alkynyloxy, C1-C20 alkylamine, C2-C10 alkenylamine, C2-C7 alkynylamine, arylamine, alkylarylamine, C1-C20 alkylsilyl, C2-C10 alkenylsilyl, C2-C7 alkynylsilyl, alkoxysilyl, arylsilyl, alkylarylsilyl, C1-C20 alkylboranyl, C2-C10 alkenylboranyl, C2-C7 alkynylboranyl, arylboranyl, alkylarylboranyl, C1-C20 alkylthio, C2-C10 alkenylthio, C2-C7 alkynylthio and arylthio groups.

The substituent groups are further mono- or poly-substituted with identical or different substituent groups selected from the group consisting of: cyano, nitro, formyl, methyl, ethyl, proply, phenyl, naphthyl, biphenyl, anthracenyl, imidazolyl, thiazolyl, oxazolyl, thiophenyl, pyridyl, pyrimidyl, pyrrolyl, cyclobutenyl, cyclopetenyl, methoxy, ethoxy, propoxy, phenoxy, naphthoxy, methylamine, ethylamine, propylamine, phenylamine, naphthylamine, methylphenylamine, ethylphenylamine, ethylnaphthylamine, dimethylboranyl, diethylboranyl, dipropylboranyl, diphenylboranyl, dinaphthylboranyl, phenylnaphthylboranyl, phenylmethylboranyl, naphthylmethylboranyl, naphthylethylboranyl, trimethylsilyl, triethylsilyl, tripropylsilyl, triphenylsilyl, trinaphthylsilyl, dimethylphenylsilyl, diethylphenylsilyl, diphenylmethylsilyl, methylthio, ethylthio, propylthio, butylthio, phenylthio and naphthylthio groups.

The C3-C7 cycloalkyl and C4-C7 cycloalkenyl groups are 5-6 membered, unsubstituted or substituted, saturated or unsaturated heterocyclic rings. R5 and each of R1-R4 that is not Formula II are preferably non double-spiral substituent groups chosen from the group consisting of methyl, ethyl, propyl, butyl, isopropyl, n-butyl, t-butyl, isobutyl, n-pentyl, neo-pentyl, n-hexyl, ethenyl, propenyl, butenyl, pentenyl, hexenyl, 2-methyl-ethenyl, 2-methyl-propenyl; 2-methyl-butenyl, 2-methyl-pentenyl, 2-methyl-hexenyl, imidazolyl, thiazolyl, oxazoly, thiophenyl, pyridyl, pyrimidyl, pyrrolyl, 2-methylimidazolyl, 2-methyithiazolyl, 2-methyloxazoly, 2-methyithiophenyl, 2-methylpyridyl, 2-methylpyrimidyl, 2-methylpyrrolyl, phenyl, naphthyl, anthracenyl, biphenyl, terphenyl, double-spiro, tetracenyl, 3-methyl-phenyl, 4-methyl-naphthyl, 9-methyl-anthracenyl, 4-methyl-tetracenyl, 2-methyl-imidazolyl, 2-methyloxazolyl, 2-methyl-thiazolyl, 2-methyl-furanyl, 2-methyl-thiophenyl, 2-methyl-pyrazolyl, 2methyl-pyridyl, 2-methyl-pyrimidinyl, methoxy, ethoxy, propoxy, butoxy, pentoxy, hexoxy, isopropoxy, isobutoxy, t-butoxy, neo-pentoxy, phenoxy, naphthoxy, biphenoxy, 3-methyl-phenoxy, 4-methyl-naphthoxy, 2-methyl-biphenoxy, methylamine, ethylamine, propylamine, butylamine, pentylamine, hexylamine, heptylamine, isopropylamine, isobutylamine, t-butylamine, 2-pentylamine, neo-pentylamine, phenylamine, naphthylamine, biphenylamine, anthracenylamine, 3-methyl-phenylamine, 4-methyl-naphthylamine, 2-methyl-biphenylamine, 9-methyl-anthracenylamine, phenylmethylamine, phenylethylamine, naphthylmethylamine, naphthylethylamine, biphenylmethylamine, 3-methyl-phenylmethylamine, phenyl isopropylamine, naphthylisopropylamine, naphthylisobutylamine, biphenylisopropylamine, trimethylsilyl, triethylsilyl, tributylsilyl, tri(isopropyl)silyl, tri(isobutyl)silyl, tri(t-butyl)silyl, tri(2-butypsilyl, triphenylsilyl, trinaphthylsilyl, ribiphenylsilyl, tri(3-methyl phenyOsilyl, tri(4-methylnaphthyl)silyl, tri(2-methylbiphenyl)silyl, phenylmethylsilyl, phenylethylsilyl, naphthylmethylsilyl, naphthylethylsilyl, biphenylmethylsilyl, 3-methyl-phenylmethylsilyl, henylisopropylsilyl, naphthylisopropylsilyl, naphthylisobutylsilyl, biphenylisopropylsilyl, dimethylboranyl, diethylboranyl, dipropylamine, dibutylamine, dipentylamine, diisopropylboranyl, diisobutylboranyl, di(t-butyl)boranyl, isopropylisobutylamine, diphenylboranyl, dinaphthylboranyl, ibiphenylboranyl, di(3-methylphenyl)boranyl, di(4-methylnaphthyl)boranyl, di(2-methylbiphenyl)boranyl, phenylmethylboranyl, phenylethylboranyl, naphthylmethylboranyl, naphthylethylboranyl, biphenylmethylboranyl, 3-methyl-phenylmethylboranyl, phenylisopropylboranyl, naphthylisopropylboranyl, naphthylisobutylboranyl, biphenyl isopropyl boranyl, methylthio, ethylthio, propylthio, butylthio, pentylthio, hexylthio, tri(isopropyl)thio, tri(isobutyl)thio, tri(t-butyl)thio, tri(2-butyl)thio, phenylthio, naphthylthio, biphenylthio, (3-methylphenyl)thio, (4-methylnaphtypthio and (2-methylbiphenyl)thio groups.

In the above-formulas, R5 and each of R1-R4 that is not Formula H are preferably non double-spiral substituent groups chosen from the group consisting of: methyl, ethyl, isopropyl, t-butyl, ethenyl, propenyl, 2-methyl-ethenyl, 2-methyl-propenyl, imidazolyl, thiazolyl, oxazolyl, 2-methylimidazolyl, 2-methylthiazolyl, 2-methyloxazoly, phenyl, naphthyl, biphenyl, terphenyl, anthracenyl, double-spiro, 3-methyl-phenyl, 4-methyl-naphthyl, methoxy, ethoxy, isopropoxy, isobutoxy, phenoxy, naphthoxy, 3-methyl-phenoxy, 4-methyl-naphthoxy, methylamine, ethylamine, isopropylamine, isobutylamine, t-butylamine, phenylamine, naphthylamine, 3-methyl-phenylamine, 4-methyl-naphthylamine, phenylmethylamine, phenylethylamine, naphthylmethylamine, 3-methyl-phenylmethylamine, phenylisopropylamine, trimethylsilyl, triethylsilyl, tri(isopropyl)silyl, tri(isobutyl)silyl, triphenylsilyl, trinaphthylsilyl, tri(3-methylphenyl)silyl, tri(4-methylnaphthyl)silyl, phenylmethylsilyl, phenylethylsilyl, 3-methyl-phenylmethylsilyl, phenyl isopropylsilyl, dimethylboranyl, diethylboranyl, diisopropylboranyl, diisobutylboranyl, diphenylboranyl, dinaphthylboranyl, di(3-methylphenyl)boranyl, di(4-methylnaphthyl)boranyl, phenylmethylboranyl, phenylethylboranyl, 3-methyl-phenylmethylboranyl, phenylisopropylboranyl, methylthio, ethylthio, tri(isopropyl)thio, tri(isobutyl)thio, phenylthio, naphthylthio, (3-methylphenyl)thio and (4-methylnaphthyl)thio groups.

Still in the above-formulas, R5 and each of R1-R4 that is not Formula II are preferably non double-spiral substituent groups chosen from the group consisting of substituted or unsubstituted phenyl, substituted or unsubstituted naphthyl, substituted or unsubstituted biphenyl, substituted or unsubstituted terphenyl, substituted or unsubstituted anthracenyl and substituted or unsubstituted doublespiro groups. The substituted phenyl, naphthyl, biphenyl, terphenyl, anthracenyl and doublespiro groups are substituted with one or more selected from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio.

Still in the above-formulas, only one of R1 through R4 is represented by Formula II. Two of R1 through R4 is represented by Formula II. R1 and R4 are represented by Formula II. R2 and R3 are represented by Formula II. Three of R1 through R4 is represented by Formula II. All of R1 through R4 is represented by Formula II. At least one of R1-R4 is represented by Formula II, and wherein the remaining R1-R4 is or are selected from the group consisting of Formulas 1-1 through 1-14. In these formulas, X, Y and Z are identical or different substituent groups, and each ring moiety where X, Y or Z is attached may be substituted with more than one, identical or different, substituent groups like X, Y or Z. X, Y and Z are chosen from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio. X, Y and Z are chosen from the group consisting of cyano, nitro, methyl, ethyl, isopropyl, t-butyl, methoxy, ethoxy, propoxy, methylthio, imidazolyl, pyridyl, thiazolyl, oxazolyl, furanyl, thiophenyl, pyrrolyl, pyridyl and pyrimidyl.

In Formula I, Formula II is selected from the group consisting of Formulas 2-1 through 2-5. In these formulas, "n" is an integer from 1 to 4; "m" is an integer from 0 to 20. X, Y and Z are identical or different substituent groups. Each ring moiety where X, Y or Z is attached may be substituted with more than one, identical or different, substituent groups like X, Y or Z. X, Y and Z are chosen from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio. X, Y and Z are chosen from the group consisting of cyano, nitro, methyl, ethyl, isopropyl, t-butyl, methoxy, ethoxy, propoxy, methylthio, imidazolyl, pyridyl, thiazolyl, oxazolyl, furanyl, thiophenyl, pyrrolyl, pyridyl and pyrimidyl.

The compound of Formula I is selected from the group consisting of Compounds 1 through 96. The compound of Formula I is selected from the group consisting of Compounds 1 through 60. The compound of Formula I is selected from the group consisting of Compounds 1 through 24. The compound of Formula I is selected from the group consisting of Compounds 1, 4, 12, 14, 19, 21, 23, 25, 27 and 29. The compound has a melting point above about 300° C. The compound has a band-gap corresponding to visible light emission. The band-gap for the visible light emission is from about 1.8 eV to about 3.5 eV.

Another aspect of the present invention provides a light-emitting material, which comprises one or more of the above-described compounds, each compound having a band gap. The light-emitting material further comprises one or more additional light-emitting compounds that are not represented by Formula I, wherein each additional compound has a band gap. The band gap of at least one of the additional compound is from about 80% up to 100% of the value of the band gap of the compound represented by Formula I. The light-emitting material further comprises one or more light-emitting compounds selected from the group consisting of BCzVBi, perylene, rubrene, DCJTB, quinacridone, coumarine, nile red, DCM1, DCM2, tetradiphenylamino pyrimido-pyrimidine, pyrydinothiadiazole and Compounds 201-220.

Other aspects of the present invention provide a light-emitting material comprising one or more of the above-described compounds of Formula I; a hole-transporting material comprising one or more of the above-described compounds of Formula I; an electron-transporting material comprising one or more of the above-described compounds of Formula I.

Another aspect of the present invention provides a solid film comprising one or more of the above-described compounds of Formula I. The one or more compounds in the solid film are in an amorphous form. The solid film further comprises one or more additional compounds that is not represented by Formula I. At least one additional compound that is not represented by Formula I has a band gap smaller than that of the compound represented by Formula I. The band gap of the additional compound is from about 70% up to 100% of the band gap of the compound represented by Formula I. The band gap of the additional compound is from about 90% up to 100% of the band gap of the compound represented by Formula I. One compound represented by Formula I is a host material in the solid film. At least one compound represented by Formula I is a dopant in the solid material. One additional compound that is not represented by Formula I is a host material in the solid film. At least one additional compound that is not represented by Formula I is a dopant in the solid film. At least one additional compound is a light-emitting compound. Each additional compound that is not represented by Formula I has one or more properties selected from the group consisting of visible light emission, electron transportation, electron injection, hole transportation, and hole injection. At least one additional compound is a fluorescent or phosphorescent light-emitting compound. The solid film has a thickness from about 5 nm to about 100 nm. Each compound represented by Formula I has one or more properties selected from the group consisting of visible light emission, electron transportation, electron injection, hole transportation, and hole injection. At least one compound represented by Formula I has a band gap corresponding to visible light emission. The solid film is formed by vapor deposition, inkjet printing or spin coating of the one or more compound represented by Formula I with or without a material that is not represented by Formula I. The solid film, comprising the light-emitting material.

Another aspect of the present invention provides a method of making the above-described solid film. The method comprises: providing a support; and forming at least one layer comprising the one or more compounds therein over the support, wherein the at least one layer constitute the solid film. The layer is formed by physical vapor deposition, inkjet printing or spin coating of the compound over the support.

Another aspect of the present invention provides an organic electroluminescent ("EL") device, which comprises: an anode; a cathode; and the above-described solid film located between the anode and cathode. In the organic EL device, the solid film serves one of more functions selected from the group consisting of light-emission, hole-injection hole-transportation, electron-transportation and electron-injection. The organic EL device further comprises one or more additional solid film between the anode and cathode. The organic EL device is supported by a substrate, and wherein the substrate contacts either the anode or the cathode. The solid film constitutes a light-emitting layer. The light-emitting layer comprises one or more fluorescent or phosphorescent light-emitting materials. The organic EL device further comprises one or more additional solid films between the anode and cathode. The organic EL device further comprises a hole-injecting layer, a hole-transporting or both between the anode and the light-emitting layer. The organic EL device further comprises an electron-injecting layer, an electron-transporting or both between the cathode and the light-emitting layer.

In the organic EL device, the light-emitting layer comprises at least two compounds capable of emitting light therein. At least one compound represented by Formula I has a band gap corresponding to visible light emission. The light-emitting layer further comprises at least one additional light-emitting compound. The additional light-emitting compound is not represented by Formula I. The additional light-emitting compound is also represented by Formula I. The additional light-emitting compound has a quantum efficiency higher than that of the at least one compound represented by Formula I. The additional light-emitting compound has a band gap smaller than that of the at least one compound represented by Formula I. The band gap of the additional compound is from about 70% up to 100% of the band gap of the compound represented by Formula I. The band gap of the additional compound is from about 80% up to 100% of the band gap of the compound represented by Formula I. The band gap of the additional compound is from about 90% up to 100% of the band gap of the compound represented by Formula I. The additional light-emitting compound is a phosphorescent light-emitting compound.

Still in the organic EL device, at least one compound represented by Formula I is selected from the group consisting of Compounds 1 through 96. The compound of Formula I is selected from the group consisting of Compounds 1 through 60. The compound of Formula I is selected from the group consisting of Compounds 1 through 24. The compound of Formula I is selected from the group consisting of Compounds 14, 12, 14, 19, 21, 23, 25, 27 and 29. The light-emitting layer further comprises therein one or more light-emitting compounds selected from the group consisting of BCzVBi, perylene, rubrene, DCJTB, quinacridone, coumarine, nile red, DCM1, DCM2, tetradiphenylamino pyrimidopyrimidine, pyrydinothiadiazole and Compounds 201-220.

Still another aspect of the present invention provides an electronic apparatus comprising a display, wherein the display comprises the above described organic EL device with the above-described various features.

Still another aspect of the present invention provides a method of generating visible light from the above-described organic EL device. The method comprises: applying electric power between the anode and cathode of the device; injecting electrons from the cathode toward the solid film; injecting holes from the anode toward the solid film; and allowing recombination of at least part of the injected electrons and holes in an area between the cathode and anode, thereby generating visible light from the area. One or more light-emitting materials are located in the area. The solid film constitutes a light-emitting layer. At least one compound represented by Formula I is a light-emitting compound. The solid film further comprises an additional light-emitting compound therein. The additional light-emitting compound is not represented by Formula I. The additional light-emitting compound has higher quantum efficiency than the compound represented by Formula I. The solid film serves one of more functions selected from the group consisting of light-emission, hole-injection hole-transportation, electron-transportation and electron-injection.

Still another aspect of the present invention provides a method of manufacturing the above-described organic EL device. The method comprises: providing a substrate; forming a first conductive layer; forming the solid film; and forming a second conductive layer, wherein either of the first and second conductive layers corresponds to the anode or cathode. The formation of the solid film comprises vapor depositing, inkjet printing or spin-coating at least one compound represented by Formula I. The solid film so formed, at least one additional compound that is not represented by Formula I is incorporated. The method further comprises forming one or more additional solid films comprising organic compounds between the first and second conductive layers.

DETAILED DESCRIPTION

Figure 1:
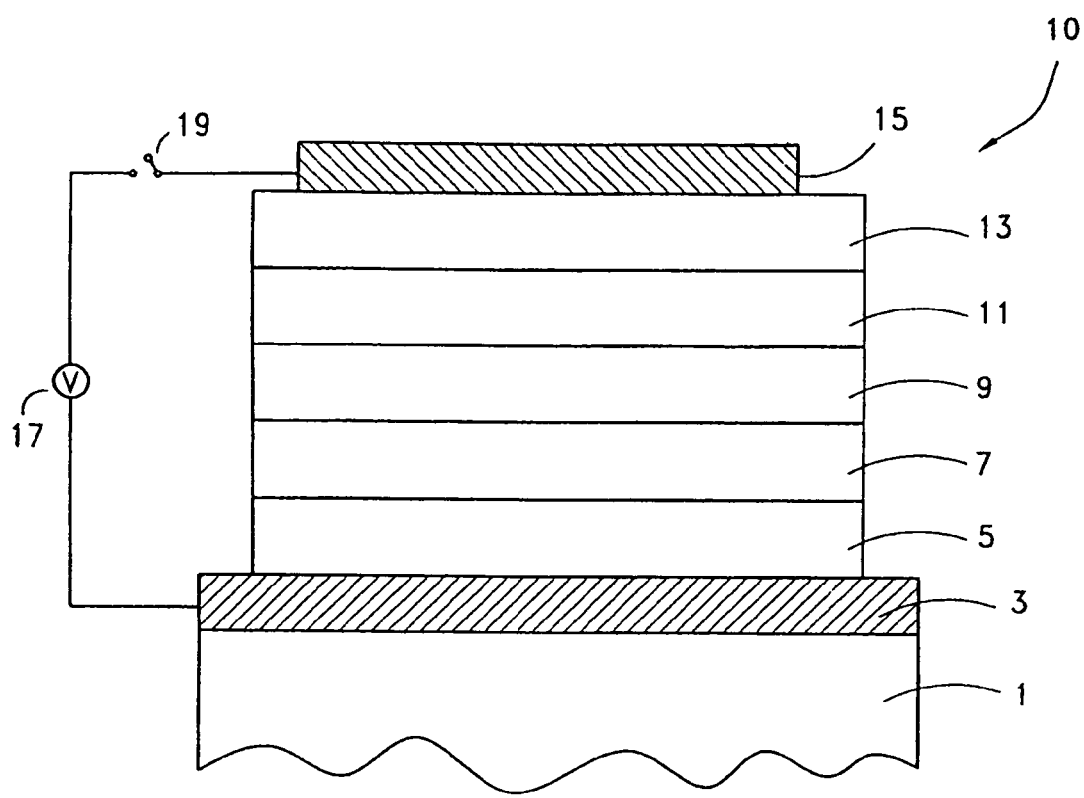
FIGS. 1-6 illustrate simplified cross-sectional views of various exemplary constructions of organic EL devices in accordance with the present invention.

Now the various aspects of the present invention will be discussed in more detail. It is to be understood at the outset of the description that persons of skill in the appropriate arts may modify the invention described herein while still achieving the favorable results of the invention. Accordingly, the following description is to be understood as being a broad, teaching disclosure directed to persons of skill in the appropriate arts, and not as limiting upon the present invention.

New Compounds

One aspect of the present invention is directed to a novel group of compounds represented by Formula I:

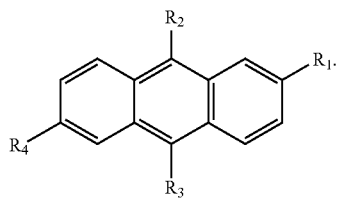

Formula I

R1 through R4 are substituent groups to be defined below and may be identical to or different from one another. One or more of R1 through R4 is represented by Formula II:

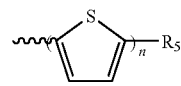

Formula II

In Formula II, "n" is an integer of 1, 2, 3, 4, 5, 6, 7, 8, 9 or 10. Preferably, "n" is 1, 2, 3 or 4, and more preferably, 1 or 2. R5 is a substituent group, which may be identical to or different from any of R1-R4 of Formula I.

In Formula I, only one, two, three or all of R1-R4 may be represented by Formula II. Preferably, one or two of R1-R4 are represented by Formula II. When only one of R1-R4 is Formula II, it is preferably R1 or R4 that is Formula II. When two of R1-R4 are Formula II, preferably, the pair of R1 and R4 or the pair of R2 and R3 are represented by Formula II.

The substituent groups for R5 and R1-R4 that is not represented by Formula II are: hydrogen; halo; hydroxyl; mercapto; cyano; nitro; carboxyl; formyl; substituted or unsubstituted C1-C20 alkyl; substituted or unsubstituted C2-C10 alkenyl; substituted or unsubstituted C2-C7 alkynyl; substituted or unsubstituted aryl; substituted or unsubstituted heteroaryl; substituted or unsubstituted C3-C7 cycloalkyl, in which a carbon atom in the ring can optionally be replaced by an oxygen, nitrogen or sulfur atom; substituted or unsubstituted C4-C7 cycloalkenyl, in which a carbon atom in the ring can be optionally replaced by an oxygen, nitrogen or sulfur atom; substituted or unsubstituted C1-C20 alkoxy; substituted or unsubstituted C2-C10 alkenyloxy; substituted or unsubstituted C2-C7 alkynyloxy; substituted or unsubstituted aryloxy; substituted or unsubstituted C1-C20 alkylamine; substituted or unsubstituted C2-C10 alkenylamine; substituted or unsubstituted C2-C7 alkynylamine; substituted or unsubstituted arylamine; substituted or unsubstituted alkylarylamine; substituted or unsubstituted C1-C20 alkylsilyl; substituted or unsubstituted C2-C10 alkenylsilyl; substituted or unsubstituted, C2-C7 alkynylsilyl; substituted or unsubstituted arylsilyl; substituted or unsubstituted alkylarylsilyl; substituted or unsubstituted C1-C20 alkylboranyl; substituted or unsubstituted C2-C10 alkenylboranyl; substituted or unsubstituted C2-C7 alkynylboranyl; substituted or unsubstituted arylboranyl; substituted or unsubstituted alkylarylboranyl; substituted or unsubstituted C1-C20 alkylthio; substituted or unsubstituted C2-C10 alkenylthio; substituted or unsubstituted C2-C7 alkynylthio; or substituted or unsubstituted arylthio.

The term "C1-C20 alkyl" or "unsubstituted C1-C20 alkyl", whether as part of another term or not, denotes straight-chain, saturated hydrocarbon radicals such as methyl, ethyl, n-propyl, n-butyl, n-amyl, n-hexyl, n-decanyl, n-eicosanyl and the like. The term "substituted C1-C20 alkyl" denotes C1-C20 alkyl, which is mono- or poly-substituted with the same or with different substituent group, namely: halo, hydroxyl, mercapto, cyano, nitro, amino, carbonyl, carboxyl, formyl, C1-C20 alkyl, C2-10 alkenyl, C2-C7 alkynyl, aryl, heteroaryl, C3-C7 cycloalkyl, 3-7 membered heterocyclic saturated or unsaturated ring, acryl, C1-C20 alkoxy, C2-C10 alkenyloxy, C2-C7 alkynyloxy, C1-C20 alkylamine, C2-C10 alkenylamine, C2-C7 alkynylamine, arylamine, alkylarylamine, C1-C20 alkylsilyl, C2-C10 alkenylsilyl, C2-C7 alkynylsilyl, arylsilyl, alkylarylsilyl, C1-C20 alkylboranyl, C2-C10 alkenylboranyl, C2-C7 alkynylboranyl, arylboranyl, alkylarylboranyl, C1-C20 alkylthio, C2-C10 alkenylthio, C2-C7 alkynylthio or arylthio, which are collectively referred to as "listed substituent groups" hereinafter. The term "heterocyclic" refers to a ring structure one or more skeletal carbons are replaced an oxygen, nitrogen or sulfur atom.

The term "C2-C10 alkenyl" or "unsubstituted C2-C10 alkenyl", whether as part of another term or not, denotes straight-chain hydrocarbon radicals having one or more double bonds between two neighboring carbon atoms. Examples of the C2-C10 alkenyl groups are vinyl, allyl, but-2-enyl, pent-2-enyl, hept-3-enyl, dec-1,3-dien-yl and the like. The term "substituted C2-C10 alkenyl" denotes an C2-C10 alkenyl group, which is mono- or poly-substituted with one or more of the same or different substituent groups chosen from the listed substituent groups. Examples of the substituted C2-C10 alkenyl groups are isoprop-2-enyl, isobutenyl, t-butenyl, 2-methyl-2-decenyl and the like.

The term "C2-C7 alkynyl" or "unsubstituted C2-C7 alkynyl", whether as part of another term or not, denotes straight-chain hydrocarbon radicals having one or more triple bonds between two neighboring carbon atoms. Examples of C2-C7 alkynyl groups are ethynyl, prop-1-ynyl, but-2-ynyl, hex-2-ynyl, hept-3-ynyl and the like. The term "substituted C2-C7 alkynyl" denotes an C2-C7 alkynyl group, which is mono- or poly-substituted with one or more of the same or different substituent groups chosen from the listed substituent groups. Examples of the substituted C2-C7 alkynyl groups are 2-methylethynyl, 2-methylpropynyl, 2-methylbutynyl, 3-methoxyheptynyl and the like.

The term "aryl" or "unsubstituted aryl", whether as part of another term or not, refers to single or multiple, aromatic hydrocarbon rings. In the cases of multiple rings, two or more rings are fused or linked without an intervening aliphatic chain. For example, the aryl groups denote phenyl, biphenyl, terphenyl, naphthyl, anthracenyl, rubrenyl, perylenyl and the like. The term "substituted aryl" refers to an aryl group, which is mono- or poly-substituted with one or more of the same or different non-aryl substituent groups chosen from the listed substituent groups. Examples of the substituted aryl groups are methylphenyl, methoxyphenyl, methylbiphenyl, methylterphenyl, methylnaphthyl, methoxynaphthyl, methylanthracenyl and the like.

The term "heteroaryl" or "unsubstituted heteroaryl", whether as part of another term or not, refers to single or multiple, aromatic hydrocarbon rings, in which at least one skeletal carbon atom is replaced by an oxygen, nitrogen or sulfur atom. In the cases of multiple rings, two or more rings are fused, including optionally benzo-fused, or linked without an intervening aliphatic chain. For example, the heteroaryl groups are oxazolyl, imidazolyl, thiazolyl, thiopenyl, furanyl, pyridyl, pyrimidyl, pyrrolyl and the like. The term "substituted heteroaryl" refers to an heteroaryl group, which is mono- or poly-substituted with one or more of the same or different non-heteroaryl substituent groups chosen from the listed substituent groups. For example, the substituted aryl groups are 2-methyl-oxazolyl, 2-methyl-imidazolyl, 2-methyl-thiazolyl, 3,4-dimethyl-thiopenyl, 2-methyl-furanyl, 2-methyl-pyridyl, 2-methyl-pyrimidyl, 2-methyl-pyrrolyl and the like.

The substituent term "C3-C7 cycloalkyl" or "unsubstituted C3-C7 cycloalkyl" refers to a saturated closed ring structure with 3-7 carbon atoms in the ring. One or more carbon atoms in the ring can be optionally replaced by an oxygen, nitrogen or sulfur atom, which is also referred to as "saturated heterocyclic ring". Examples of the C3-C7 cycloalkyl groups are cyclopropyl, cyclobutyl, cyclopentyl, cyclohexyl, cycloheptyl and the like. The term "substituted C3-C7 cycloalkyl" refers to a C3-C7 cycloalkyl group having one or more substitution at the carbon or non-carbon ring member with one or more of the same or different substituent groups chosen from the listed substituent groups. Examples of the substituted C3-C7 cycloalkyl groups are methylcyclopropyl, methylcyclobutyl, methylcyclopentyl, methylcyclohexyl, methylcycloheptyl and the like.

The substituent term "C4-C7 cycloalkenyl" or "unsubstituted C4-C7 cycloalkenyl" refers to a ring structure made of 4-7 carbon atoms with at least one double bond. One or more carbon atoms in the ring can be optionally replaced by an oxygen, nitrogen or sulfur atom, which is also referred to as an "unsaturated heterocyclic ring." For example, the C4-C7 cycloalkenyl groups denote 3-cyclopentenyl, 4-cyclohexenyl, 5-cycloheptenyl and the like. The term "substituted C4-C7 cycloalkenyl" refers to a C4-C7 cycloalkenyl group having one or more substitution at the carbon or non-carbon ring member with one or more of the same or different substituent groups chosen from the listed substituent groups. For example, the substituted C4-C7 cycloalkenyl groups denote 2-methyl-3-cyclopentenyl, 2-methyl-4-cyclohexenyl, 2-methyl-cycloheptenyl and the like.

The term "C1-C20 alkoxy" or "unsubstituted C1-C20 alkoxy" denotes an oxygen radical substituted with a C1-C20 alkyl group. Examples of the C1-C20 alkoxy groups are methoxy, ethoxy, n-propoxy, n-butoxy, n-decanoxy, n-dodecanoxy, n-eicosanoxy and the like. The term "substituted C1-C20 alkoxy" refers to a C1-C20 alkoxy group, which is mono- or poly-substituted in the alkyl part with one or more of the same or different substituent groups chosen from the listed substituent groups. Examples of the substituted C1-C20 alkoxy groups are 1-methylethoxy, 1-methyl-n-propoxy, 1-methyl-n-butoxy, 5-methoxydecanoxy, 3-methyl-dodecanoxy, 3-phenylicosanoxy and the like.

The term "C2-C10 alkenyloxy" or "unsubstituted C2-C10 alkenyloxy" denotes an oxygen radical substituted with a C2-C10 alkenyl group. For example, the C2-C10 alkenyloxy groups denote ethenyloxy, prop-1-enyloxy, but-1-enyloxy, hept-3-enyloxy, dec-2-enyloxy and the like. The term "substituted C2-C10 alkenyloxy" refers to a C2-C10 alkenyloxy group, which is mono- or poly-substituted in the alkenyl part with one or more of the same or different substituent groups chosen from the listed substituent groups. For example, the substituted C2-C10 alkenyloxy groups are 1-methylethenyloxy, 1-methyl-1-propenyloxy, 1-methyl-1-butenyloxy, 2-methyl-1-heptyloxy, 2-methyl-1-decenyloxy and the like.

The term "C2-C7 alkynyloxy" or "unsubstituted C2-C7 alkynyloxy" refers to an oxygen radical substituted with a C2-C7 alkynyl group. Examples of the C2-C7 alkynyloxy groups are ethynyloxy, 1-propynyloxy, 1-butynyloxy, 1,3-hept-diynyloxy and the like. The term "substituted C2-C7 alkynyloxy" refers to a C2-C7 alkynyloxy group, which is mono- or poly-substituted in the alkynyl part with one or more of the same or different substituent groups chosen from the listed substituent groups. Examples of the substituted C2-C7 alkynyloxy groups are 2-methyl-ethynyloxy, 2-methyl-1-propynyloxy, 2-methyl-1-butynyloxy, 3-methoxy-1-heptynyloxy and the like.

The term "aryloxy" or "unsubstituted aryloxy" denotes groups having an oxygen radical substituted with an aryl group. For example, the aryloxy groups are phenyloxy, naphthyloxy, anthracenyloxy, biphenyloxy, ruburenyloxy, perylenyloxy and the like. The term "substituted aryloxy" refers to an aryloxy group, which is mono- or poly-substituted in the aryl part with one or more of the same or different substituent groups chosen from the listed substituent groups. For example, the substituted aryloxy groups denote 2-methyl-phenyloxy, 4-methyl-naphthyl-2-oxy, 9-methyl-anthracenyl-1-oxy, 2-methyl-biphenyloxy, 2-methyl-ruburenyloxy, 2-methyl-perylenyloxy and the like.

The term "C1-C20 alkylamine" or "unsubstituted C1-C20 alkylamine" denotes a nitrogen radical substituted with one or two identical or different C1-C20 alkyl groups. For example, the C1-C20 alkylamine groups include methylamine, ethylamine, propylamine, butylamine, pentylamine, heptadecanylamine and eicosanylamine. The term "substituted C1-C20 alkylamine" refers to a C1-C20 alkylamine group, which is mono- or poly-substituted in the alkyl part with one or more of the same or different substituent groups chosen from the listed substituent groups. For example, the substituted C1-C20 alkylamine groups include isopropylamine, N-propyl-N-(2-methoxy)butylamine, 2-methylbutylamine, N-butyl-N-(2-methyl)heptylamine and N-2-butyl-N-(2-methyl)heptadecanylamine.

The term "C2-C10 alkenylamine" or "unsubstituted C2-C10 alkenylamine" denotes a nitrogen radical substituted with one or two identical or different C2-C10 alkenyl groups, in which a C1-C20 alkyl can also be attached to the nitrogen atom in case where only one C2-C10 alkenyl group is attached to the nitrogen atom. Examples of the C2-C10 alkenylamine groups are ethenylamine, 1-propenylamine, 1-butenylamine, 1-heptenylamine, 1-decenylamine and the like. The term "substituted C2-C10 alkenylamine" refers to a C2-C10 alkenylamine group, which is mono- or poly-substituted in the alkenyl or alkyl part with one or more of the same or different substituent groups chosen from the listed substituent groups. Examples of the substituted C2-C10 alkenylamine groups are 1-methyl-ethenylamine, 1-methyl-1-propenylamine and 1-methyl-1-butenylamine, 1-methyl-1-heptenylamine, 2-methyl-1-decenylamine and the like.

The term "C2-C7 alkynylamine" or "unsubstituted C2-C7 alkynylamine" denotes a nitrogen radical substituted with one or two identical or different C2-C7 alkynyl groups, in which a C1-C20 alkyl or C2-C10 alkenyl can also be attached to the nitrogen atom in case only one C2-C10 alkenyl group is attached to the nitrogen atom. Examples of the C2-C10 alkynylamine groups are ethynylamine, 1-propynylamine, 1-butynylamine, 2-heptynylamine, 1-decynylamine and the like. The term "substituted C2-C7 alkynylamine" refers to a C2-C7 alkynylamine group, which is mono- or poly-substituted in one or more of the alkyl, alkenyl and alkynyl parts with one or more of the same or different substituent groups chosen from the listed substituent groups. Examples of substituted C2-C7 alkynylamine groups are isopropynylamine, 2-methyl-1-butynylamine, 3-methyl-2-hepynylamine, 2-methyl-1-decynylamine and the like.

The term "arylamine" or "unsubstituted arylamine" denotes a nitrogen radical substituted one or two identical or different aryl or heteroaryl groups. Examples of the arylamine groups are phenylamine, 1-naphthylamine, 9-anthracenylamine, biphenylamine, ruburenylamine, perylenylamine and the like. The term "substituted arylamine" refers to an arylamine group, which is mono- or poly-substituted in the ring part with one or more of the same or different substituent groups chosen from the listed substituent groups. Examples of the substituted arylamine groups are 3-methylphenylamine, 9-methoxyanthracenylamine and the like.

The term "alkylarylamine," "arylalkylamine," "unsubstituted arylalkylamine" or "unsubstituted alkyllarylamine" denotes a nitrogen radical substituted with both an aryl or heteroaryl group and one of the C1-C20 alkyl, C2-C10 alkenyl, C2-C7 alkynyl, C1-C20 alkoxy, C2-C10 alkenyloxy and C2-C7 alkynyloxy groups. Examples of the alkylarylamine groups are N-methyl-N-phenylamine, N-ethyl-N-phenylamine, N-ethyl-N-(1-naphthyl)amine, N-methyl-N-(9-anthracenyl)amine, N-ethenyl-N-phenylamine, N-ethenyl-N-(1-naphthyl)amine, N-ethynyl-N-phenylamine, N-ethynyl-N-(1-naphthyl)amine and the like. The term "substituted alkyllarylamine" or "substituted arylalkylamine" refers to an alkyllarylamine group, which is mono- or poly-substituted in the ring part, non-ring part or both with one or more of the same or different substituent groups chosen from the listed substituent groups. Examples of the substituted alkylarylamine groups are N-isopropyl-N-phenylamine, N-phenyl-N-(4-propyl-1-naphthyl)amine and the like.

The term "C1-C20 alkylsilyl" or "unsubstituted C1-C20 alkylsilyl" denotes a silicon radical substituted with one or more identical or different C1-C20 alkyl groups. For example, the alkylsilyl groups include trimethylsilyl, triethylsilyl, tripropylsilyl, tridecanylsilyl and trieicosanylsilyl. The term "substituted C1-C20 alkylsilyl" refers to a C1-C20 alkylsilyl group, which is mono- or poly-substituted in one or more of the C1-C20 alkyl parts with one or more of the same or different substituent groups chosen from the listed substituent groups. For example, the substituted alkylsilyl groups include diisopropylmethylsilyl, di(isobutyl)methylsilyl, di(decanyl)isopropylsilyl and di(eicosanyl)methylsilyl.

The term "C2-C10 alkenylsilyl" or "unsubstituted C2-C10 alkenylsilyl" denotes a silicon radical substituted with one or more identical or different C2-C10 alkenyl groups, in which one or more C1-C20 alkyl groups can also be attached to the silicon. For example, the alkenylsilyl groups include triethenylsilyl, tripropenylsilyl tributenylsilyl, triheptenylsilyl and tridecenylsilyl. The term "substituted C2-C10 alkenylsilyl" refers to a C2-C10 alkenylsilyl group, which is mono- or poly-substituted in the alkyl or alkenyl part with one or more of the same or different substituent groups chosen from the listed substituent groups. For example, the substituted C2-C10 alkenylsilyl groups include tri(2-methylethenyl)silyl, tri(2-methylpropenyl)silyl, tri(2-methylheptenyl)silyl and tri(2-methyldecenyl)silyl.

The term "C2-C7 alkynylsilyl" or "unsubstituted C2-C7 alkynylsilyl" denotes a silicon radical substituted with one or more identical or different C2-C10 alkynyl groups, in which one or more of the C1-C20 alkyl and C2-C10 alkenyl groups can also be attached to the silicon. For example, the alkynylsilyl groups include triethynylsilyl, tripropynylsilyl, tributynylsilyl, triheptenylsilyl and tridecenylsilyl. The term "substituted C2-C7 alkynylsilyl" refers to a C2-C7 alkynylsilyl group, which is mono- or poly-substituted in the alkyl, alkenyl or alkynyl part with one or more of the same or different substituent groups chosen from the listed substituent groups. The substituted C2-C7 alkynylsilyl groups include, for example, tri(2-methylethynyl)silyl, tri(2-methylpropynyl)silyl, tri(2-methylbutynyl)silyl, tri(2-methylheptynyl)silyl and tri(2-methyldecenyl)silyl.

The term "arylsilyl" or "unsubstituted arylsilyl" denotes a silicon radical substituted with one or more identical or different aryl or heteroaryl groups. For example, the arylsilyl groups include triphenylsilyl, trinaphthylsilyl and tribiphenylsilyl. The term "substituted arylsilyl" refers to an arylsilyl group, which is mono- or poly-substituted in the aryl part with one or more of the same or different substituent groups chosen from the listed substituent groups. For example, the substituted arylsilyl groups include tri(2-methylphenyl)silyl, tri(4-methylnaphthyl)silyl and tri(2-methylbiphenyl)silyl.

The term "alkyllarylsilyl," "arylalkylsilyl," "unsubstituted arylalkylsilyl" or "unsubstituted alkyllarylsilyl" denotes a silicon radical substituted with one or more identical or different aryl or heteroaryl groups and at the same time one of the C1-C20 alkyl, C2-C10 alkenyl, C2-C7 alkynyl, C1-C20 alkoxy, C2-C10 alkenyloxy and C2-C7 alkynyloxy groups. Examples of the alkylarylsilyl groups are diphenylmethylsilyl, dinaphthylmethylsilyl, diphenylethylsilyl, dinaphthylethenylsilyl, dianthracenylethynylsilyl and the like. The term "substituted alkyllarylsilyl" refers to an alkyllarylsilyl group, which is mono- or poly-substituted in the ring part, non-ring part or both with one or more of the same or different substituent groups chosen from the listed substituent groups. Examples of the substituted alkyllarylsilyl groups are di(2-methylphenyl)methylsilyl, di(4-methylnaphthyl)methylsilyl and the like.

The term "C1-C20 alkylboranyl" or "unsubstituted C1-C20 alkylboranyl" denotes a boron radical substituted with one or more identical or different C1-C20 alkyl groups. For example, the alkylboranyl groups include dimethylboranyl, diethylboranyl, dipropylboranyl, diheptylboranyl, didecanylboranyl and di(eicosanyl)boranyl. The term "substituted C1-C20 alkylboranyl" refers to a C1-C20 alkylboranyl group, which is mono- or poly-substituted in one or more of the C1-C20 alkyl parts with one or more of the same or different substituent groups chosen from the listed substituent groups. For example, the substituted alkylboranyl groups include di(isopropyl)boranyl, di(isobutyl)boranyl, di(2-methylheptynyl)boranyl, di(2-methyldecanyl)boranyl and di(2-methyleicosanyl)boranyl The term "C2-C10 alkenylboranyl" or "unsubstituted C2-C10 alkenylboranyl" denotes a boron radical substituted with one or two identical or different C2-C10 alkenyl groups, in which a C1-C20 alkyl groups can also be attached to the boron atom in case only one C2-C10 alkenyl group is attached to the boron. For example, the alkenylboranyl groups include diethenylboranyl, dipropenylboranyl, dibutenylboranyl, diheptenylboranyl and didecanylboranyl. The term "substituted C2-C10 alkenylboranyl" refers to a C2-C10 alkenylboranyl group, which is mono- or poly-substituted in the alkyl or alkenyl part with one or more of the same or different substituent groups chosen from the listed substituent groups. Examples of the substituted alkenylboranyl groups are di(1-methylethenyl)boranyl and di(1-methylprop-1-enyl)boranyl, di(2-methlheptenyl)boranyl, di(2-methyldecanyl)boranyl and the like.

The term "C2-C7 alkynylboranyl" or "unsubstituted C2-C7 alkynylboranyl" denotes a boron radical substituted with one or two identical or different C2-C7 alkynyl groups, in which a C1-C20 alkyl or C2-C10 alkenyl group can also be attached to the boron atom in case only one C2-C7 alkynyl group is attached to the boron. For example, the alkynylboranyl groups include diethynylboranyl, dipropynylboranyl, dibutynylboranyl, dihexynylboranyl and diheptylboranyl.

The term "substituted C2-C7 alkynylboranyl" refers to a C2-C7 alkynylboranyl group, which is mono- or poly-substituted in the alkyl, alkenyl or alkynyl part with one or more of the same or different substituent groups chosen from the listed substituent groups. The substituted C2-C7 alkynylboranyl groups include, for example, di(2-methylethynyl)boranyl, di(2-methylpropynyl)boranyl, di(2-methylbutynyl)boranyl, di(2-methylhexynyl)boranyl and di(2-methylheptyl)boranyl.

The term "arylboranyl" or "unsubstituted arylboranyl" denotes a boron radical substituted with one or more identical or different aryl or heteroaryl groups. Examples of the arylboranyl groups are diphenylboranyl, naphthylboranyl, dinaphthylboranyl, dibiphenylboranyl, ruburenylboranyl, perylenylboranyl and the like. The term "substituted arylboranyl" refers to an arylboranyl group, which is mono- or poly-substituted in the aryl part with one or more of the same or different substituent groups chosen from the listed substituent groups. Examples of the substituted arylboranyl groups are di(3-methylphenyl)boranyl, di(4-methylnaphth-1-yl)boranyl, di(2-methylbiphenyl)boranyl and the like.

The term "alkyllarylboranyl," "arylalkylboranyl," "unsubstituted arylalkylboranyl" or "unsubstituted alkyllarylboranyl" denotes a boron radical substituted with an aryl or heteroaryl group and at the same time one of the C1-C20 alkyl, C2-C10 alkenyl, C2-C7 alkynyl, C1-C20 alkoxy, C2-C10 alkenyloxy and C2-C7 alkynyloxy groups. Examples of the alkylarylboranyl groups are ethylphenylboranyl, methylnaphthylboranyl, methylbiphenylboranyl, ethenylnaphthylboranyl, ethynylphenylboranyl and the like. The term "substituted alkyllarylboranyl" refers to an alkyllarylboranyl group, which is mono- or poly-substituted in the ring part, non-ring part or both with one or more of the same or different substituent groups chosen from the listed substituent groups. Examples of the substituted alkyllarylboranyl groups are methyl(4-methylnaphthyl)boranyl, ethyl(2-methylphenyl)boranyl, methyl(2-methylbiphenyl)boranyl and the like.

The term "C1-C20 alkylthio" or "unsubstituted C1-C20 alkylthio" denotes a sulfur radical substituted with a C1-C20 alkyl group. For example, the alkylthio groups include methylthio, ethylthio, n-propylthio, n-butylthio, n-heptylthio, n-decanylthio and n-eicosanylthio. The term "substituted C1-C20 alkylthio" refers to a C1-C20 alkylthio group, which is mono- or poly-substituted in one or more of the C1-C20 alkyl parts with one or more of the same or different substituent groups chosen from the listed substituent groups. For example, the substituted alkylthio groups include isopropylthio, isobutylthio, neo-pentylthio, 2-methylheptylthio, 2-methyldecanylthio and 2-methyleicosanylthio.

The term "C2-C10 alkenylthio" or "unsubstituted C2-C10 alkenylthio" denotes groups having a sulfur radical substituted with a C2-C10 alkenyl group. For example, the alkenylthio groups include ethenylthio, propenylthio, butenylthio and decenylthio. The term "substituted C2-C10 alkenylthio" refers to a C2-C10 alkenylthio group, which is mono- or poly-substituted in the alkenyl part with one or more of the same or different substituent groups chosen from the listed substituent groups. For example, the substituted alkenylthio groups include 1-methylethenylthio, 1-methyl-2-propenylthio and 1-methyl-2-butenylthio.

The term "C2-C7 alkynylthio" or "unsubstituted C2-C7 alkynylthio" denotes groups having a sulfur radical substituted with a C2-C7 alkynyl group. For example, the alkynylthio groups include ethynylthio, propynylthio, butynylthio and heptynylthio. The term "substituted C2-C7 alkynylthio" refers to a C2-C7 alkynylthio group, which is mono- or poly-substituted in the alkynyl part with one or more of the same or different substituent groups chosen from the listed substituent groups. The substituted C2-C7 alkynylthio groups include, for example, 2-methyl-ethynylthio, 2-methylpropynyl, 2-methylbutynylthio and 2-methylheptynylthio.

The term "arylthio" or "unsubstituted arylthio" denotes groups having a sulfur atom substituted with an aryl groups. For example, the arylthio group includes phenylthio, naphthylthio, anthracenylthio and biphenylthio. The term "substituted arylthio" refers to an arylthio group, which is mono- or poly-substituted in the aryl part with one or more of the same or different substituent groups chosen from the listed substituent groups. For example, the substituted arylthio groups include 3-methylphenylthio, 4-methylnaphthylthio and 2-methylbiphenylthio.

Preferable R1-R5 Substituent Groups

In the above Formulas I and II, each of R5 and R1-R4 that are not represented by Formula II is preferably hydrogen, cyano, nitro, substituted or unsubstituted C1-20 alkyl, substituted or unsubstituted C2-C10 alkenyl, substituted or unsubstituted C3-C7 cycloalkyl, substituted or unsubstituted C4-C7 cycloalkenyl, substituted or unsubstituted aryl, substituted or unsubstituted heteroaryl, substituted or unsubstituted C1-C20 alkoxy, substituted or unsubstituted aryloxy, substituted or unsubstituted C1-C20 alkylamine, substituted or unsubstituted arylamine, substituted or unsubstituted alkylarylamine, substituted or unsubstituted C1-C20 alkylsilyl; substituted or unsubstituted arylsilyl; substituted or unsubstituted alkylarylsilyl, substituted or unsubstituted C1-C20 alkylboranyl, substituted or unsubstituted arylboranyl, substituted or unsubstituted alkylarylboranyl, substituted or unsubstituted C1-C20 alkylthio, or substituted or unsubstituted arylthio. In the foregoing groups, the substituted R1-R5 are preferably substituted with cyano; nitro; formyl; C1-C20 alkyl, namely, methyl, ethyl or proply; aryl, namely, phenyl, naphthyl, biphenyl or anthracenyl; heteroaryl, namely, imidazolyl, thiazolyl, oxazolyl, thiophenyl, pyridyl, pyrimidyl or pyrrolyl; C4-C7 cycloalkenyl, namely, cyclobutenyl or cyclopetenyl; C1-C20 alkoxy, namely, methoxy, ethoxy or propoxy; aryloxy, namely, phenoxy or naphthoxy; C1-C20 alkylamine, namely, methylamine, ethylamine or propylamine; arylamine, namely, phenylamine or naphthylamine; alkylarylamine, namely, methylphenylamine, ethylphenylamine or ethylnaphthylamine; C1-C20 alkylboranyl, namely, dimethylboranyl, diethylboranyl or dipropylboranyl; arylboranyl, namely, diphenylboranyl, dinaphthylboranyl or phenylnaphthylboranyl; alkylarylboranyl, namely, phenylmethylboranyl, naphthylmethylboranyl or naphthylethylboranyl; C1-C20 alkylsilyl, namely, trimethylsilyl, triethylsilyl or tripropylsilyl; arylsilyl, namely, triphenylsilyl or trinaphthylsilyl; alkylarylsilyl, namely, dimethylphenylsilyl, diethylphenylsilyl or diphenylmethylsilyl; C1-C20 alkylthio, namely, methylthio, ethylthio, propylthio or butylthio; and arylthio, namely, phenylthio or naphthylthio.

As for R1-R5, the unsubstituted C1-C20 alkyl group is preferably methyl, ethyl, propyl, butyl, more preferably methyl or ethyl. The substituted C1-C20 alkyl group is preferably isopropyl, n-butyl, t-butyl, isobutyl, n-pentyl, neo-pentyl or n-hexyl, more preferably isopropyl or t-butyl.

The unsubstituted C2-C10 alkenyl group is preferably ethenyl, propenyl, butenyl, pentenyl or hexenyl, more preferably ethenyl or propenyl. The substituted C2-C10 alkenyl group is preferably 2-methyl-ethenyl, 2-methyl-propenyl, 2-methyl-butenyl, 2-methyl-pentenyl or 2-methyl-hexenyl, more preferably 2-methyl-ethenyl or 2-methyl-propenyl.

The unsubstituted or substituted C3-C7 cycloalkyl and C4-C7 cycloalkenyl groups are preferably 5-6 membered, optionally benzo-fused, unsubstituted or substituted, saturated or unsaturated heterocyclic rings. The unsubstituted heterocyclic rings are preferably imidazolyl, thiazolyl, oxazolyl, thiophenyl, pyridyl, pyrimidyl or pyrrolyl, more preferably imidazolyl, thiazolyl or oxazolyl. The substituted heterocyclic rings are preferably 2-methylimidazolyl, 2-methylthiazolyl, 2-methyloxazolyl, 2-methylthiophenyl, 2-methylpyridyl, 2-methylpyrimidyl or 2-methylpyrrolyl, more preferably 2-methylimidazolyl, 2-methylthiazolyl or 2-methyloxazolyl.

The unsubstituted aryl group is preferably phenyl, naphthyl, anthracenyl, biphenyl, terphenyl, double-spiro structures defined in U.S. patent application Ser. No. 10/099,781, which is hereby incorporated herein by reference or tetracenyl, more preferably phenyl or naphthyl. The substituted aryl group is preferably 3-methyl-phenyl, 4-methyl-naphthyl, 9-methyl-anthracenyl or 4-methyl-tetracenyl, more preferably 3-methyl-phenyl or 4-methyl-naphthyl.

The unsubstituted heteroaryl group is preferably imidazolyl, oxazolyl, thiazolyl, furanyl, thiophenyl, pyrazolyl, pyridyl or pyrimidinyl, more preferably imidazolyl, oxazolyl or thiazolyl. The substituted heteroaryl group is preferably 2-methyl-imidazolyl, 2-methyl-oxazolyl, 2-methyl-thiazolyl, 2-methyl-furanyl, 2-methyl-thiophenyl, 2-methyl-pyrazolyl, 2-methyl-pyridyl or 2-methyl-pyrimidinyl, more preferably 2-methyl-imidazolyl, 2-methyl-oxazolyl or 2-methyl-thiazolyl.

The unsubstituted C1-C20 alkoxy group is preferably methoxy, ethoxy, propoxy, butoxy, pentoxy or hexoxy, more preferably methoxy or ethoxy. The substituted C1-C20 alkoxy group is preferably isopropoxy, isobutoxy, t-butoxy or neo-pentoxy, more preferably isopropoxy or isobutoxy.

The unsubstituted aryloxy group is preferably phenoxy, naphthoxy or biphenoxy, more preferably phenoxy or naphthoxy. The substituted aryloxy group is preferably 3-methyl-phenoxy, 4-methyl-naphthoxy or 2-methyl-biphenoxy, more preferably 3-methyl-phenoxy or 4-methyl-naphthoxy.

The unsubstituted C1-C20 alkylamine group is preferably methylamine, ethylamine, propylamine, butylamine, pentylamine, hexylamine or heptylamine, more preferably methylamine or ethylamine. The substituted C1-C20 alkylamine group is preferably isopropylamine, isobutylamine, t-butylamine, 2-pentylamine or neo-pentylamine, more preferably isopropylamine, isobutylamine or t-butylamine.

The unsubstituted arylamine group is preferably phenylamine, naphthylamine, biphenylamine or anthracenylamine, more preferably phenylamine or naphthylamine. The substituted arylamine group is preferably 3-methyl-phenylamine, 4-methyl-naphthylamine, 2-methyl-biphenylamine or 9-methyl-anthracenylamine, more preferably 3-methyl-phenylamine or 4-methyl-naphthylamine.

The unsubstituted alkylarylamine group is preferably phenylmethylamine, phenylethylamine, naphthylmethylamine, naphthylethylamine or biphenylmethylamine, more preferably phenylmethylamine, phenylethylamine or naphthylmethylamine. The substituted alkylarylamine group is preferably 3-methyl-phenylmethylamine, phenyl(isopropyl)amine, naphthyl(isopropyl)amine, naphthyl(isobutyl)amine or biphenyl(isopropyl)amine, more preferably 3-methyl-phenylmethylamine or phenylisopropylamine.

The unsubstituted C1-C20 alkylsilyl group is preferably trimethylsilyl, triethylsilyl, or tributylsilyl, more preferably trimethylsilyl or triethylsilyl. The substituted C1-C20 alkylsilyl group is preferably tri(isopropyl)silyl, tri(isobutyl)silyl, tri(t-butyl)silyl or tri(2-butyl)silyl, more preferably tri(isopropyl)silyl or tri(isobutyl)silyl.

The unsubstituted arylsilyl group is preferably triphenylsilyl, trinaphthylsilyl or tribiphenylsilyl, more preferably triphenylsilyl or trinaphthylsilyl. The substituted arylsilyl group is preferably tri(3-methylphenyl)silyl, tri(4-methylnaphthyl)silyl or tri(2-methylbiphenyl)silyl, more preferably tri(3-methylphenyl)silyl or tri(4-methylnaphthyl)silyl.

The unsubstituted alkylarylsilyl group is preferably phenylmethylsilyl, phenylethylsilyl, naphthylmethylsilyl, naphthylethylsilyl or biphenylmethylsilyl, more preferably phenylmethylsilyl or phenylethylsilyl. The substituted alkylarylsilyl group is preferably 3-methyl-phenylmethylsilyl, phenyl(isopropyl)silyl, naphthyl(isopropyl)silyl, naphthyl(isobutyl)silyl or biphenyl(isopropyl)silyl, more preferably 3-methyl-phenylmethylsilyl or phenylisopropylsilyl.

The unsubstituted C1-C20 alkylboranyl group is preferably dimethylboranyl, diethylboranyl, dipropylamine, dibutylamine or dipentylamine, more preferably dimethylboranyl or diethylboranyl. The substituted C1-C20 alkylboranyl group is preferably di(isopropyl)boranyl, di(isobutyl)boranyl, di(t-butyl)boranyl or (isopropyl)(isobutyl)amine, more preferably di(isopropyl)boranyl or di(isobutyl)boranyl.

The unsubstituted arylboranyl group is preferably diphenylboranyl, dinaphthylboranyl or dibiphenylboranyl, more preferably diphenylboranyl or dinaphthylboranyl. The substituted arylboranyl group is preferably di(3-methylphenyl)boranyl, di(4-methylnaphthyl)boranyl or di(2-methylbiphenyl)boranyl, more preferably di(3-methylphenyl)boranyl or di(4-methylnaphthyl)boranyl.

The unsubstituted alkylarylboranyl group is preferably phenylmethylboranyl, phenylethylboranyl, naphthylmethylboranyl, naphthylethylboranyl or biphenylmethylboranyl, more preferably phenylmethylboranyl or phenylethylboranyl. The substituted alkylarylboranyl group is preferably 3-methyl-phenylmethylboranyl, phenyl(isopropyl)boranyl, naphthyl(isopropyl)boranyl, naphthyl(isobutyl)boranyl or biphenyl(isopropyl)boranyl, more preferably 3-methyl-phenylmethylboranyl or phenyl(isopropyl)boranyl.

The unsubstituted C1-C20 alkylthio group is preferably methylthio, ethylthio, propylthio, butylthio, pentylthio or hexylthio, more preferably methylthio or ethylthio. The substituted C1-C20 alkylthio group is preferably tri(isopropyl)thio, tri(isobutyl)thio, tri(t-butyl)thio or tri(2-butyl)thio, more preferably tri(isopropyl)thio or tri(isobutyl)thio.

The unsubstituted arylthio group is preferably phenylthio, naphthylthio or biphenylthio, more preferably phenylthio or naphthylthio. The substituted arylthio group is preferably (3-methylphenyl)thio, (4-methylnaphthyl)thio or (2-methylbiphenyl)thio, more preferably (3-methylphenyl)thio or (4-methylnaphthyl)thio.

Preferably, the substituent groups for R5 and R1-R4, when these groups are other than Formula II, are straight chain C1-C20 alkyl groups and the following groups:

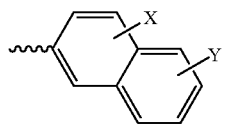

Formula 1-1

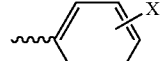

Formula 1-2

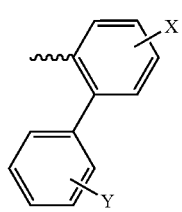

Formula 1-3

-continued

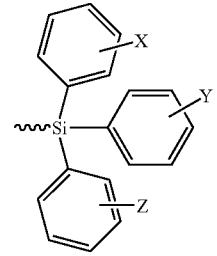

Formula 1-4

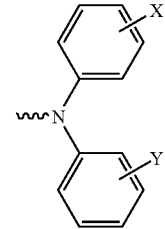

Formula 1-5

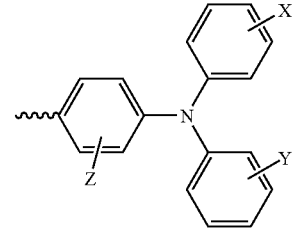

Formula 1-6

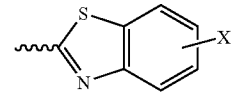

Formula 1-7

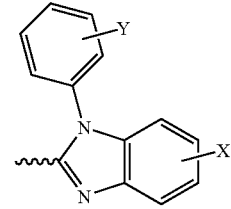

Formula 1-8

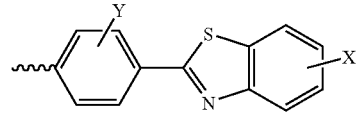

Formula 1-9

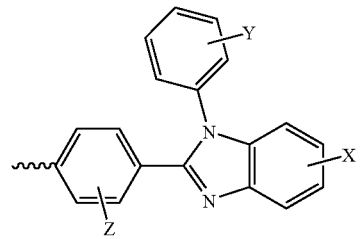

Formula 1-10

-continued

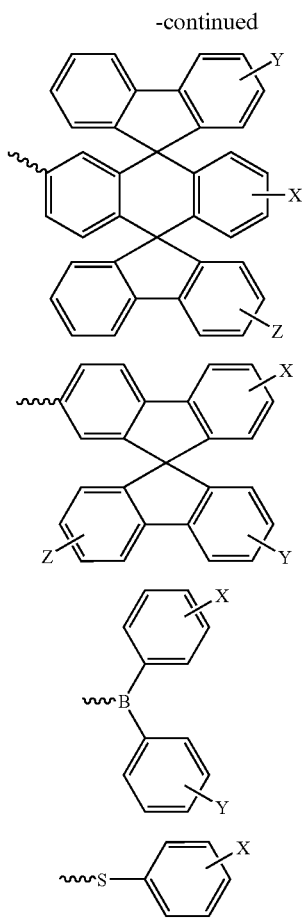

Formula 1-11

Formula 1-12

Formula 1-13

Formula 1-14

When one or more of R1-R4 are represented by Formula II, they are preferably:

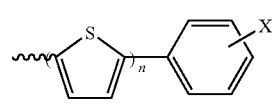

Formula 2-1

-continued

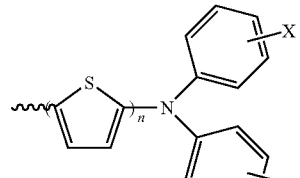

Formula 2-2

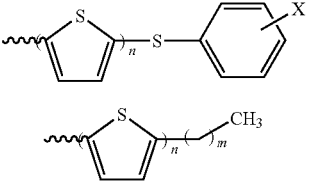

Formula 2-3

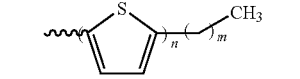

Formula 2-4

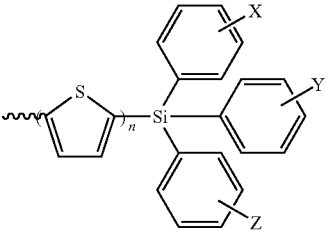

Formula 2-5

In the above-listed Formulas, X, Y and Z refer to substituent groups, which may be identical to or different from one another. Each ring moiety where X, Y or Z is attached may be substituted with more than one, identical or different, substituent groups like X, Y or Z. X, Y and Z are cyano, nitro, formyl, substituted or unsubstituted C1-C20 alkyl, aryl, heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio or arylthio. Preferably, X, Y and Z are chosen from cyano, nitro, methyl, ethyl, isopropyl, t-butyl, methoxy, ethoxy, propoxy, methylthio, imidazolyl, pyridyl, thiazolyl, oxazolyl, furanyl, thiophenyl, pyrrolyl, pyridyl or pyrimidyl.

Examples of compounds within Formula I include:

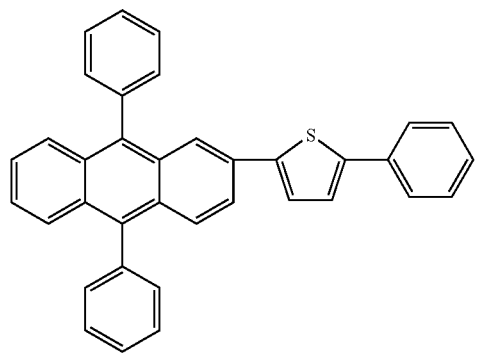

Compound 1

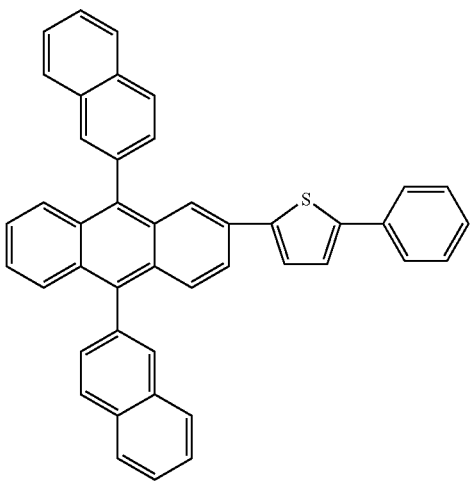

Compound 2

-continued
Compound 3
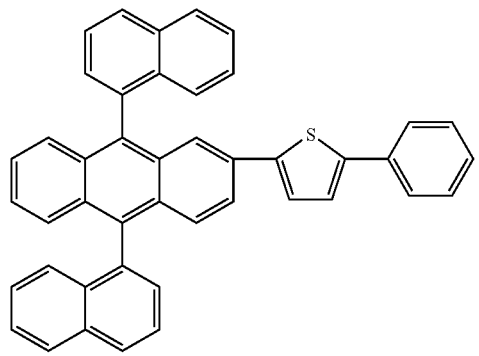
Compound 4
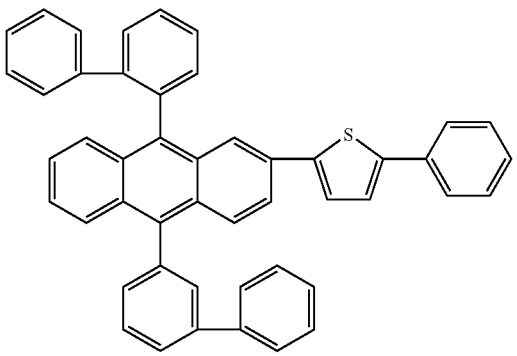
Compound 5
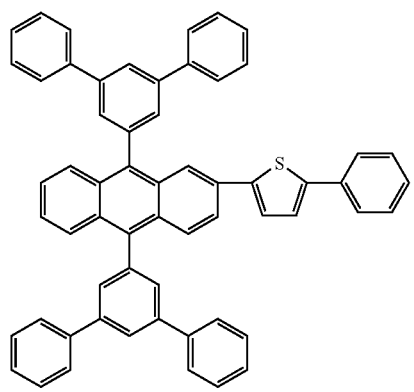
Compound 6
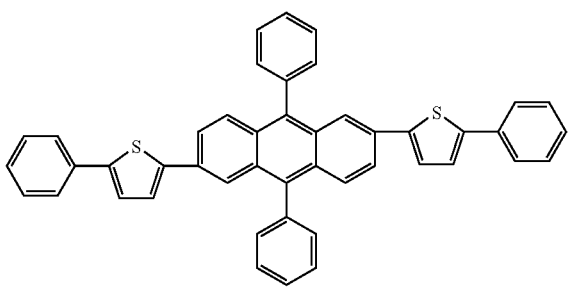
Compound 7
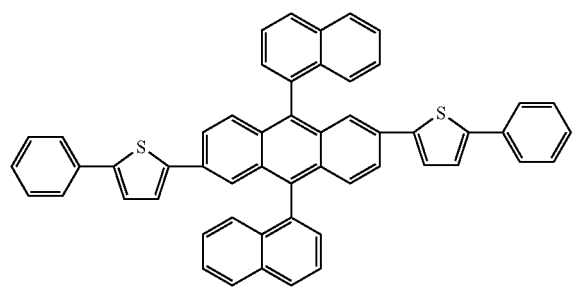
Compound 8
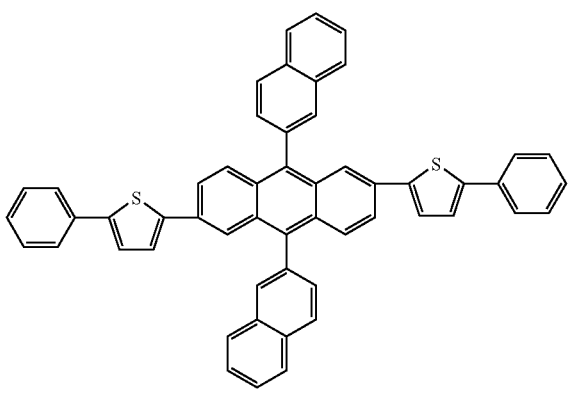
Compound 9
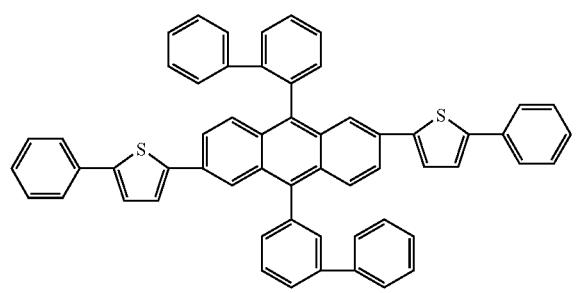
Compound 10
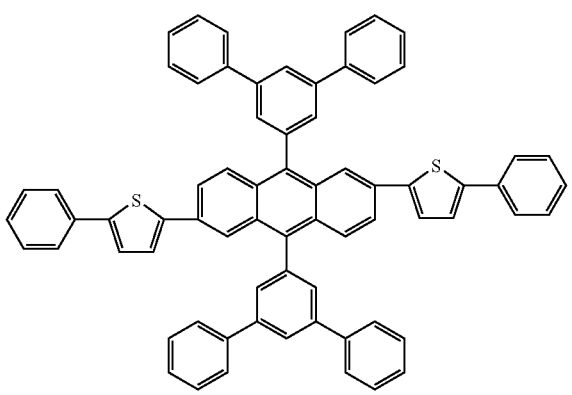

Compound 11
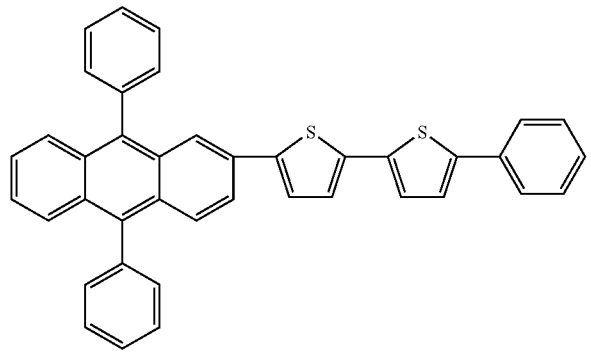
Compound 12
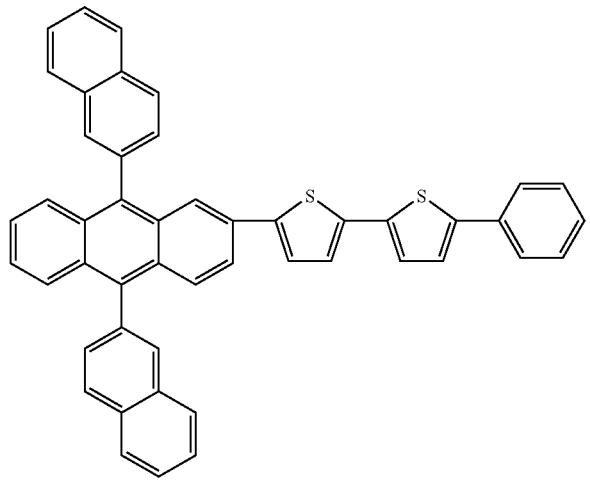
Compound 13
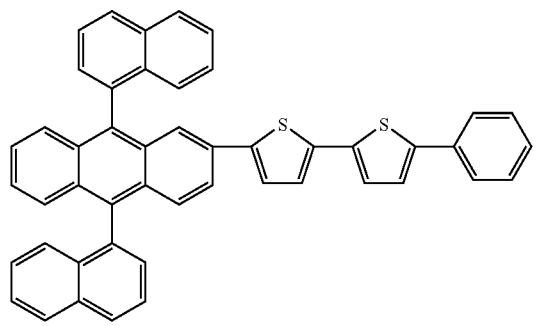
Compound 14
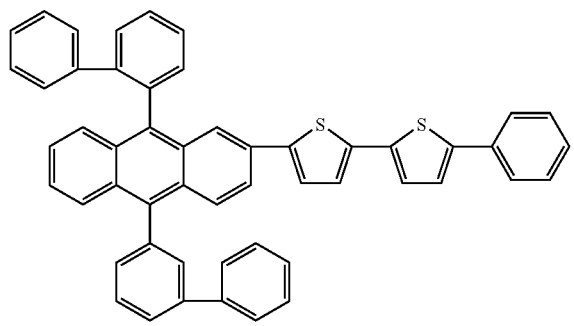
Compound 15
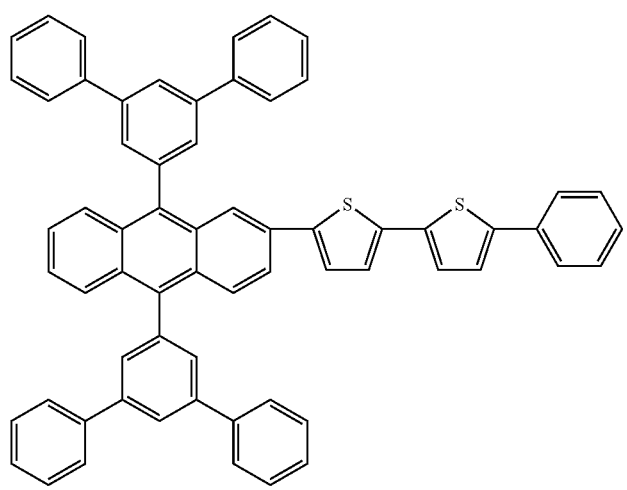

Compound 16
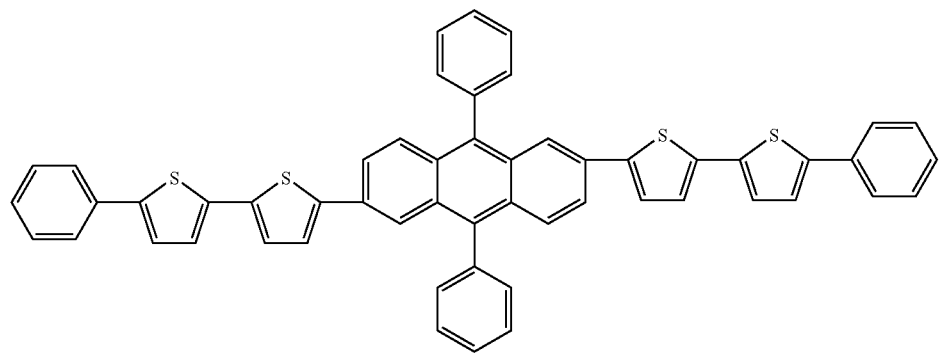
Compound 17
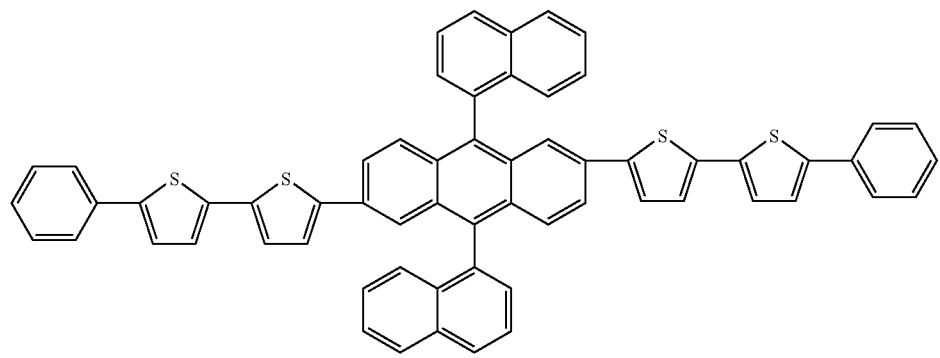
Compound 18
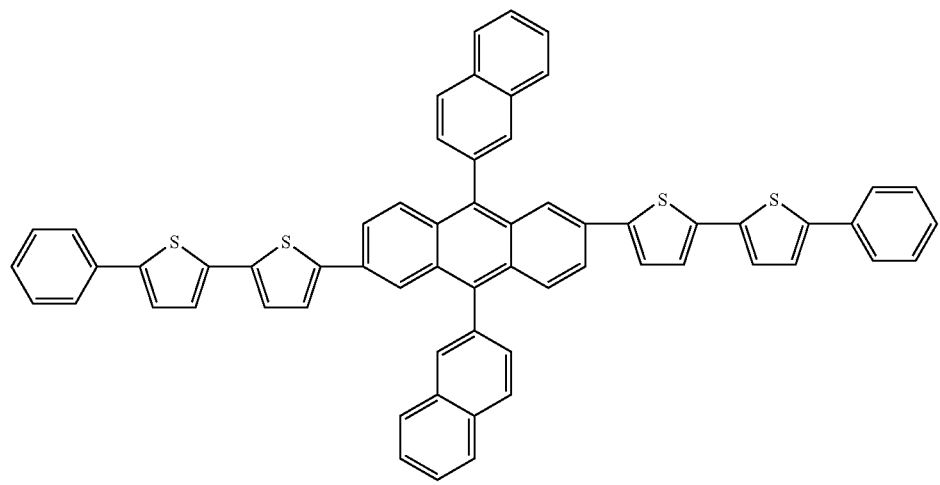
Compound 19
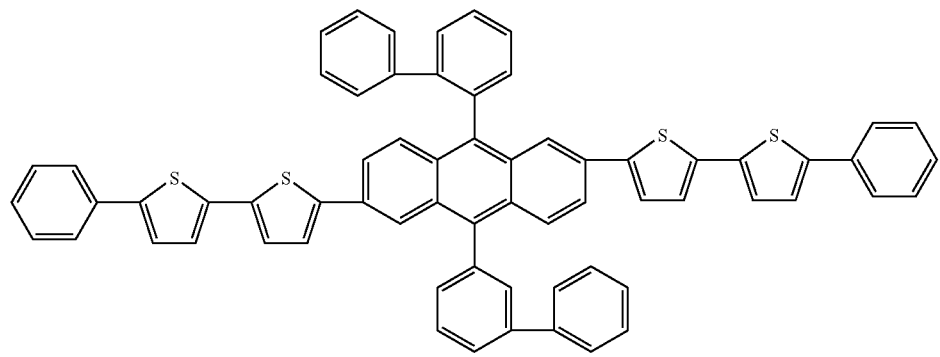

-continued
Compound 20
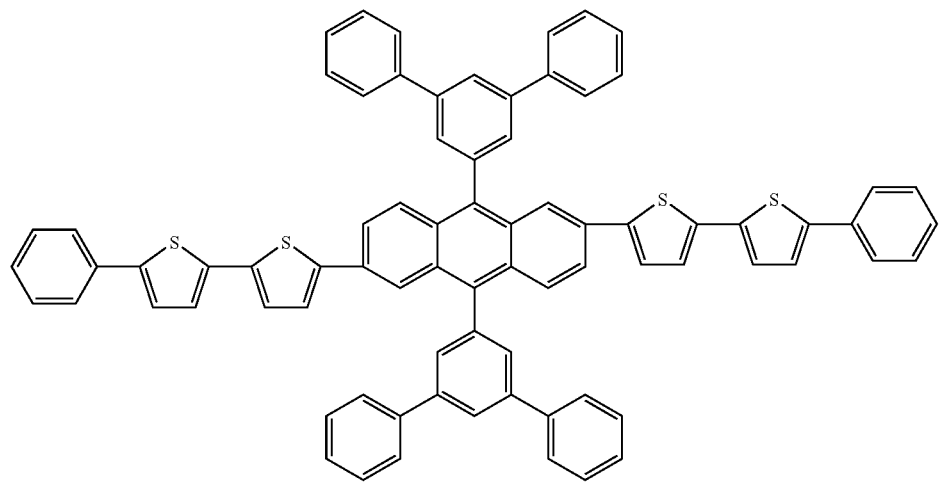
Compound 21
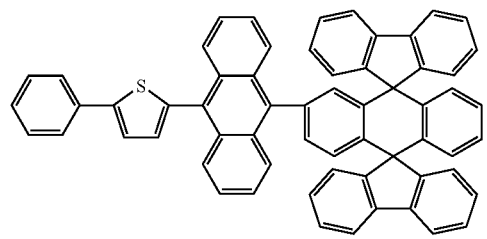
Compound 22
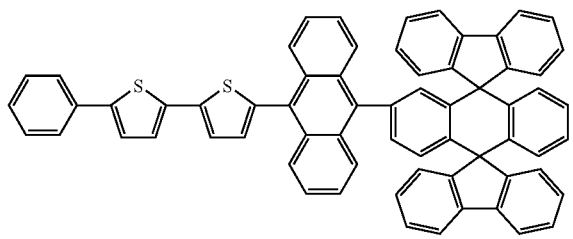
Compound 23
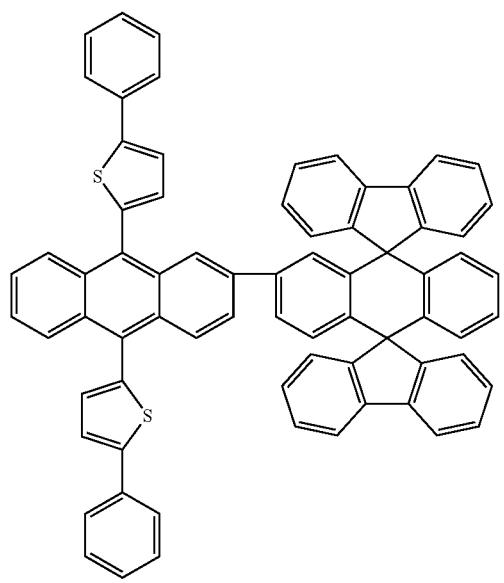

-continued
Compound 24
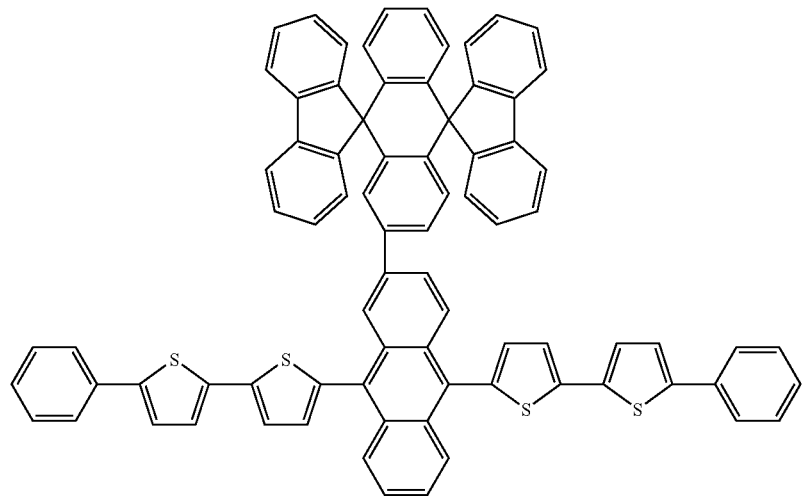
Compound 25
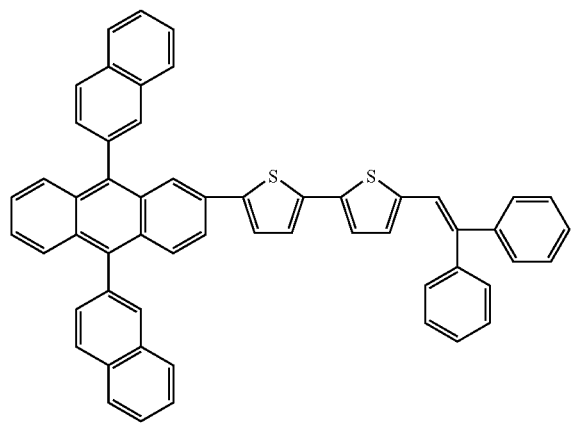
Compound 26
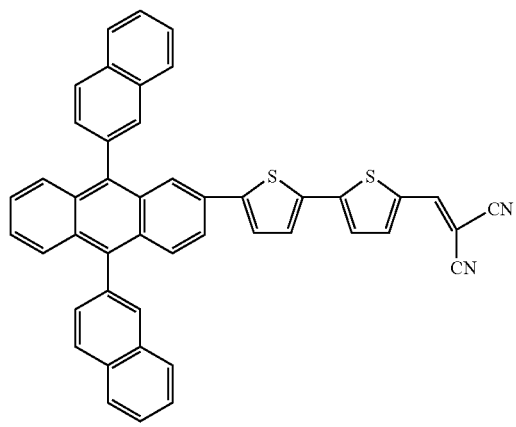
Compound 27
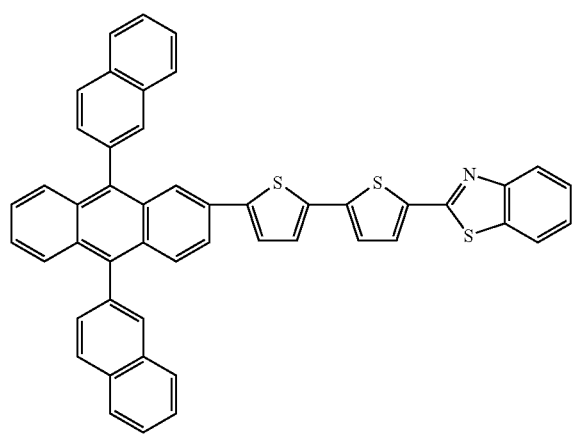
Compound 28
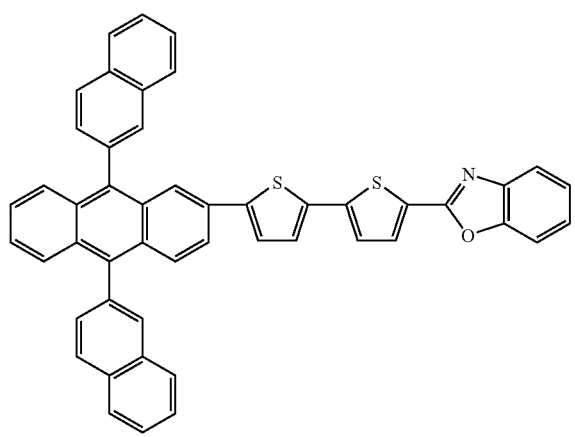

-continued
Compound 29
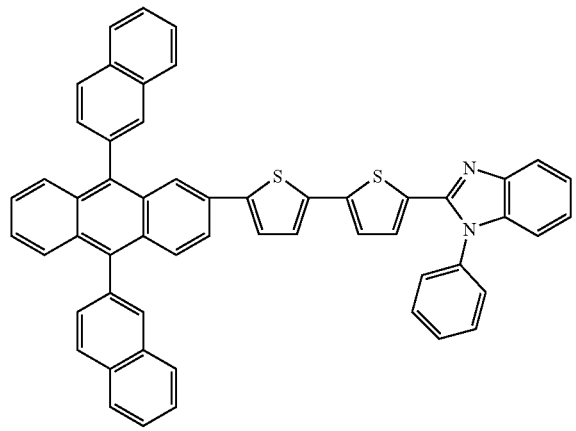
Compound 30
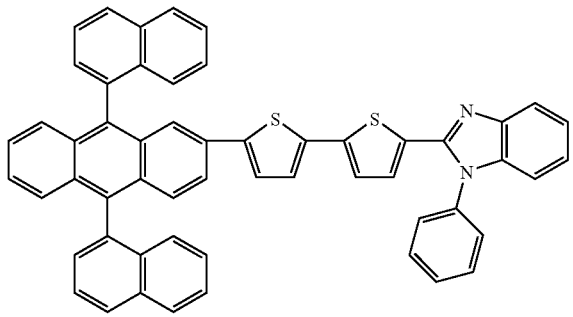
Compound 31
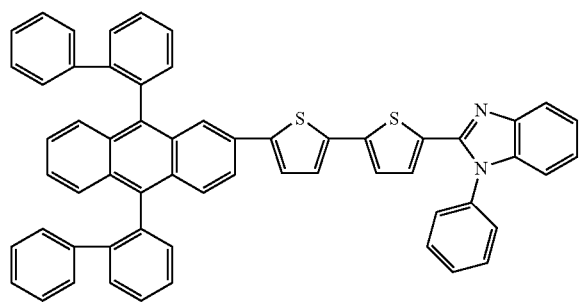
Compound 32
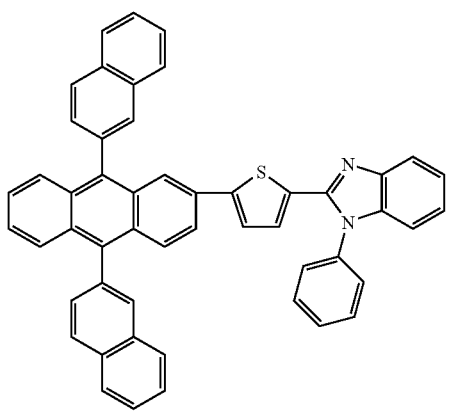
Compound 33
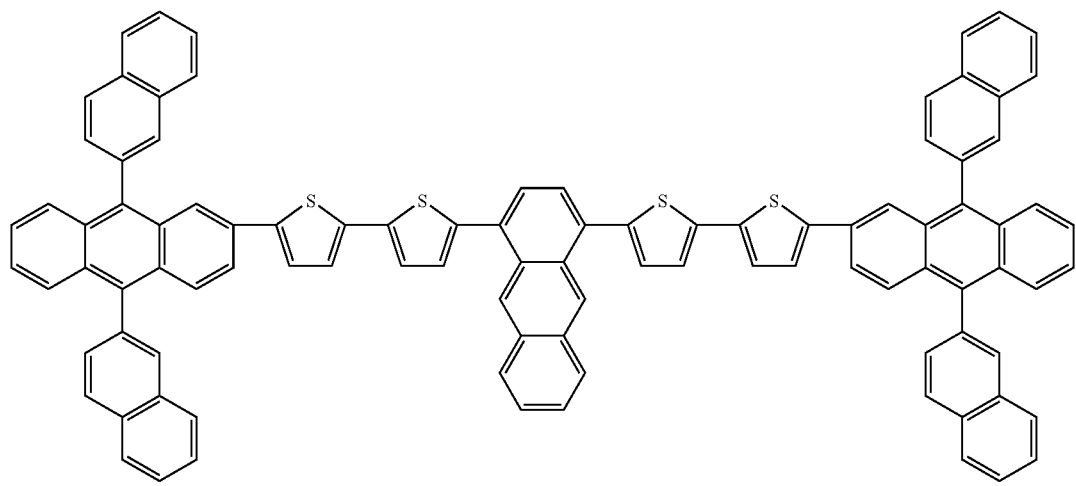

-continued
Compound 34
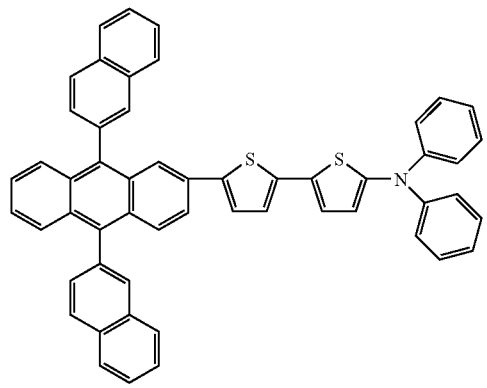
Compound 35
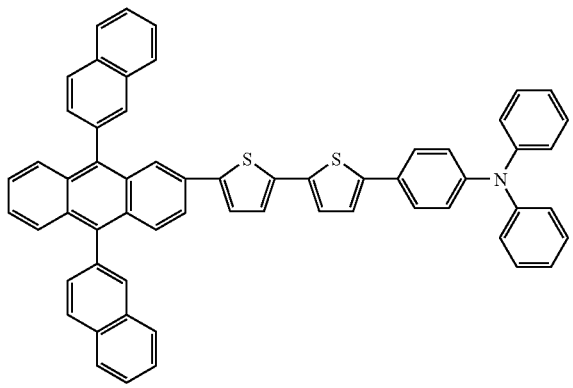
Compound 36
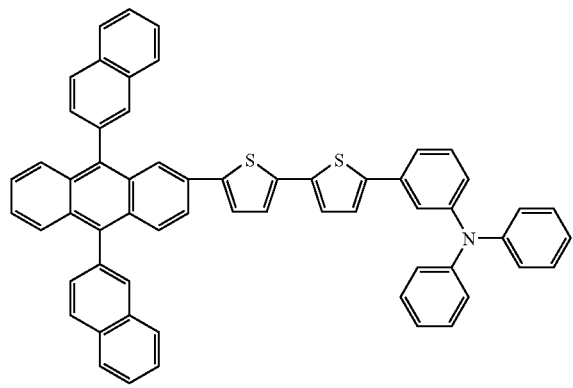
Compound 37
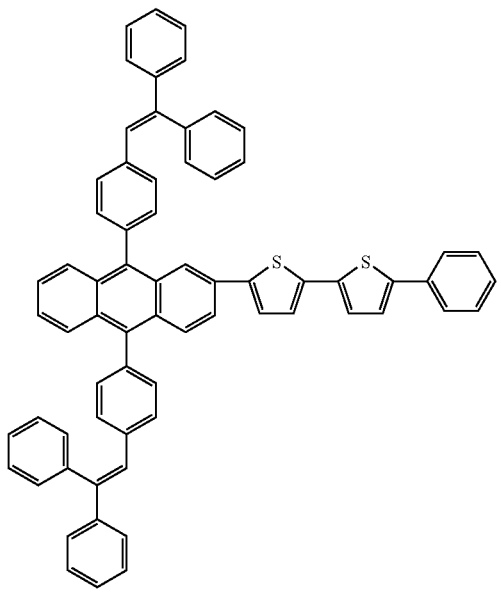
compound 38
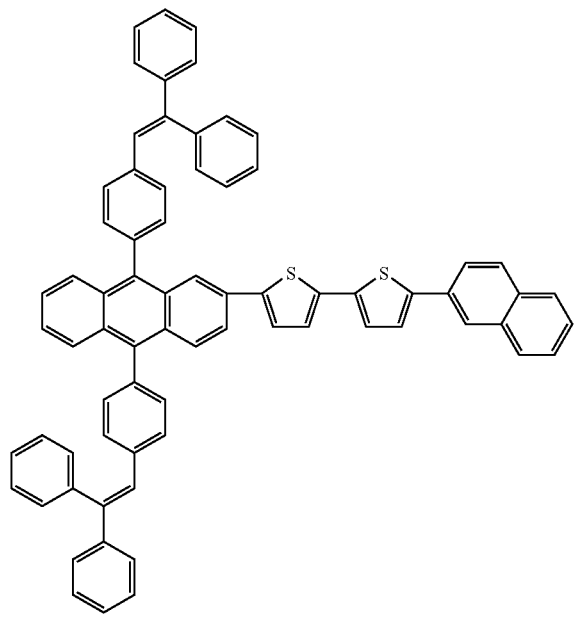
Compound 39
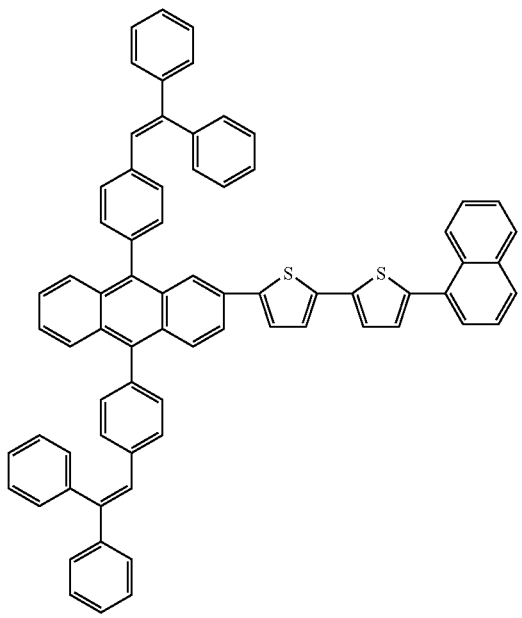

-continued
Compound 40
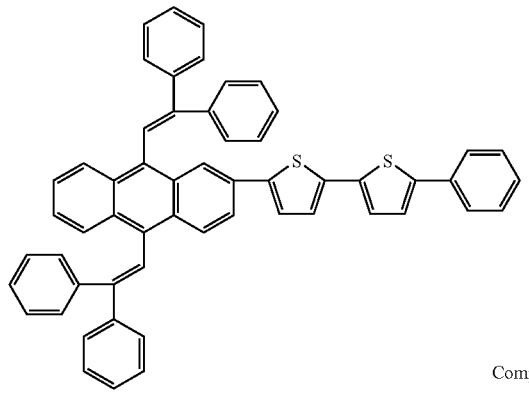
Compound 41
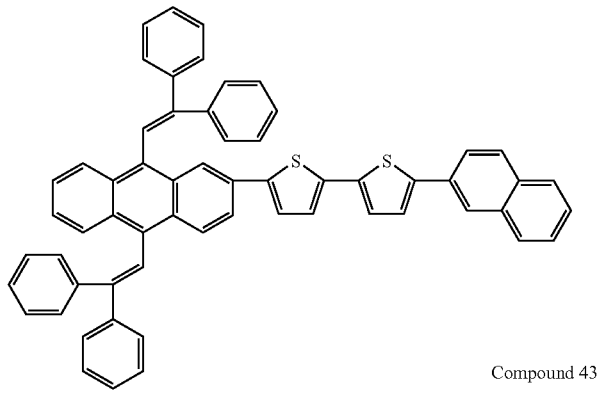
Compound 42
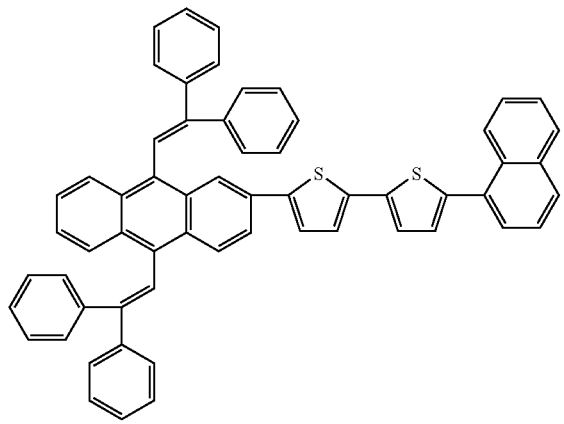
Compound 43
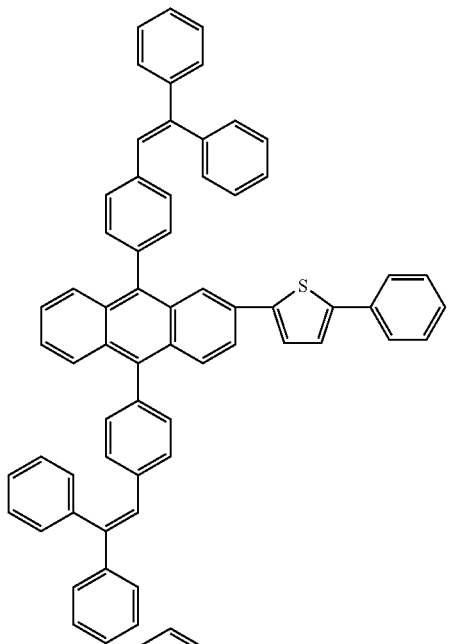
Compound 44
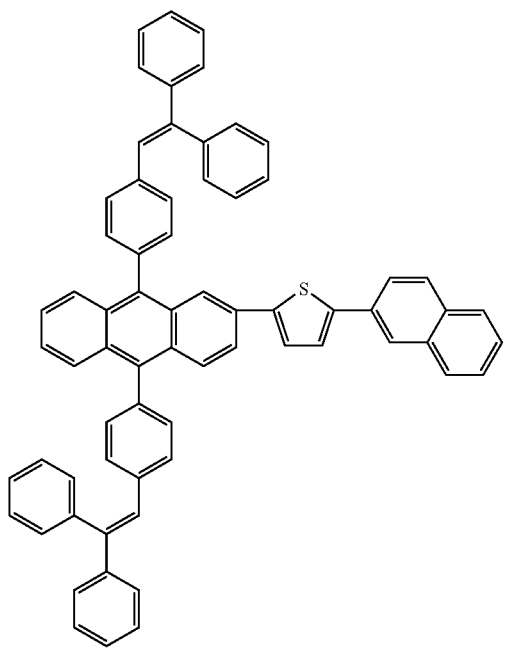
Compound 45
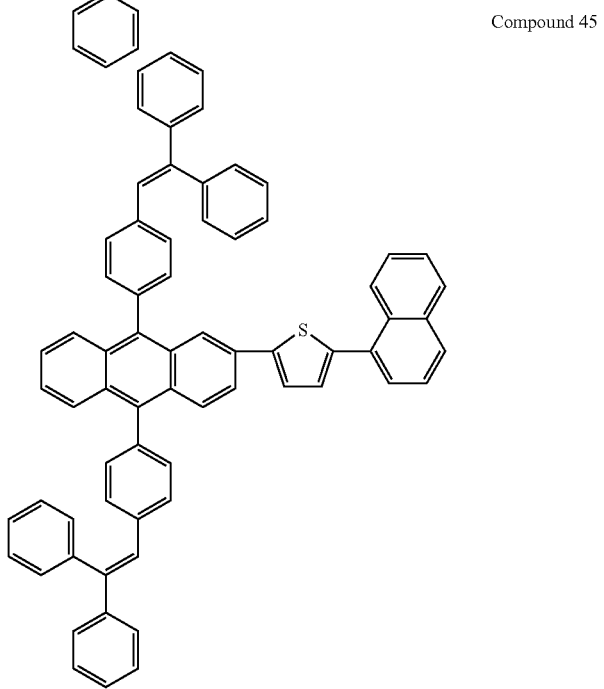

-continued
Compound 46
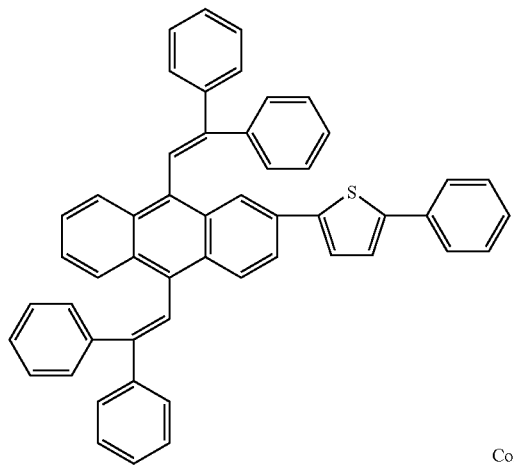
Compound 47
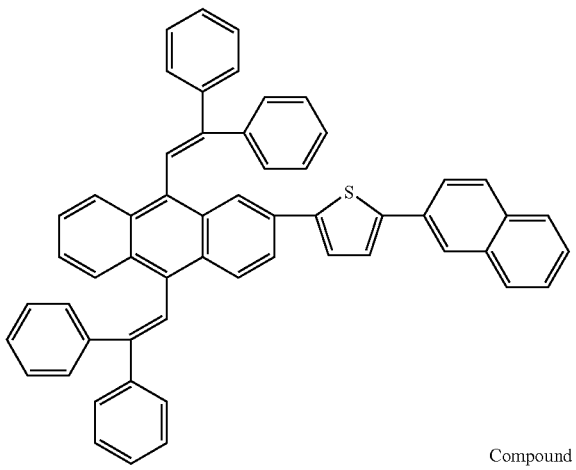
Compound 48
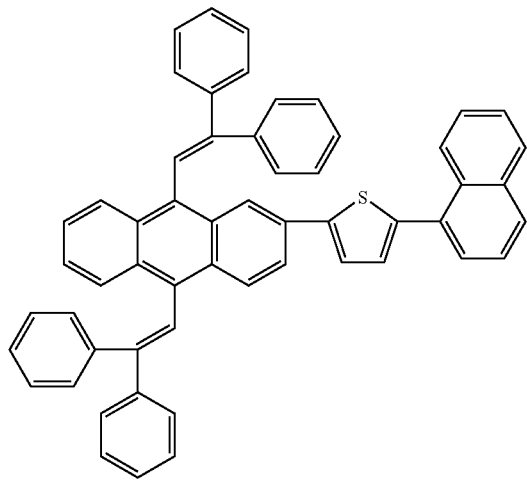
Compound 49
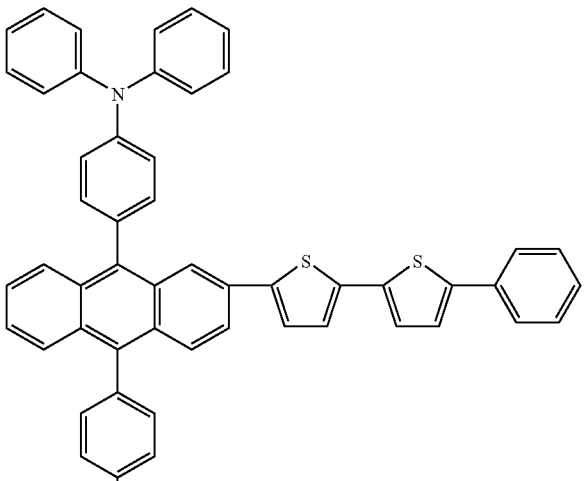
Compound 50
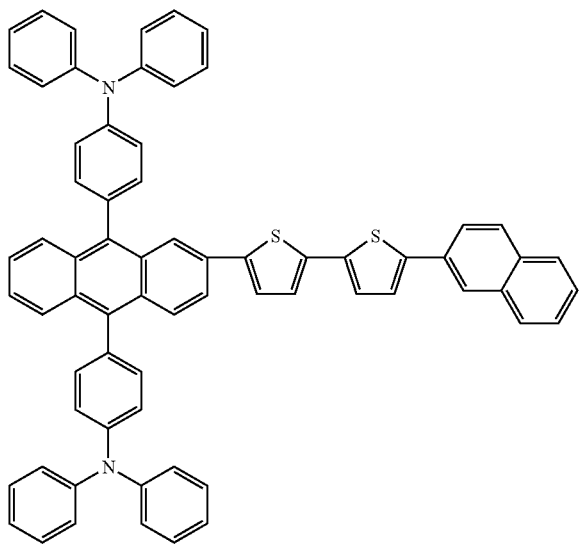
Compound 51
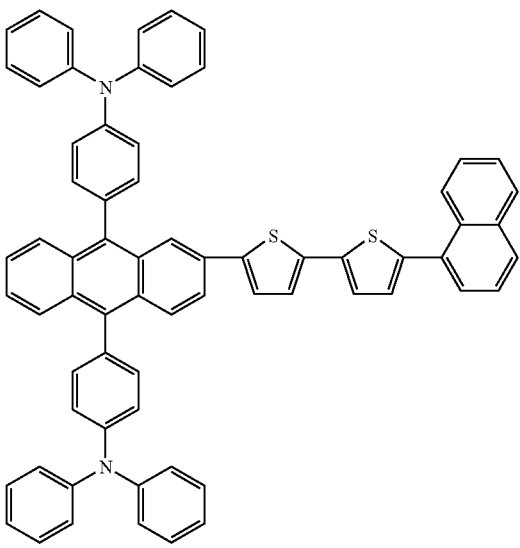

-continued
Compound 52
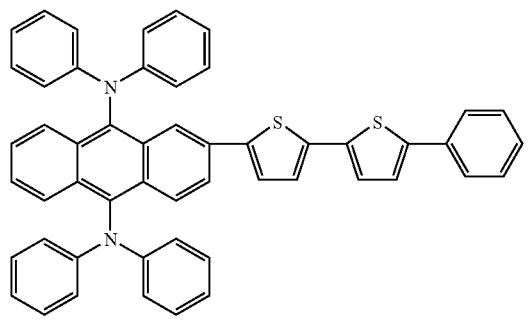
Compound 53
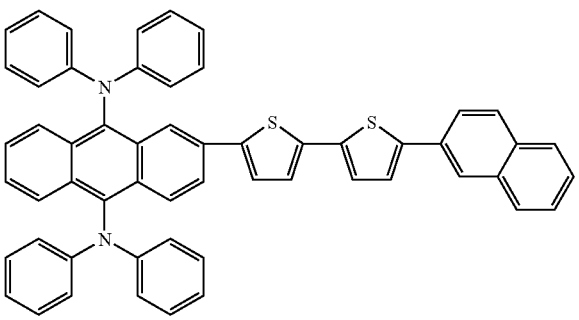
Compound 54
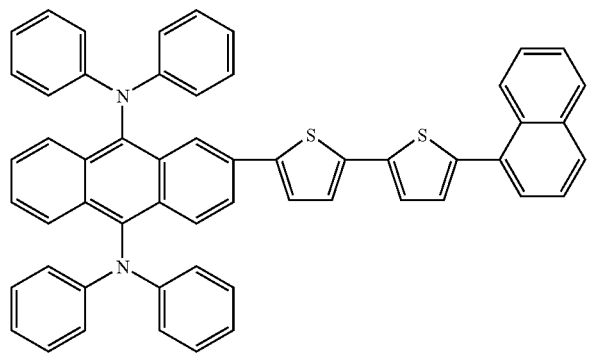
Compound 55
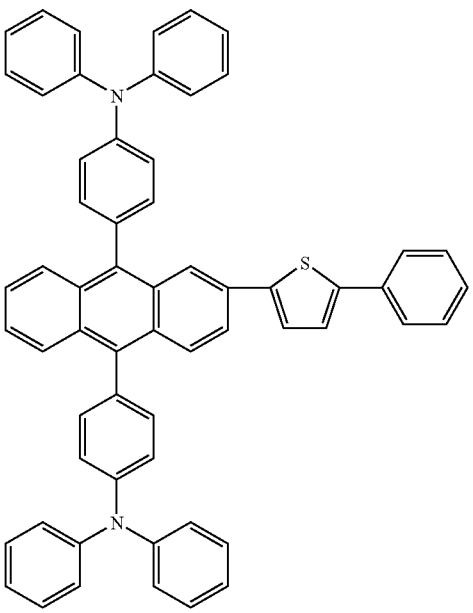
Compound 56
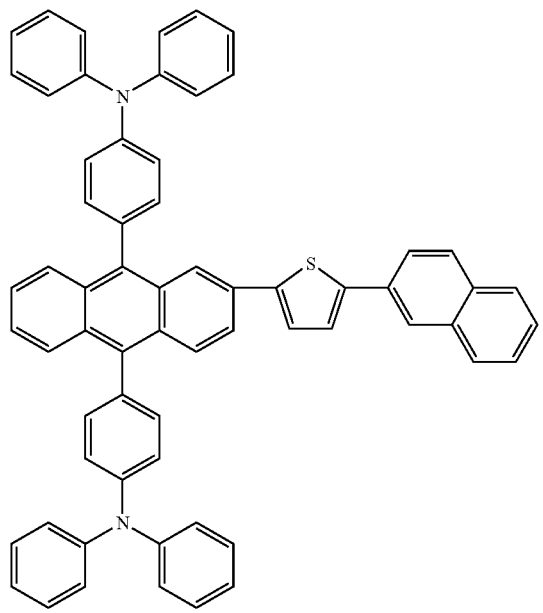
Compound 57
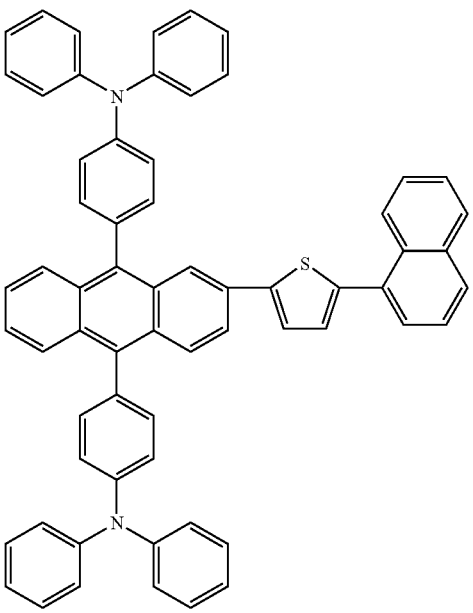

-continued
Compound 58
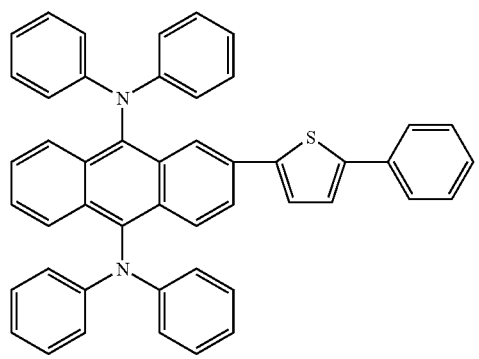
Compound 59
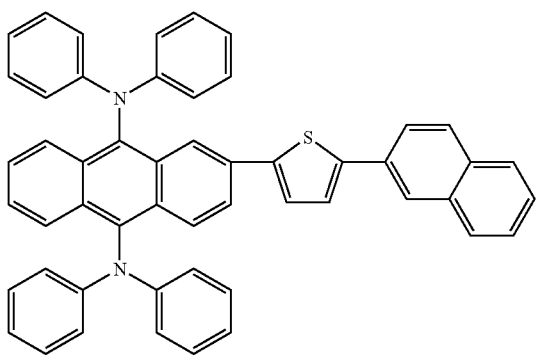
Compound 60
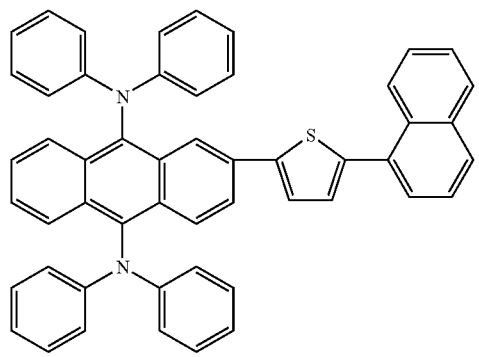
Compound 61
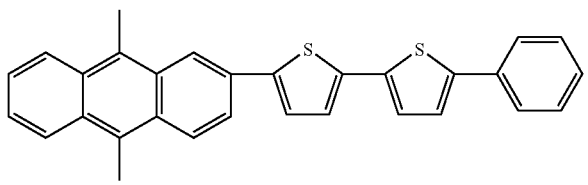
Compound 62
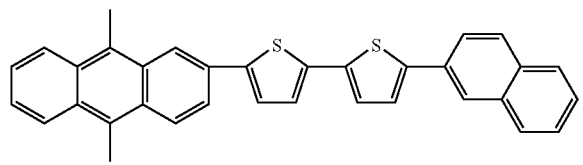
Compound 63
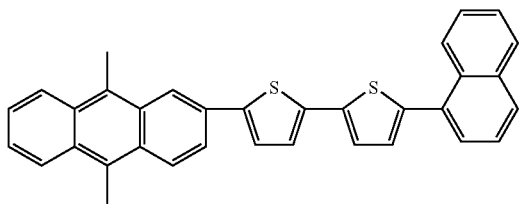
Compound 64
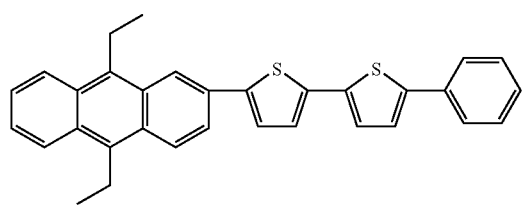
Compound 65
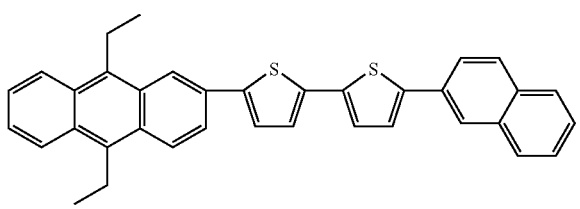
Compound 66
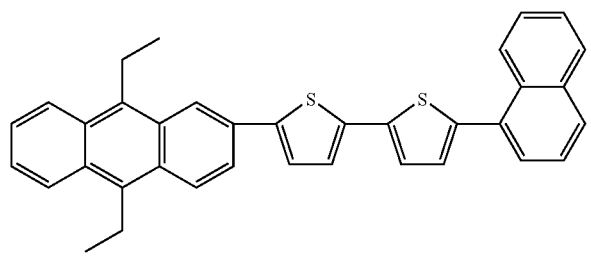
Compound 67
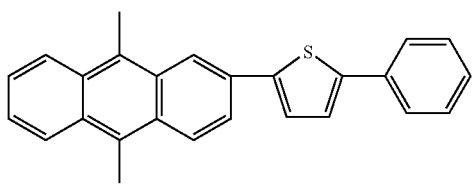

-continued
Compound 68
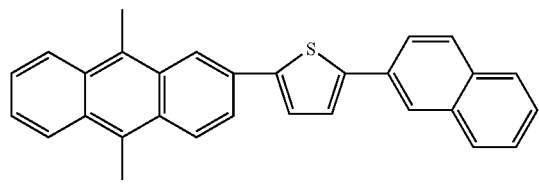
Compound 69
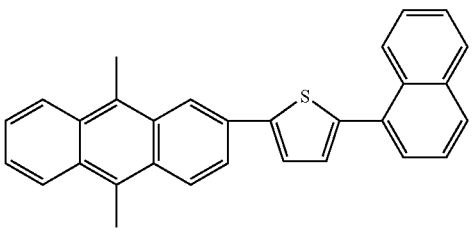
Compound 70
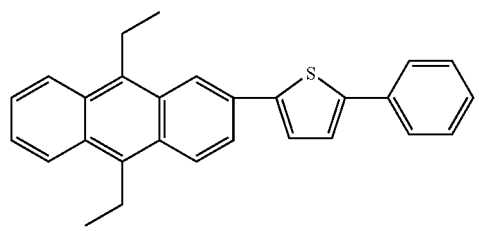
Compound 71
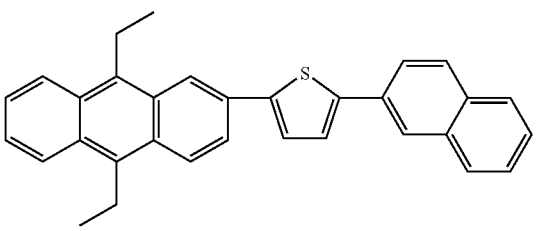
Compound 72
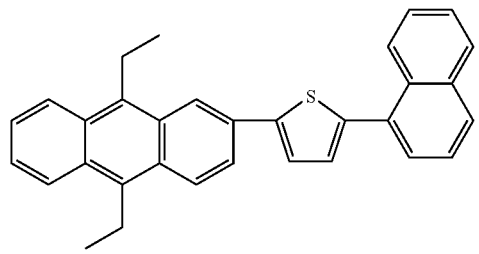
Compound 73
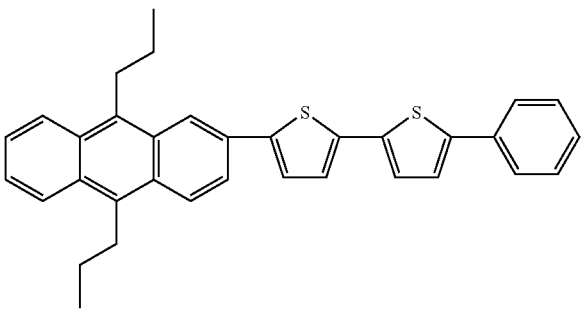
Compound 74
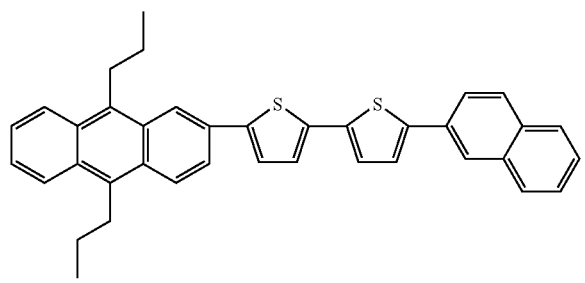
Compound 75
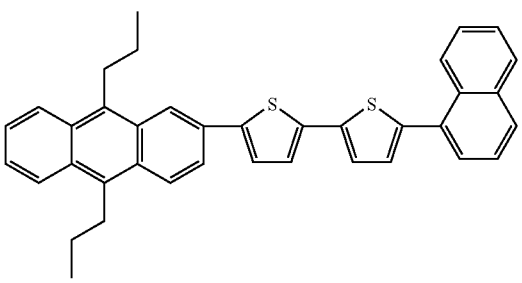
Compound 76
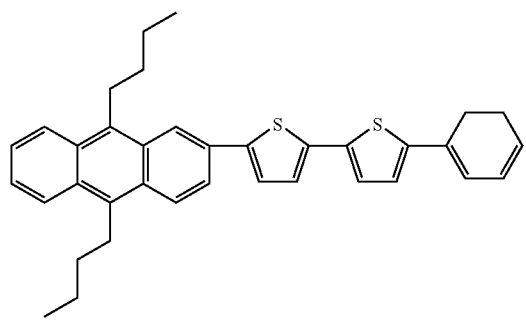
Compound 77
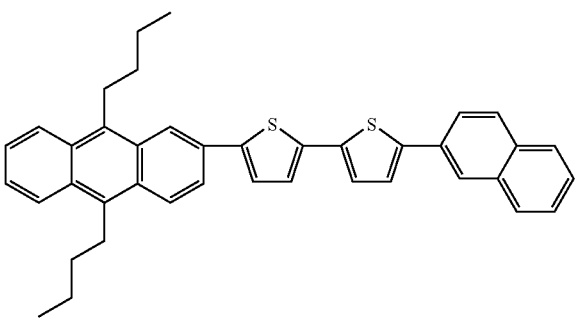

-continued
Compound 78
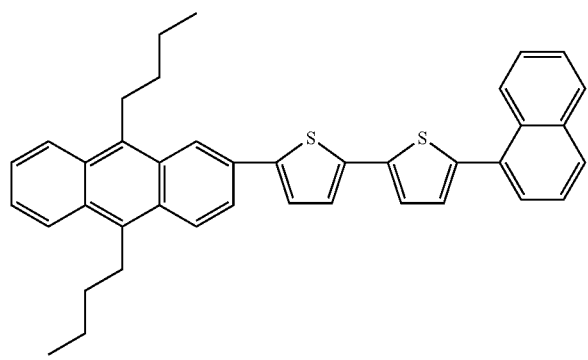
Compound 79
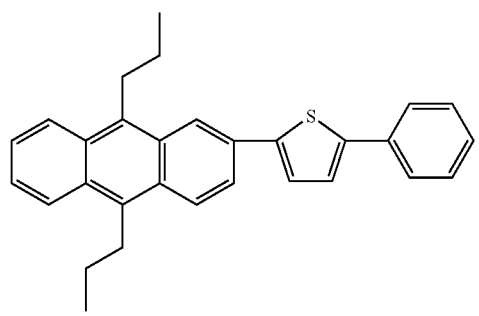
Compound 80
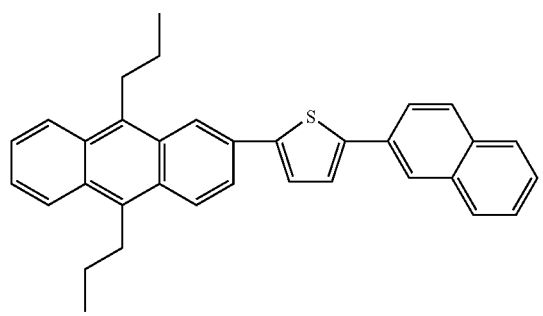
Compound 81
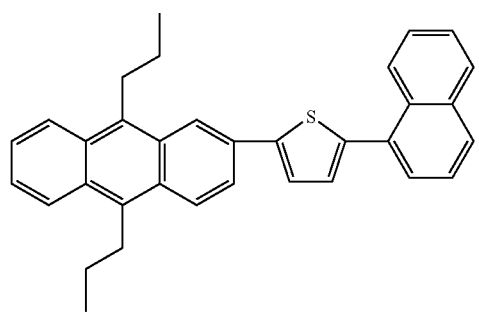
Compound 82
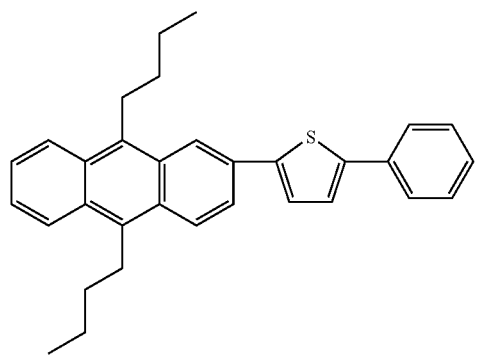
Compound 83
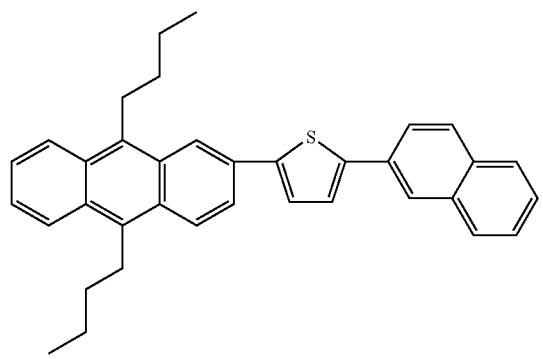
Compound 84
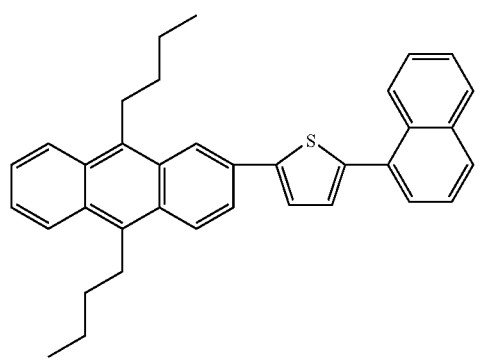
Compound 85
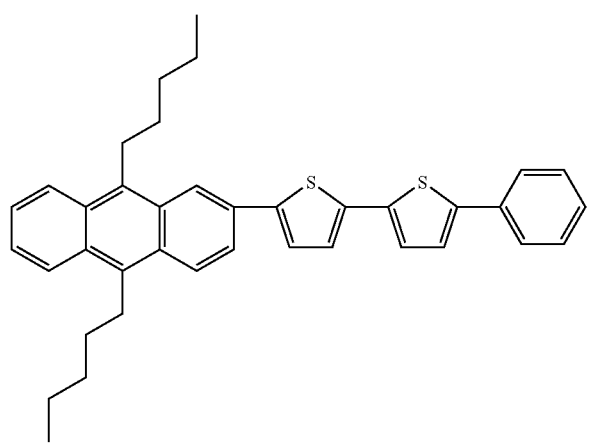

Compound 86
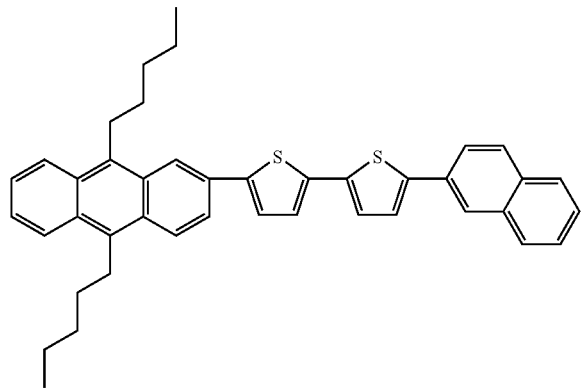
Compound 87
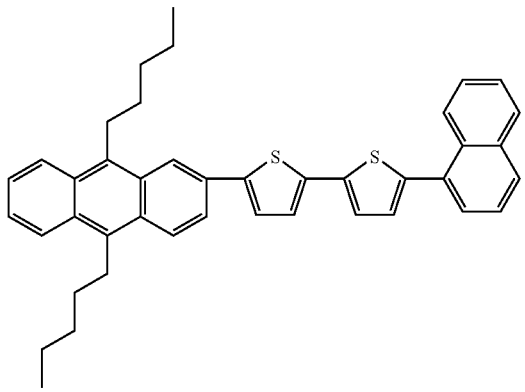
Compound 88
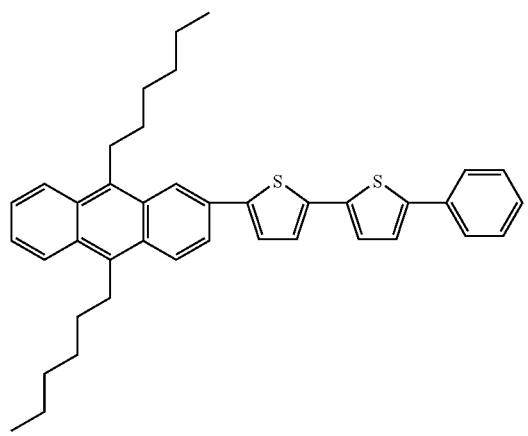
Compound 89
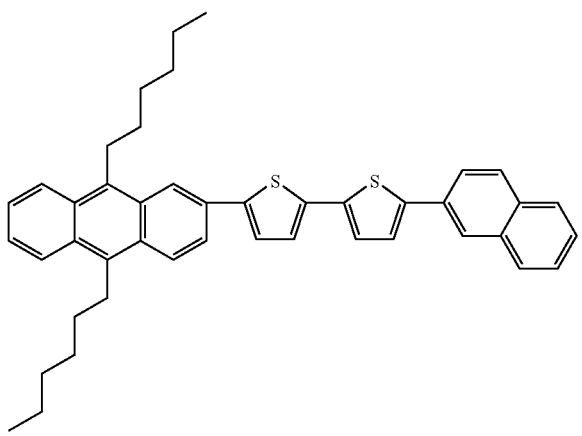
Compound 90
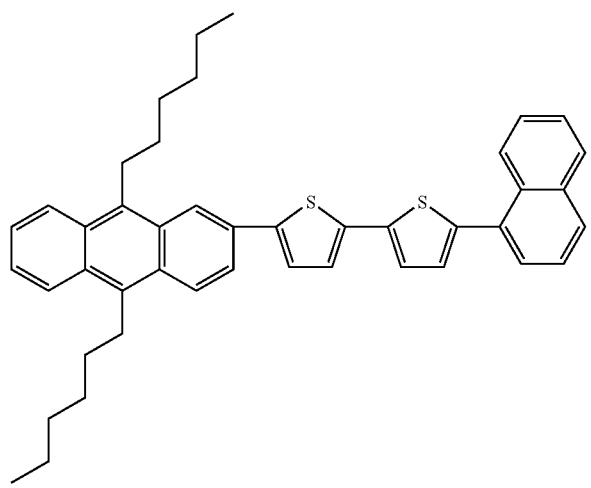
Compound 91
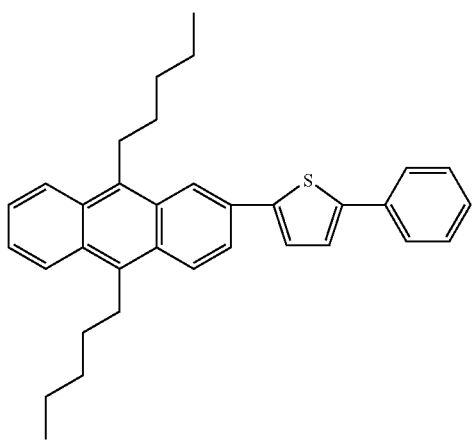

Compound 92

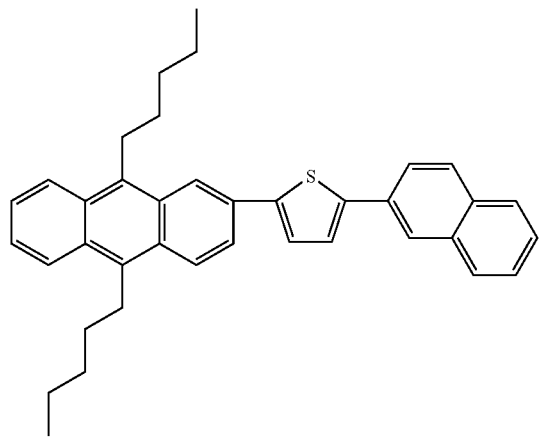

Compound 93

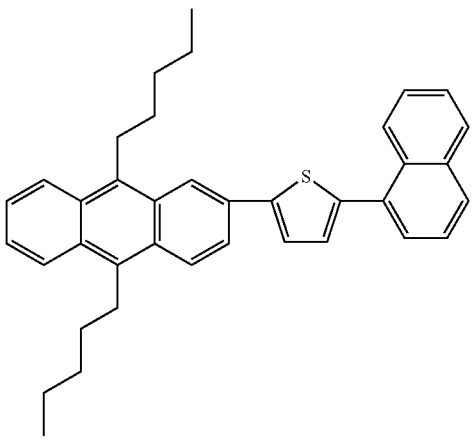

Compound 94

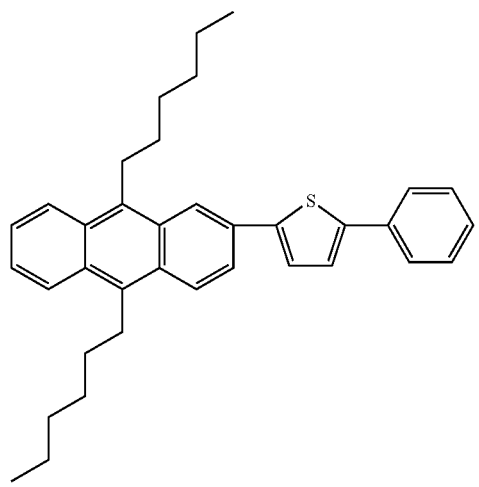

Compound 95

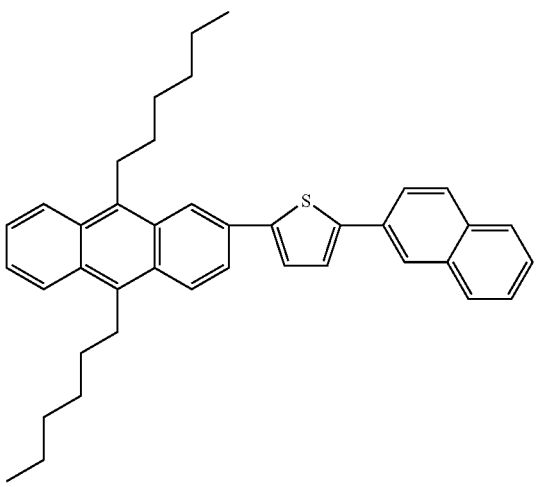

Compound 96

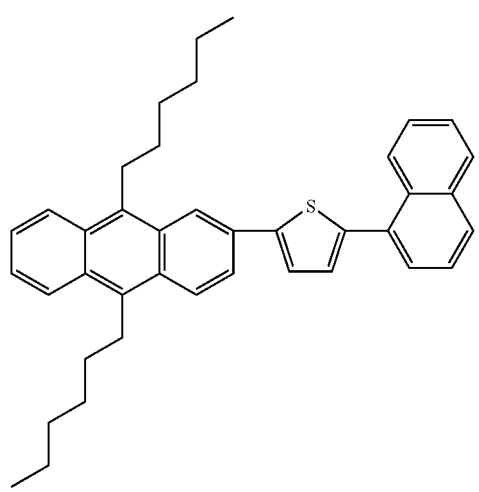

Synthesis of the New Organic Compounds

The compounds satisfying Formula I can be synthesized in multi-step chemical reactions. The syntheses of the compounds are described by way of actual examples below. As will be clear in the examples, the certain intermediate compounds are first synthesized, and then the intermediate compounds are reacted together and/or modified. Some exemplary intermediate compounds are listed below as Compounds 101-123. In these compounds, "Br" may be substituted with any other reactive atoms or functional groups.

Compound 101
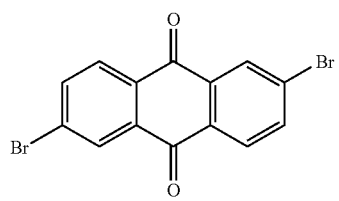
Compound 102
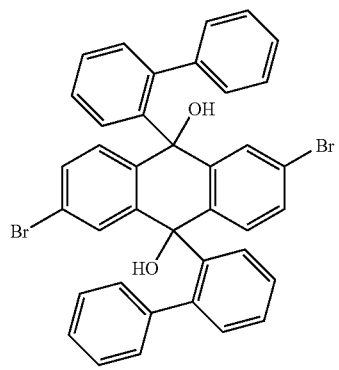
Compound 103
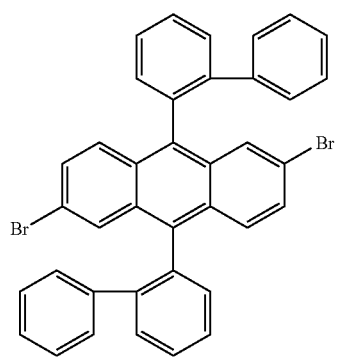
Compound 104
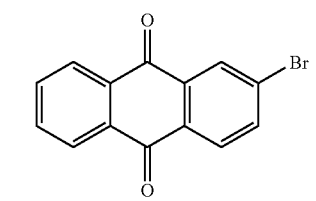
Compound 105
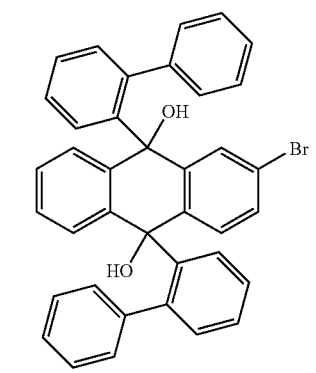
-continued
Compound 106
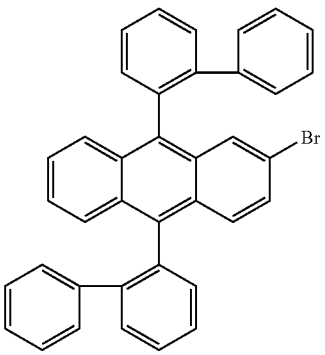
Compound 107
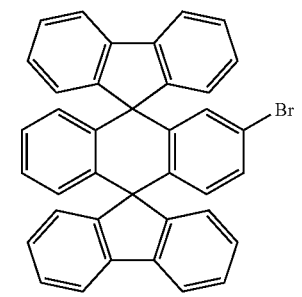
Compound 108
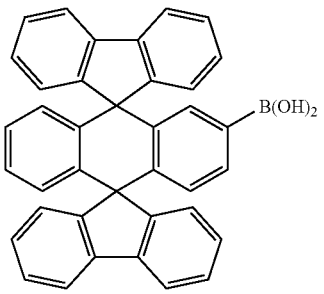
Compound 109
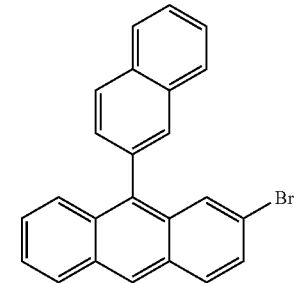
Compound 110
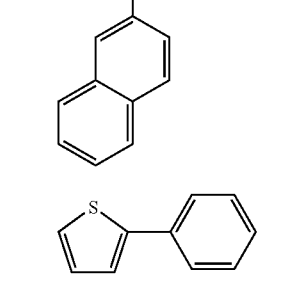
Compound 111
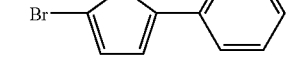

Compound 112, Compound 113, Compound 114, Compound 115, Compound 116, Compound 117, Compound 118, Compound 119, Compound 120, Compound 121

-continued

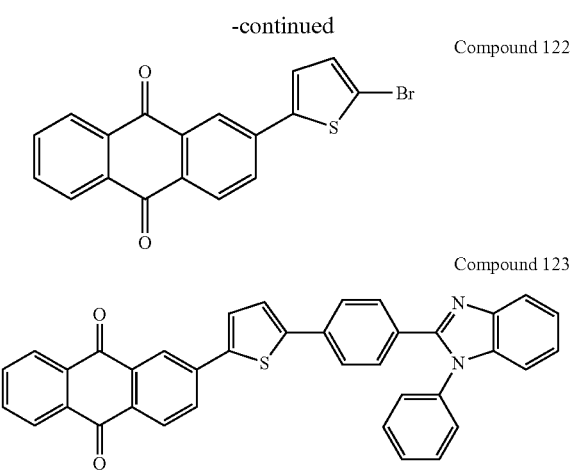

Compound 122

Compound 123

Characteristics and Properties of the New Organic Compounds

Organic EL devices are made of, among other materials, one or more organic compounds. As will be discussed in detail below, the organic compounds used in organic EL devices have various functions, including emission of light, facilitating injection of carriers from electrodes, facilitating transportation of injected carriers, hosting dopants, improving efficiency of light emission, and so forth. Generally, the organic compounds satisfying Formula I according to one aspect of the present invention are compatible with applications in organic EL devices as they can perform one or more of the functions.

Although not limited thereto, many of the compounds satisfying Formula I are particularly useful as a light-emitting material. Further, many of such compounds are suitable as a host for hosting another light-emitting material called dopant. A host material for hosting a light-emitting dopant must have its own light-emitting property. The host material in an organic EL device has to energetically match with the dopant. Further, the host material has to be electrically stable in the organic EL devices.

Electroluminescence of New Compounds

Advantageously, a number of compounds satisfying Formula I have the property of emitting visible light when appropriate energy is applied. These compounds have a band gap, which is difference between the lowest energy level of the conduction band and the highest energy level of the valance band, generally corresponding to the energy for visual light emission. Advantageously, the band gap of the compounds satisfying Formula I range from about 1.8 eV to about 3.0 eV. Advantageously, compounds satisfying Formula I can generate visible light of various colors ranging from generally bluish green to far red upon application of appropriate electric energy. The band gap corresponding to these color ranges are from about 2.8 eV to about 1.8 eV. These light-emitting compounds can host one or more matching dopants as will be further discussed below. Also, these compounds can emit its own colored light either as a sole light-emitting material or as a dopant to another host material.

Energy Matching with Dopant

A host material and a dopant are to energetically match with each other. As will be discussed in a greater detail below, the band gap of the host material is required to be the same or greater than the band gap of the dopant so that the dopant can emit visible light. Further, it is preferred that the band gap of the host is only "slightly" greater than that of the dopant as will be further discussed. A number of the compounds satisfying Formula I advantageously generate colored lights, varying from bluish green to far red. Thus, there are many choices of different color-generating materials for either host or dopant among the compounds satisfying Formula I. For example, when a dopant of a particular band gap is selected, then there would be choices of compounds satisfying Formula I that can energetically match with the dopant, vice versa.

Stability of New Compounds in Organic EL Context

In the process of electroluminescence in an organic EL device, holes and electrons travels around and recombine at light-emitting molecules as will be discussed below. Certain light-emitting molecules are electrically more stable than others. In the case of less stable light-emitting molecules, reactions of holes and electrons at or near the light-emitting molecules may electrochemically destroy or decompose the compounds, which can most likely cause increase of driving voltage of the device, drastic drop in the brightness of the emission or both. Preferably, light-emitting materials, either hosts or dopants, are selected from the electrically stable compounds. The new organic compounds according to one aspect of this invention show outstanding electrical stability as will be discussed below with reference to Examples.

Further, thermal stability of the compounds for use in organic EL devices is also important as quality of organic EL devices may deteriorate when they are subject to a high temperature. Generally, in organic EL devices, organic compounds exist in the form of amorphous thin films. The amorphous form of the compounds may crystallize when the temperature goes up above their glass transition temperature. Even partial crystallization of the compounds may cause an electrical short, resulting in the loss of electroluminescence. Crystallization in the amorphous films may also occur during the manufacturing process involving a high temperature. In order to avoid thermal crystallization of organic compounds, glass transition temperature of a compound must be higher than a temperature to which the thin film could possibly be subjected. Generally, organic EL compounds having a glass transition temperature of about 120° C. or above are sufficient for use in organic EL devices. As glass transition temperature of a compound has good correlation with melting point thereof, as well understood by ordinary skills in the relevant technology, the melting point is often used as a reference instead of glass transition temperature. The relationship between melting point and glass transition temperature is set forth in *Molecular Design for Nonpolymeric Organic Dye Glasses with Thermal Stability*, J. Phys. Chem. 97, 6240-6248 (1993), which is hereby incorporated herein by reference. Advantageously, many compounds of Formula I have melting points sufficient to use in organic EL devices. Preferably, the compounds of Formula I have a melting point above about 300° C. or a glass transition temperature above about 120° C., more preferably, the melting point is above about 350° C.

Organic EL Devices Using New Compounds

Another aspect of the present invention is organic EL devices using the novel organic compounds described above. As mentioned above, the new compounds have one or more properties of electroluminescence, hole injection, hole transportation, electron transportation and electron injection. Various organic EL devices can be constructed with one or more of the new organic compounds of the present invention in combination with any other compounds compatible with organic EL technology.

Figure 2:
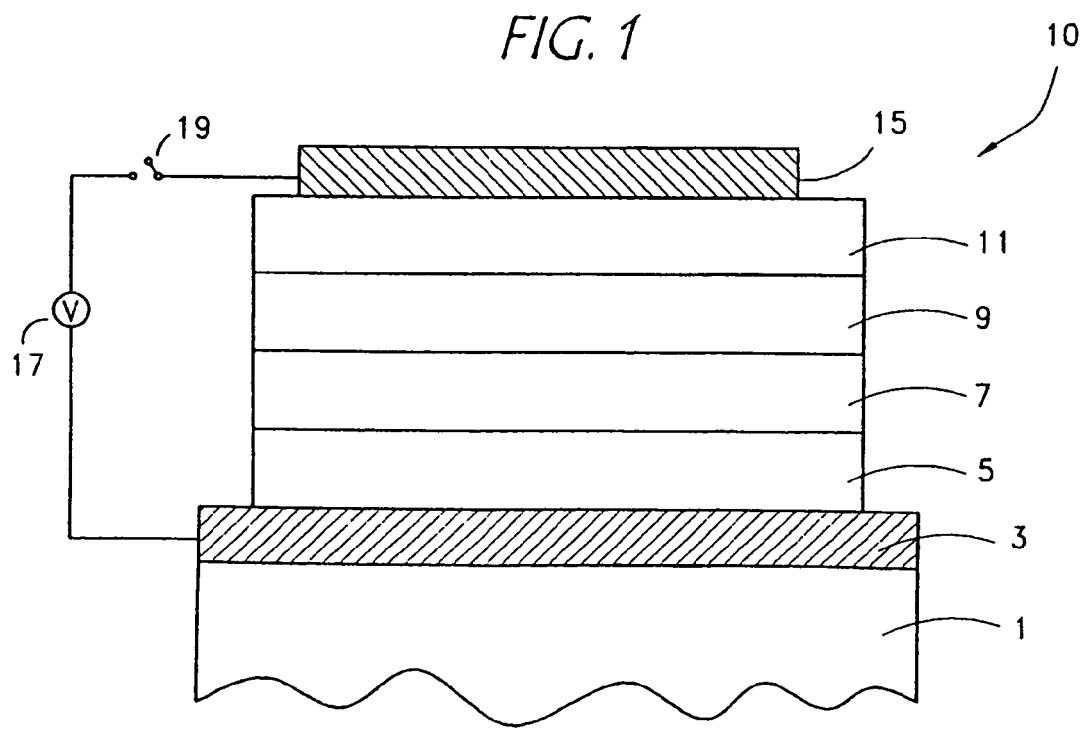
Figure 3:
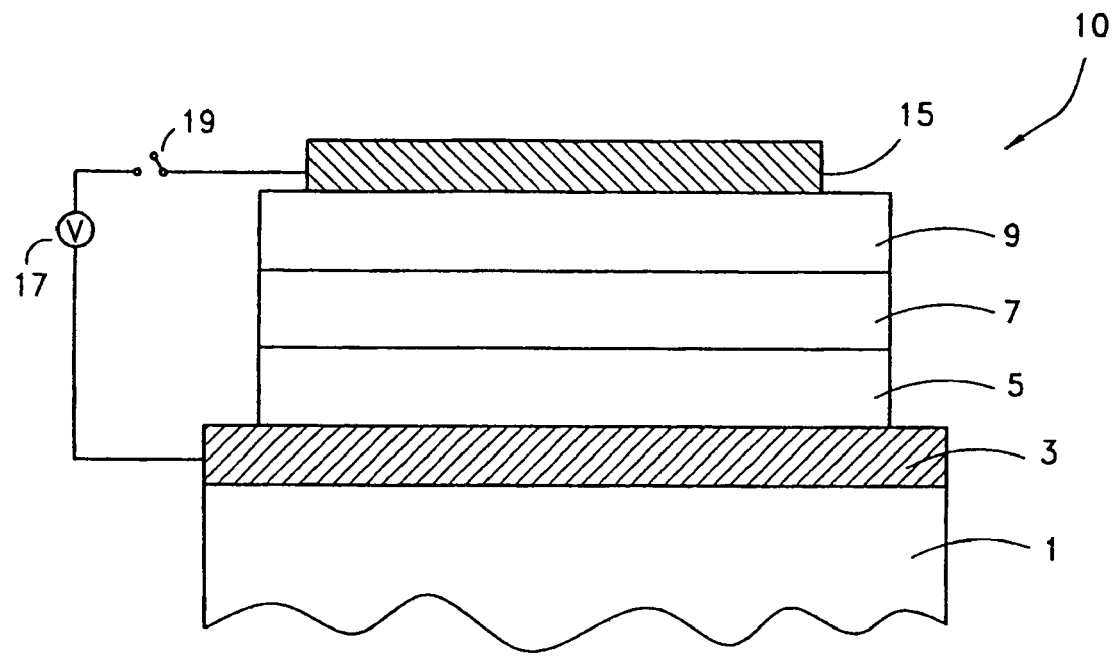
Figure 4:
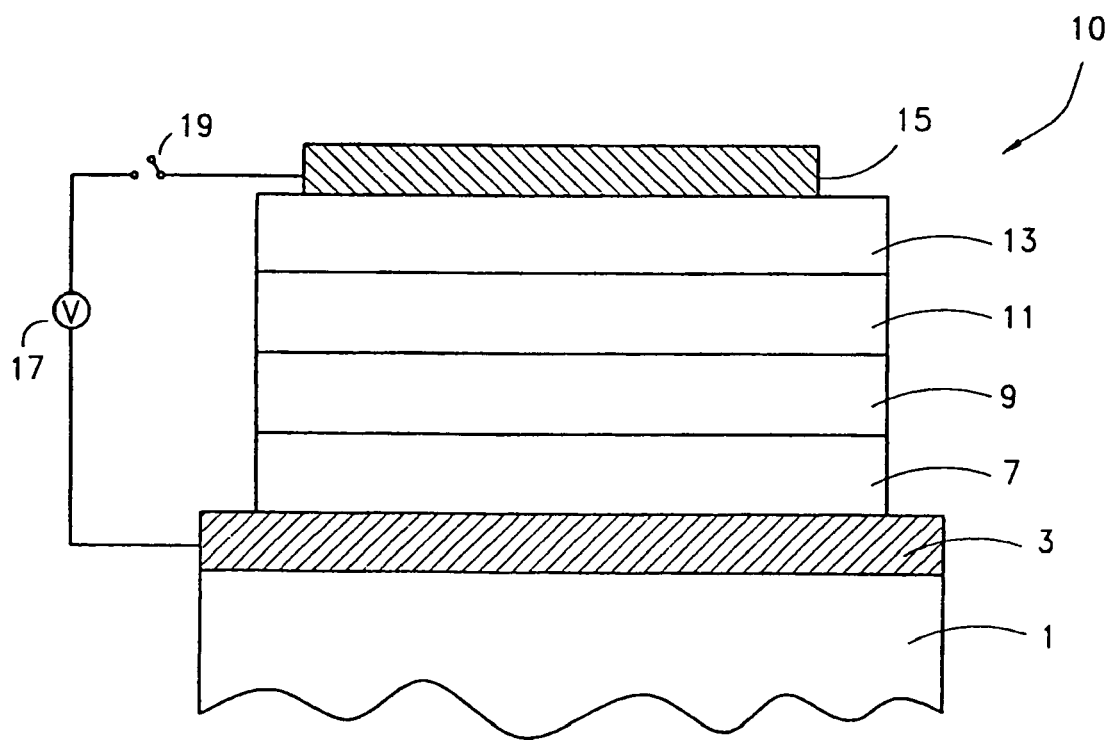
Figure 5:
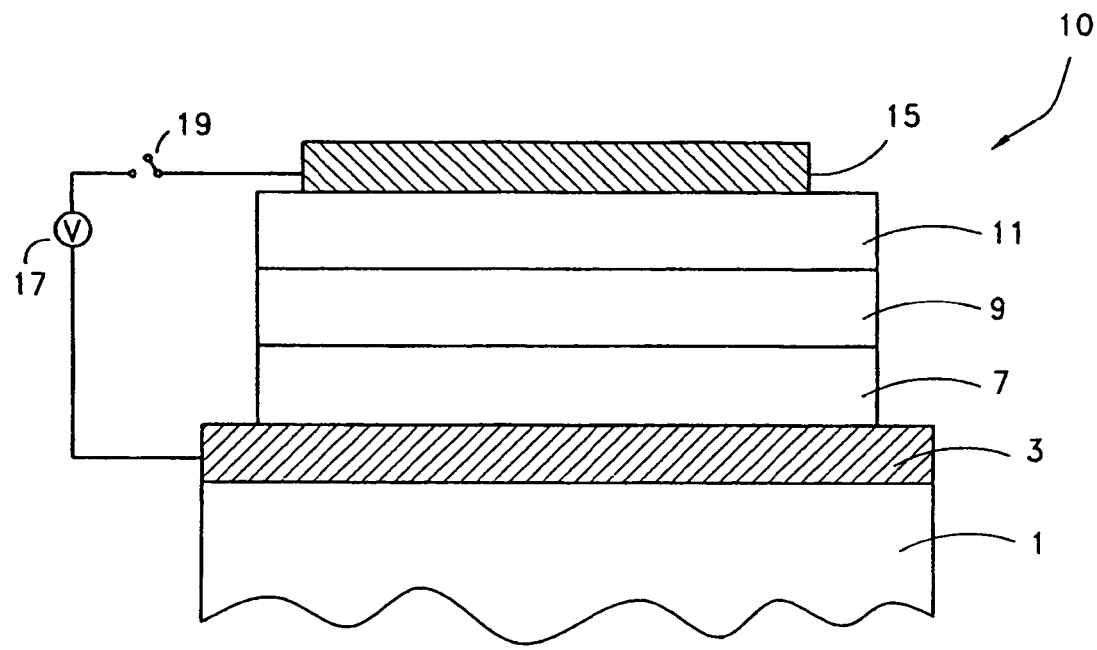
Figure 6:
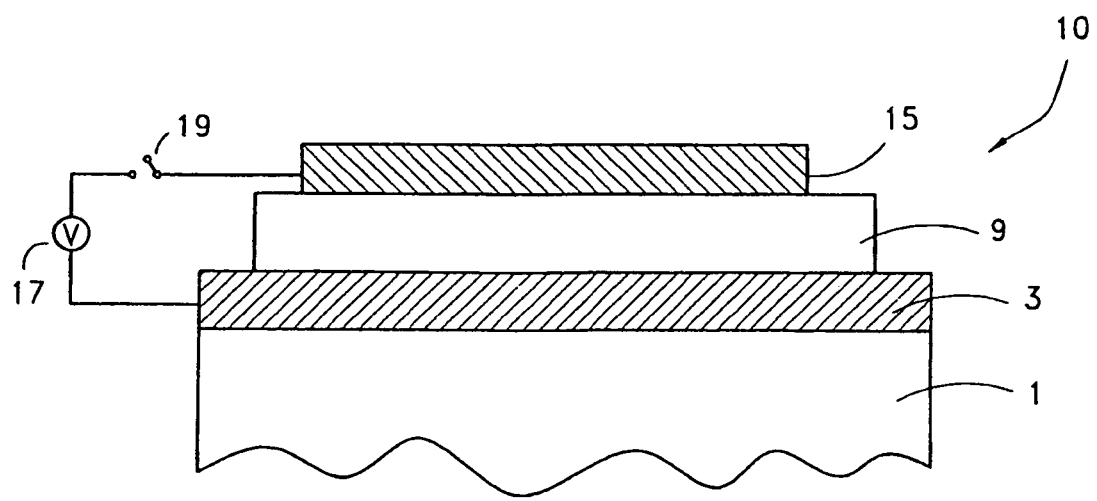
Figure 7:
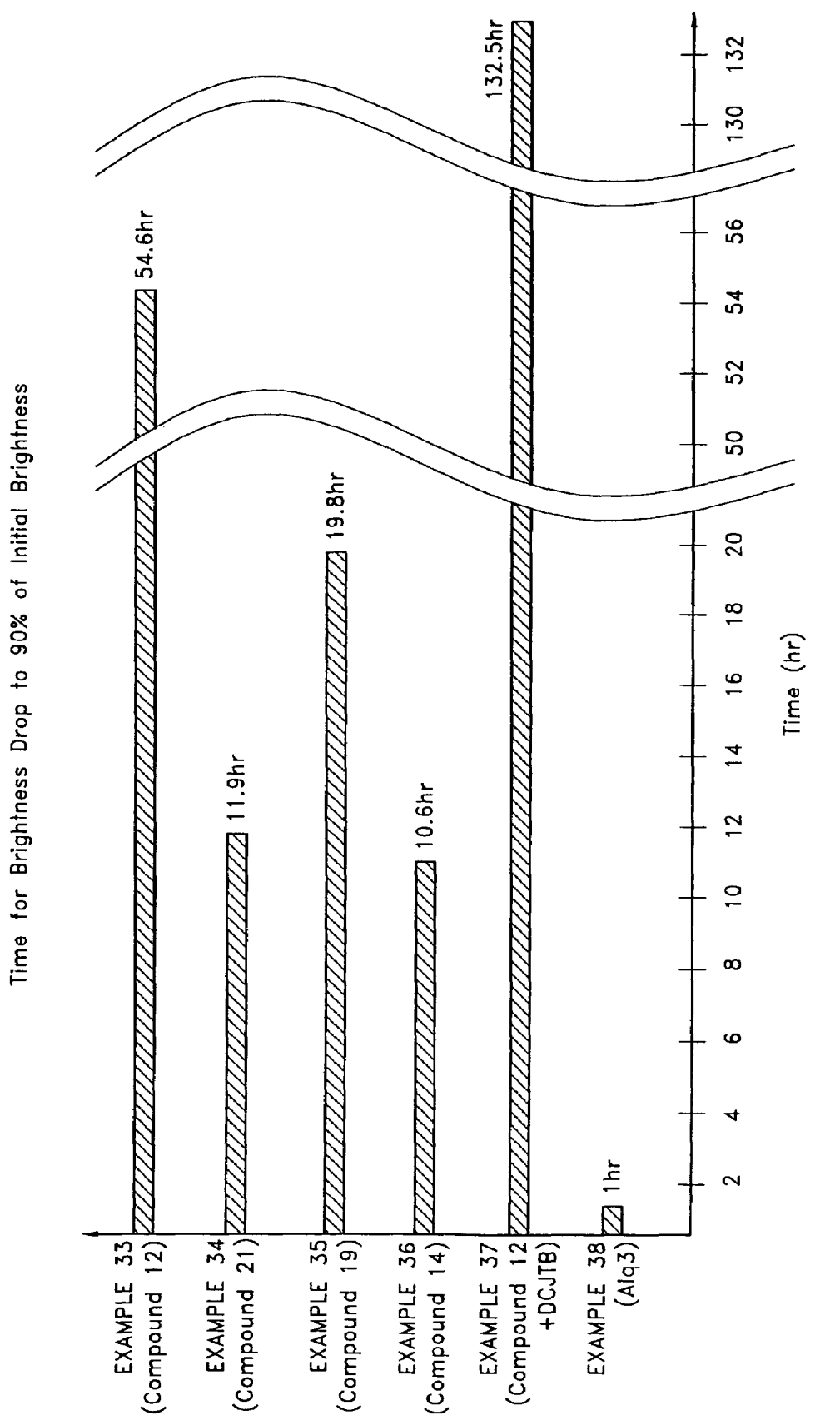
FIG. 7 illustrate times for 10% initial brightness drop of organic EL devices of Examples 33-38.

Now various constructions of organic EL devices according to the present invention will be discussed with reference to the accompanying drawings. FIGS. 1-6 illustrate cross-sectional constructions of organic EL devices that can be built in accordance with the present invention. In these drawings, the same reference numbers are used to indicate like layers or components among the constructions. The term "layer" refers to a deposit, coat or film of one compound or a mixture of more than one compound. It should be noted that these constructions are not exhaustive variants of the organic EL devices in accordance of the present invention.

The illustrated organic EL devices include a substrate 1, an anode 3, a cathode 15 and one or more layers located between the anode 3 and the cathode 15. Advantageously, the one or more intervening layers contain at least one of the compounds represented by Formula I. The one or more intervening layers include a hole-injecting layer 5, a hole-transporting layer 7, a light-emitting layer 9, an electron-transporting layer 11, an electron-injecting layer 13 and layers having functions of two or more of the foregoing layers.

The substrate 1 (FIGS. 1-6) supports the laminated structure of the organic EL device 10. The anode 3 (FIGS. 1-6) and cathode 15 (FIGS. 1-6) are electrically connected to an electric power source 17 (FIGS. 1-6) via a switch 19 (FIGS. 1-6), which is controlled by a controller (not shown). The electric power source is preferably a current source. The hole-injecting layer 5 (FIGS. 1-3) is to facilitate the injection of holes from the anode 3 into the hole-transporting layer 7 (FIGS. 1-5). Similarly, the electron-injecting layer 13 (FIGS. 1 and 4) is to facilitate the injection of electrons from the cathode 15 into the electron-transporting layer 13. The hole-transporting layer 7 is to accelerate movement of holes away from the anode 3 and/or the hole-injecting layer 5 toward the light-emitting layer 9 (FIGS. 1-6). The electron-transporting layer 11 (FIGS. 1, 2, 4 and 5) is to accelerate movement of electrons away from the cathode 15 and/or the electron-injecting layer 13 toward the light-emitting layer 9 (FIGS. 1-6).

Operation of Organic EL Devices

When applying an electric voltage between the electrodes 3 and 15, electrons and holes are injected from the cathode 15 and anode 3, respectively, into intervening layer(s). The traveling holes and electrons recombine at light emitting molecules preferably located in the light-emitting layer 9. Recombined pairs of electrons and holes, namely excitons, transfer the energy of the recombination to the light-emitting molecules where they recombined. Alternatively, excitons move around for a short period of time and transfer the recombination energy to other organic light-emitting, particularly to those having a smaller band gap near the location of their recombination. The transferred energy is used to excite valence electrons of the light-emitting molecules, which generates photons when the electrons return to their ground state.

Light-Emitting Layer

The light-emitting layer 9 is a layer particularly dedicated to the emission of visible light by the process of recombination of electrons and holes therein although it may have other functions as well. Although not illustrated, in an embodiment, a light-emitting layer may not be included as a separate layer in an organic EL device, in which visible light is generated where light-emitting materials are doped. An organic EL device of the present invention preferably includes a separate light-emitting layer.

In an embodiment involving the light-emitting layer 9 made of a single material, a compound satisfying Formula I advantageously forms the light-emitting layer. Alternatively, a non-Formula I compounds form the light-emitting layer 9, while one or more compounds of Formula I are used in one or more other layers of the organic EL device.

The light-emitting layer 9 of organic EL devices may be composed of either a single light-emitting compound or a mixture of two or more materials. In an embodiment involving the light-emitting layer 9 made of two or more compounds, the most included compound is called a host while the other or the others are called dopants. Preferably, both of the host and at least one dopant have the light-emitting property. Both of the host and at least one dopant may be selected from the compounds of Formula I. Alternatively, the host is selected from the compounds of Formula I while a dopant is selected from non-Formula I compounds. Still alternatively, a non-Formula I compound may be used as the host while a dopant is selected from the compounds satisfying Formula I. In a preferred embodiment, the host material is selected from the compounds satisfying Formula I with one or more dopant, whether the dopant is a compound satisfying Formula I.

For any of the foregoing embodiments containing compounds satisfying Formula I, each of R5 of Formula II and R1-R4, when they are not Formula II, is preferably a non double-spiral substituent of hydrogen, cyano, nitro, substituted or unsubstituted C1-20 alkyl, substituted or unsubstituted C2-C10 alkenyl, substituted or unsubstituted C3-C7 cycloalkyl, substituted or unsubstituted C4-C7 cycloalkenyl, substituted or unsubstituted aryl, substituted or unsubstituted heteroaryl, substituted or unsubstituted C1-C20 alkoxy, substituted or unsubstituted aryloxy, substituted or unsubstituted C1-C20 alkylamine, substituted or unsubstituted arylamine, substituted or unsubstituted alkylarylamine, substituted or unsubstituted C1-C20 alkylsilyl; substituted or unsubstituted arylsilyl; substituted or unsubstituted alkylarylsilyl, substituted or unsubstituted C1-C20 alkylboranyl, substituted or unsubstituted arylboranyl, substituted or unsubstituted alkylarylboranyl, substituted or unsubstituted C1-C20 alkylthio, or substituted or unsubstituted arylthio. In the foregoing groups, the substituted RI-RS are preferably substituted with cyano; nitro; formyl; C1-C20 alkyl, namely, methyl, ethyl or proply; aryl, namely, phenyl, naphthyl, biphenyl or anthracenyl; heteroaryl, namely imidazolyl, thiazolyl, oxazolyl, thiophenyl, pyridyl, pyrimidyl or pyrrolyl; C4-C7 cycloalkenyl, namely, cyclobutenyl or cyclopetenyl. C1-C20 alkoxy, namely, methoxy, ethoxy, propoxy; aryloxy, namely, phenoxy or naphthoxy; C1-C20 alkylamine, namely, methylamine, ethylamine or propylamine; arylamine, namely, phenylamine or naphthylamine; alkylarylamine, namely, methylphenylamine, ethylphenylamine or ethylnaphthylamine; C1-C20 alkylboranyl, namely, dimethylboranyl, diethylboranyl or dipropylboranyl; arylboranyl, namely, diphenylboranyl, dinaphthylboranyl or phenylnaphthylboranyl; alkylarylboranyl, namely, phenylmethylboranyl, naphthylmethylboranyl or naphthylethylboranyl; C1-C20 alkylsilyl, namely, trimethylsilyl, triethylsilyl or tripropylsilyl; arylsilyl, namely, triphenylsilyl or trinaphthylsilyl; alkylarylsilyl, namely, dimethylphenylsilyl, diethylphenylsilyl or diphenylmethylsilyl; C1-C20 alkylthio, namely, methylthio, ethylthio, propylthio or butylthio; and arylthio, phenylthio or naphthylthio. The compounds satisfying Formula I are selected from Compounds 1-96, preferably Compounds 1-36, more preferably Compounds 4, 12, 14, 19, 21, 23, 25, 17 and 29.

For any of the forgoing embodiments, persons of ordinary skill in the art would appreciate non-Formula I compounds that can be used in the light-emitting layer 9 either alone or with one or more other compounds. For example, non-Formula I light-emitting compounds for use in the light-emitting layer 9 include 8-hydroxyquinoline metal complexes including Alq3; carbazole compounds and derivatives thereof; dimerized styryl compounds (U.S. Pat. No. 5,366,811); BAlq (U.S. Pat. No. 5,150,006); 10-hydroxybenzo[h]quinoline-metal complexes (U.S. Pat. No. 5,529,853); 2-(2'-hydroxy-5'methylphenyl)benzotriazole metal complexes (U.S. Pat. No. 5,486,406); benzoxazole, benzthiazole, benzimidazole and derivatives thereof (U.S. Pat. No. 5,645,948); poly(p-phenylene vinylene) and derivatives thereof (*Conjugated Polymers as Solid-State Laser Materials*, Synthetic Metals 91, 35 (1997); and *Low Voltage Operation of Large Area Polymer LEDs*, Synthetic Metals 91, 109 (1997)); spiro compounds (U.S. Pat. No. 5,840,217); polyfluorene, rubrene or the like. The referenced documents and patents are hereby incorporated herein by reference.

Dopants

Organic EL devices of the present invention may be constructed with or without a dopant. Dopants are introduced to improve the light-emission efficiency, to tune the color of the emission, and/or to simply emit light from a layer having a non-fluorescent host. Dopants can be added to the light-emitting layer 9 and one or more of the other layers 5, 7, 11 and 13. More than one light-emitting material can be doped together in these layers for various purposes. Further, in an embodiment of the organic EL devices according to the present invention, the light-emitting layer 9 may be absent. In such constructions, one or more light-emitting dopants are necessarily put in one or more of the layers 5, 7, 11 or 13 to generate visible light therefrom.

Generally, dopants for the light-emitting layer 9 are selected from light-emitting materials having higher quantum efficiency than the host material. Preferably, the dopants have a quantum yield close to "1" in a dilute system. This means that most of the energy received from excitons contributes to the light emission rather than releasing it in other forms such as generating heat. Also, dopants are selected such that they match energetically with the host material. Excitons are known to have a tendency to transfer their energy to a material having a smaller band gap among materials near the recombination location; thus, dopants are advantageously selected from the light-emitting materials having a band gap smaller than that of the host material. Depending upon the matching of the dopants and host materials, recombination may occur in the host molecules, and the energy of the generated excitons is transferred to the dopants. In this case, visible light is emitted from the dopant molecules. Also, the energy of the excitons may be transferred to another dopant, where the light is emitted.

Further, dopants are preferably selected from a light-emitting materials having a band gap "slightly" smaller than that of the host material. Smaller band gap difference between host and dopant molecules provide more efficient energy transfer from the host molecule to the dopant molecules. In inefficient energy transfer, for example some hosts do not transfer the recombination energy to dopants and may generate its own light while dopants that received energy from other hosts also generates light. The resulting light is a mixture of the colors of host and dopant's, which is normally not desirable in creating full color display. Thus, when a dopant is determined, the host is selected from various compounds having a slightly larger band gap than that of the dopant, vice versa. The dopant's band gap can have any value from about 60% up to 100% of the value of the host's band gap, preferably, from about 80% up to 100%.

In an embodiment, the dopant is selected from the compounds satisfying Formula I whether or not the host is a compound of Formula I. Preferably, the dopants are selected from Compounds 1-96, more preferably, Compounds 1-36 with or without non-Formula I dopants. In another embodiment, the dopant is a non-Formula I compound whether or not the host is a Formula I compound. Whether the dopant is a Formula I compound or a non-Formula I compound, it preferably has fluorescent or phosphorescent property. Preferably, the dopant is a phosphorescent material, which converts triplet energy that would not be used in fluorescent materials into light via an internal process called "triplet to singlet transition". A general description of the triplet to singlet transition can be found in *Nature* (403,6771, 2000, 750-753), which is hereby incorporated herein by reference.

In a preferred embodiment, the dopant is a non-Formula I light-emitting compound whereas the host is a compound of Formula I. When the dopant is determined, the host is chosen from the compounds of Formula I having a matching band gap as discussed above. Persons of ordinary skill in the art would appreciate non-Formula I compounds that can be used as dopants in the light-emitting layer 9 or other layers 3, 5, 7, 11 and 13. Examples of non-Formula I doping materials are BCzVBi or 2,2'-([1,1'-biphenyl]-4,4'-diyldi-2,1-ethenediyl) bis[9-ethyl-9H-carbazole, perylene, rubrene, DCJTB or 2-(1, 1-dimethylethyl)-6-[2-(2,3,6,7-tetrahydro-1,1,7,7-tetramethyl-1H,5H-benzo[ij]quinolizin-9-yl)ethenyl]-4H-pyran-4-ylidene]-propanedinitrile, quinacridone and its derivatives, coumarine and its derivatives, nile red, DCM1 or 2-[2-[4-(diethylamino)phenyl]ethenyl]-6-methyl-4H-pyran-4-ylidene]-propanedinitrile, DCM2 or 2-methyl-6-[2-(2,3,6,7-tetrahydro-1H,5H-benzo[ij]quinolizin-9-yl)ethenyl]-4H-pyran-4-ylidene]-propanedinitrile, tetradiphenylamino pyrimido-pyrimidine, pyrydinothiadiazole, and the like, including Compounds 201-220 although not limited thereto.

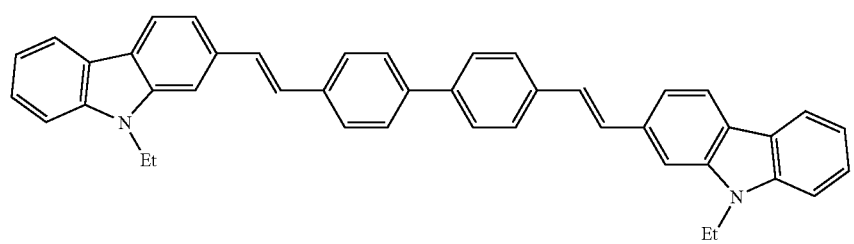

Compound 201

-continued
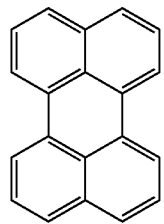
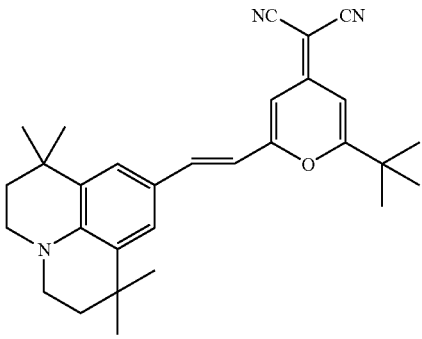
Compound 202
Compound 203
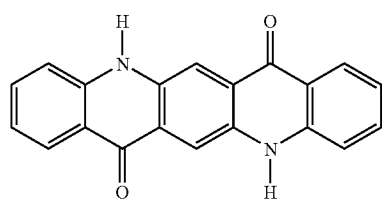
Compound 204
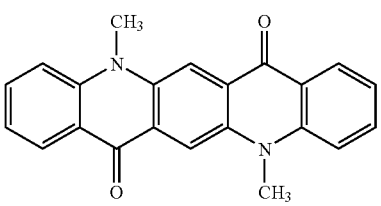
Compound 205
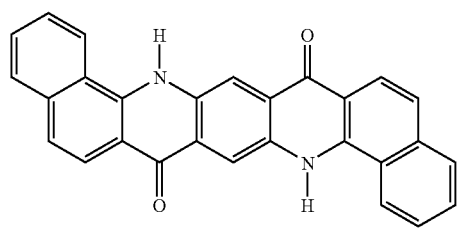
Compound 206
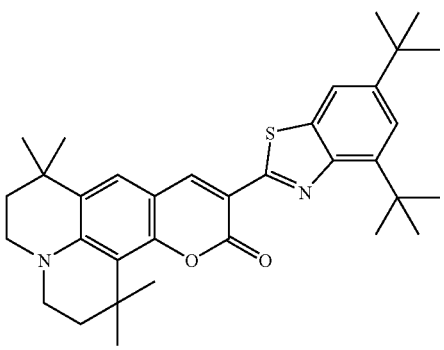
Compound 207
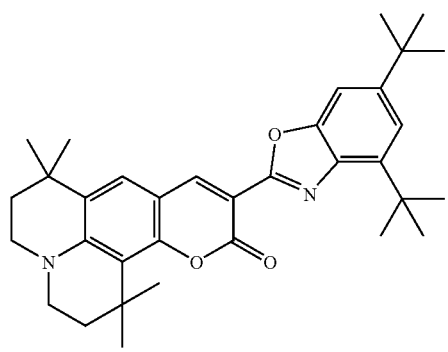
Compound 208
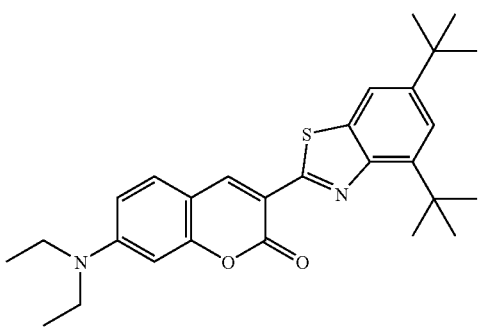
Compound 209
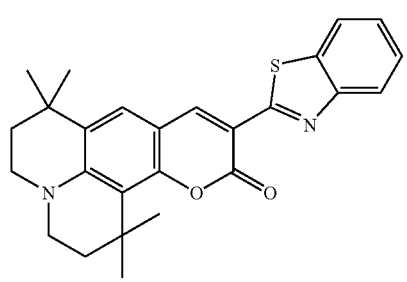
Compound 210
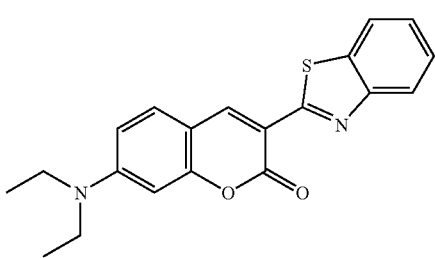
Compound 211

-continued
Compound 212
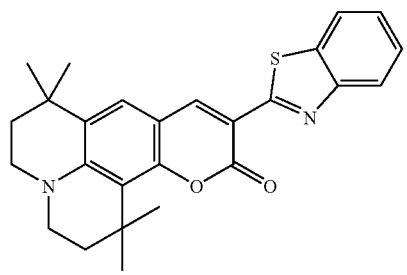
Compound 213
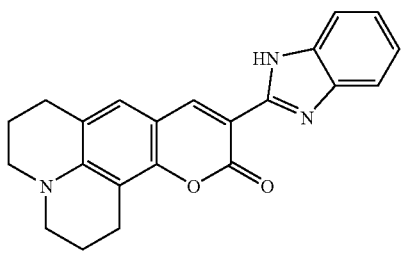
Compound 214
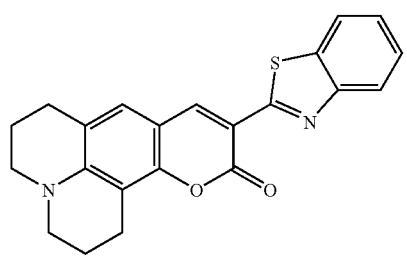
Compound 215
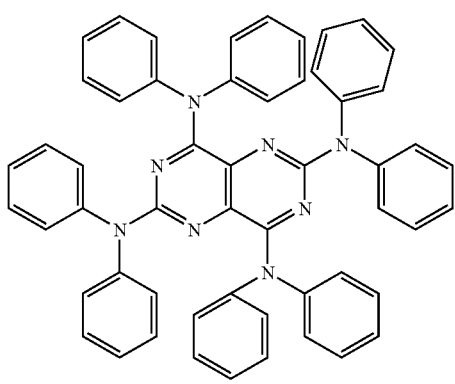
Compound 216
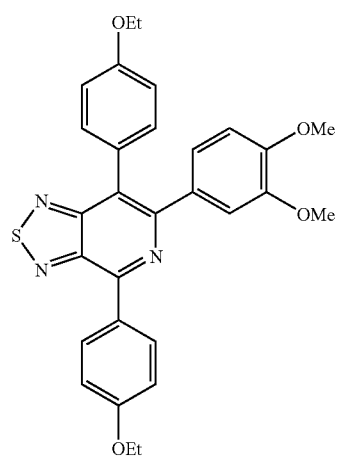
Compound 217
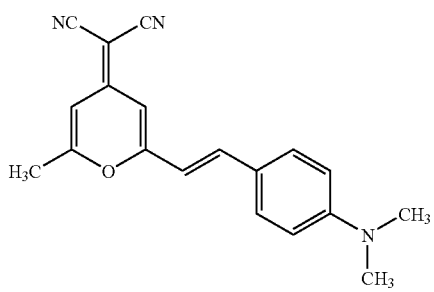
Compound 218
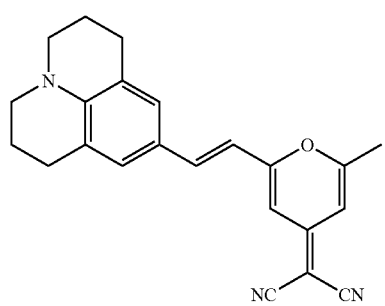
Compound 219
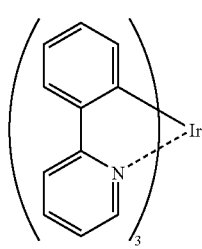

-continued

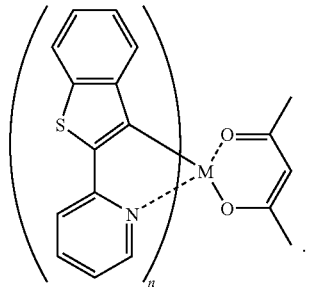

Compound 220

Some of the exemplified and additional materials for use as dopants, either fluorescent or phosphorescent, are disclosed in U.S. Pat. Nos. 6,020,078; 5,059,863; 6,312,836 B1; 4,736,032; 5,432,014; 5,227,252; and 6,020,078; European Patent Publication 1 087 006 A1; Japanese Patent Publication Nos. 6-2240243 A, 6-9952 A, 7-166160 A, 6-240243 A, 6-306357 A, 6-9952 A, 6-240243 and 7-166160 A; *High efficiency organic electrophosphorescent devices with tris(2-phenylpyridine)iridium doped into electron-transporting materials*, C. Adachi, M. A. Baldo, and S. R. Forrest, *Applied Physics Letter*, 77, 904, 2000; *High efficiency red electrophosphorescence devices*, C. Adachi, M. A. Baldo, S. R. Forrest, S. Lamansky, M. E. Thompsom, and R. C. Kwong, *Applied Physics Letter*, 78, 1622, 2001; *Organic Light-Emitting Devices With Saturated Red Emission Using 6,13-Diphenylpentacene*, Appl. Phys. Lett. 78, 2378 (2001); *Photoluminescence and Electroluminescence Properties of Dye-Doped Polymer System*, Synthetic Metals 91, 335 (1997); *Fabrication of Highly Efficient Organic Electroluminescent Devices*, Appl. Phys. Lett. 73, 2721 (1998); *Organic Electroluminescent Devices Doped With Condensed Polycyclic Aromatic Compounds*, Synthetic Metals 91, 27 (1997); *Bright Blue Electroluminescent Devices Utilizing Poly (N-Vinylcarbazole) Doped With Fluorescent Dye*, Synthetic Metals 91, 331 (1997); *Doped Organic Electroluminescent Devices With Improved Stability*, Appl. Phys. Lett. 70, 1665 (1997); *Stability Characteristics Of Quinacridone and Coumarine Molecules as Guest Dopnats in The Organic Leds*, Synthetic Metals 91, 15 (1997); *Strongly Modified Emission From Organic Electroluminescent Device With a Microcavity*, Synthetic Metals 91, 49 (1997); *Organic Light-Emitting Diodes Using a Gallium Complex*, Appl. Phys. Lett. 72, 1939 (1998); *Orange and Red Orgnanic Light-Emitting Devices Using Aluminum Tris(5-Hydroxyquinoxaline)*, Synthetic Metals 91, 217 (1997); *Synthesis and Characterization of Phosphorescent Cyclometalated Iridium Complexes*, Inorg. Chem. 40, 1704 (2001); *Highly Phosphorescent Bis-Cyclometalated Iridium Complexes*, J. Am. Chem. Soc. 123, 4304, (2001); *High Quantum Efficiency in Organic Light-Emitting Devices with Iridium-Complex as Triplet Emissive Center*, Jpn. J. Appl. Phys. 38, L1502 (1999); *Optimization of Emitting Efficiency in Organic LED Cells Using Ir Complex*, Synthetic Metals 122, 203 (2001); *Operating lifetime of phosphorescent organic light emitting devices*, Appl. Phys. Lett. 76, 2493 (2000); *High-Efficiency Red Electrophosphorescence Devices*, Appl. Phys. Lett. 78, 1622 (2001); *Very High-Efficiency Green Organic Light-Emitting Devices Based on Electrophosphorescence*, Appl. Phys. Lett. 75, 4 (1999); *Highly-Efficient Organic Electrophosphorescent Devices With Tris (2-Phenylpyridine)Iridium Doped Into Electron-Transporting Materials*, Appl. Phys. Lett. 77, 904 (2000); and *Improved Energy Transfer In Electrophosphorescent Devices*, Appl. Phys. Lett. 74, 442 (1999), all of which are hereby incorporated herein by reference.

Substrate

Although the drawings show that the substrate 1 is located on the side of the anode 3, alternatively, the substrate 1 may be located on the side of the cathode 15. In either case, the substrate 1 provides a support on which the laminated construction of the organic EL device can be build during the manufacturing. Also, the substrate 1 functions as a protective layer for the construction of the organic EL device once manufactured. Thus, materials for the substrate 1 are selected from those, which can stand the conditions of manufacturing processes and usage of the organic EL devices. Persons of ordinary skill in the art would well appreciate what materials can satisfy the requirements based on the conditions.

In some organic EL device constructions, for example, the light emitted from the one or more intervening layers 5, 7, 9, 11 and 13 pass through the substrate 1. In such constructions, the substrate 1 is advantageously made of a transparent material to allow the visible light emitted from the light-emitting layer 9 to pass through. Transparent materials, which can be used for the substrate 1, for example, include glass, quartz and any other appropriate natural or artificial materials. Preferably, glass is used for the substrate 1. In other constructions of organic EL devices, for example, the light can be emitted through the cathode 15 or any directions other than through the substrate 1. In such constructions, the substrate 1 is advantageously made of highly reflective material satisfying thermodynamic and mechanical requirements for forming the anode 3 thereon. For example, semiconductor wafers, metal oxide, ceramic materials, and non-transparent plastics can be used as the substrate 1. A transparent substrate coated with a reflective material can also be used.

Anode

The anode 3 is a conductive electrode electrically connected to the electric power source 17. Although not illustrated, the anode 3 may be constructed in multiple layers of materials. The thickness of the anode 3 may vary depending on the materials used and its layered structures. However, the anode 3 is advantageously from about 10 nm to about 1000 nm, preferably from about 10 nm to about 500 nm.

The anode 3 requires a relatively large work function to favor injection of holes. Advantageously, the work function of materials for the anode 3 is about 4 eV or greater. For example, conductive materials, which can be used for the anode 3, include carbon; aluminum, vanadium, chromium, copper, zinc, silver, gold, similar metals, and alloys of the foregoing metals; zinc oxide, indium oxide, indium tin oxide (ITO), indium zinc oxide and similar tin oxide or tin oxide indium-based complex compounds; mixtures of oxides and metals, such as ZnO:Al, SnO$_2$:Sb; and conductive polymers, such as poly(3-methylthiophene), poly[3,4-(ethylene-1,2-dioxy)thiophene], polypyrrole and polyaniline. Either transparent or non-transparent materials can be selected for the anode 3, depending upon the construction of the light passage in the organic EL device as discussed above in connection with the materials for the substrate 1. Preferably, the anode 3 is made of ITO. Those of ordinary skill in the art would appreciate any other materials that can be used in the anode 3 and also the selection of appropriate anode materials.

Cathode

The cathode 15 is also a conductive electrode electrically connected to the electric power source 17. Although not illustrated, the cathode 15 may be constructed in multiple layers of materials. The thickness of the cathode 15 may vary depending on the materials used and its layered structures. However, the cathode 15 is laminated generally from about 1 nm to about 10,000 nm, preferably from about 5 nm to about 5,000 nm.

The cathode 15 requires a relatively small work function to favor injection of electrons. Advantageously, the work function of materials for the cathode 15 is about 4 eV or smaller. For example, conductive materials, which can be used for the cathode 15, include magnesium, calcium, sodium, potassium, titanium, indium, yttrium, lithium, gadolinium, aluminum, silver, tin, lead, similar metals, and alloys of foregoing metals. Multi-layered cathode materials include LiF/Al and Li$_2$O/Al. Preferably, the cathode 15 is made of aluminum-lithium alloy, LiF/Al or Li$_2$O/Al. Either transparent or non-transparent materials may be used for the cathode 15, depending upon the construction of the light passage in the organic EL device as discussed above. Those of ordinary skill in the art would appreciate any other materials that can be used in the cathode 15 and also the selection of appropriate cathode materials.

Hole-Injecting Layer

The hole-injecting layer 5 has the function of enabling a large number of holes to be injected from the anode 3 at a low electric field applied to the device. The hole-injecting layer 5 advantageously is formed in the case where the interfacial strength between anode layer 3 and hole-transporting layer 7 is not strong enough. Also, the hole-injecting layer 5 may be formed when the work function of the anode material is significantly different from the highest occupied molecular orbital (HOMO) level of the material of its neighboring layer 7, 9, 11 or 13. The hole-injecting layer 5 effectively reduces the electric potential barrier in the hole injection, resulting in reduction of driving voltage of the organic EL devices. The HOMO level of the hole-injecting material is advantageously located between the work function of the anode 3 and the HOMO level of the other neighboring layer 9, 11 or 13, although not limited thereto. Advantageously, the HOMO level of the compounds for hole-injecting layer 5 ranges from about −4.0 eV to about −6.0 eV. Also, the hole-injecting material is preferred to be transparent when the construction of the organic EL device allows the light emission through the substrate 1. In otherwise constructions, the hole-injecting material is advantageously non-transparent.

In accordance with one embodiment of organic EL devices, the hole-injecting layer 5 may be made of one or more of the organic compounds satisfying Formula I. In this embodiment, one or more compounds that are not represented by Formula I (non-Formula I compounds) may be added. In another embodiment of organic EL devices, one or more compounds of Formula I are used in one or more other layers of the device, while one or more non-Formula I compounds form the hole-injecting layer 5. Those of ordinary skill in the art will appreciate non-Formula I compounds that can be used in the hole-injecting layer 5 and also the selection of appropriate materials.

The non-Formula I compounds that can be used in hole-injecting layer 5 include, for example, metal porphyrine (U.S. Pat. Nos. 4,720,432 and 4,356,429); oligothiophene (U.S. Pat. No. 5,540,999); arylamines and derivatives thereof (U.S. Pat. Nos. 5,256,945, 5,609,970, and 6,074,734, and Japanese Unexamined Patent Publications 1999-219788 and 1996-269445); hexanitrile hexaazatriphenylene; conductive polymers such as derivatives of polyaniline, polythiophene with or without acid dopant; derivatives of quinacridone; derivatives of perylene (U.S. Pat. No. 5,998,803); and anthraquinone (Japanese Unexamined Patent Publication 2000-058267). The referenced U.S. patents and Japanese publications are hereby incorporated herein by reference.

Hole-Transporting Layer

The hole-transporting layer 7 has the function to smoothly transfer the holes from the hole-injecting layer 5 or from anode 3 (in the absence of the hole-injecting layer 5) toward the light-emitting layer 9 or toward an area where light-emitting materials are doped. Preferably, materials good for use in the hole-transporting layer 7 are those having high hole mobility therein. The high mobility of holes in those compounds will reduce the driving voltage of an organic EL device because holes in the compounds having high hole mobility are prone to move at a low electric potential difference. Advantageously, the compounds for use in the hole-transporting layer 7 have hole mobility of about $1 \times 10^{-7}$ cm$^2$/Vs or greater. Advantageously, the hole-transporting layer 7 has the function to inhibit electrons from moving into it from its neighboring layer 9, 11, or 13 on the side of the cathode 15. Materials having low mobility of electrons is preferred. In the constructions which do not have a separate hole-injecting layer (FIG. 4), the hole-transporting layer 7 functions for both the hole injection and hole transportation. In this case, materials having hole-injecting property discussed above would also be preferred.

In accordance with an embodiment of organic EL devices of the present invention, the hole-transporting layer 7 can be made of one or more of the organic compounds satisfying Formula I. In this embodiment, one or more compounds that are not represented by Formula I (non-Formula I compounds) may be added. In another embodiment of organic EL devices, one or more compounds of Formula I are used in one or more other layers of the device, while one or more non-Formula I compounds form the hole-transporting layer 7. The non-Formula I compounds that can be used in the hole-transporting layer 7 include, for example, arylamine derivatives, conjugated poylmers, block co-polymers with conjugated and non-conjugated repeating units, and the like. Advantageously, derivatives of the arylamine, 4,4'-bis[N-(1-naphthyl)-N-phenylamino]biphenyl (NPB) is used for the hole-transporting layer 7. Those of ordinary skill in the art will appreciate non-Formula I compounds that can be used in the hole-transporting layer 7 and also the selection of appropriate materials.

Electron-Transporting Layer

The electron-transporting layer 11 contains a material prone to transfer electrons injected from the electron injecting layer 13 or the cathode 15 (in the absence of the electron-injecting layer 13) to the light-emitting layer 9 or to an area where a light-emitting material is doped. If the material meets the requirements for the electron-injecting layer 13, the functions of electron-transportation and injection can be combined in a single layer as shown FIG. 2.

Preferably, compounds having high electron mobility is used as an electron-transporting material because high mobility of electrons will reduce the driving voltage of the organic EL devices using the compounds. Injected electrons in such compounds having high electron mobility are prone to move at a low electric potential difference. Advantageously, the compounds having electron mobility of about $1 \times 10^{-7}$ cm$^2$/Vs or greater can be used for electron transportation. Preferably, the electron-transporting layer 11 also has the function of blocking holes to move thereinto. Materials having low mobility of holes are preferred. Compounds having hole mobility of about $1 \times 10^{-3}$ cm$^2$/VS or less are preferred. A general discussion on carrier mobility can be found in *Electron Mobility in Tris(8-hydroxy-quinoline)aluminum Thin Films Determined via Transient Electroluminescence From Single- and Multiple-Layer Organic Light-Emitting Diodes*, J. Appl. Phys., Vol 89, 3712 (2001); *Transient Electroluminescence Measurements on Organic Heterolayer Light Emitting Diodes*, Synthetic Metals 111-112, 91 (2000); and *Organic Electroluminescence of Silole-Incorporated Polysilane*, Journal of Luminescence 87-89, 1174 (2000), which are hereby incorporated herein by reference.

In accordance with an embodiment of organic EL devices of the present invention, the electron-transporting layer 11 can be made of one or more of the compounds satisfying Formula I. One or more compounds that are not represented by Formula I (non-Formula I compounds) may be added. In another embodiment of organic EL devices, one or more compounds of Formula I are used in one or more other layers of the EL device, while one or more non-Formula I compounds form the electron-transporting layer 11. Those of ordinary skill in the art will appreciate non-Formula I compounds that can be used in the electron-transporting layer 11 and also the selection of appropriate materials.

The non-Formula I compounds that can be used in the electron-transporting layer 11 include, for example, aluminum complexes of 8-hydroxyquinoline; organometallic complex compounds including Alq3 (U.S. Pat. No. 5,061,569 and U.S. patent application Ser. No. 09/540,837); organic radical compounds (U.S. Pat. No. 5,811,833); hydroxyflavon-metal complexes (U.S. Pat. Nos. 5,817,431 and 5,516,577, Japanese Unexamined Patent Publications 2001-076879, 2001-123157 and 1998-017860, and *Organic Light-emitting Diodes using 3- or 5-hydroxyflavone-metal Complexes*, Appl. Phys. Lett. 71 (23), 3338 (1997).) The referenced documents are hereby incorporated herein by reference.

Electron-Injecting Layer

The electron-injecting layer 13 is generally to faciliate injection of a large number of electrons from the cathode 15 at a low electric field applied across the device. The electron-injecting layer 13 may be provided when the work function of the cathode 15 significantly differs from the lowest unoccupied molecular orbital (LUMO) level of the other neighboring layer 5, 7, 9 or 11. Much difference in the energy level act as an electric potential barrier of the electron injection. An electron-injecting layer reduces the electric potential barrier and facilitates the electron injection in the device. The electron-injecting layer 13 may also be introduced to prevent excitons generated in the neighboring layer 5, 7, 9 or 11 from moving toward the cathode layer 15. In the alternative or in addition, the electron-injecting layer 13 may be provided to avoid damaging the neighboring layer 5, 7, 9 or 11 in the course of the deposition of the cathode layer 15. The LUMO level of the electron-injecting material is advantageously located between the work function of the cathode material and the LUMO level of the other neighboring layer 5, 7, 9 or 11, preferably near the middle of the two. Advantageously, the LUMO level of compounds used for electron injection ranges from about −2.5 eV to about −4.0 eV. Further, the electron-injecting layer 13 is required to have strong interface with the cathode layer 15.

In accordance with an embodiment of organic EL devices of the present invention, the electron-injecting layer 13 can be made of one or more of the compounds of Formula 1. One or more of the non-Formula I compounds may be added. In another embodiment of organic EL devices, one or more compounds of Formula I are used in one or more other layers of the organic EL device, while one or more non-Formula I compounds form the electron-injecting layer 13. Those of ordinary skill in the art will appreciate non-Formula I compounds that can be used in the electron-injecting layer 13 and also the selection of appropriate materials.

The non-Formula I compounds that can be used in the electron-injecting layer 13 include, for example, aluminum complexes of 8-hydroxyquinoline, organometallic complex compounds including Alq3, organic radical compounds (U.S. Pat. No. 5,811,833); 3- or 5-hydroxyflavone-metal complexes (*Organic Light-emitting Diodes using 3- or 5-hydroxyflavone-metal Complexes*, Appl. Phys. Lett. 71 (23), 3338 (1997)); the electron-injecting compounds disclosed in Japanese Unexamined Patent Publications 2001-076879, 2001-123157 and 1998-017860; poly(p-phenyleneethylene), poly (triphenyldiamine), and spiroquinoxaline (*Polymeric Light-Emitting Diodes Based on Poly(p-phenyleneethylene), Poly (triphenyldiamine), and Spiroquinoxaline*, Adv. Funct. Mater. 11, 41, (2001)); the electron-injecting compounds disclosed in *High-efficiency oligothiophene-based light-emitting diodes*, Appl. Phys. Lett. 75, 439 (1999); the electron-injecting compounds disclosed in *Modifiede Oligothiophenes with High Photo-and Electroluminescence Efficiencies*, Adv. Mater. 11, 1375 (1999). The referenced documents are hereby incorporated herein by reference.

Manufacturing the Device

Various layers of the organic EL devices of the present invention can be produced by utilizing any known film forming techniques, including physical vapor deposition (PVD), chemical vapor deposition (CVD), spin coating, inkjet printing, screen-printing, roll-coating. These techniques are generally described in the following publications, which are hereby incorporated herein by reference: *Applied Physics Letters*, 73, 18, 1998, 2561-2563 *Applied Physics Letters*, 78, 24, 2001, 3905-3907.].

Advantageously, layers containing one or more compounds satisfying Formula I may be formed on a support using PVD, CVD, spin coating, inkjet printing. Preferably, a layer containing one or more compounds satisfying Formula I is produced using PVD, spin coating or inkjet printing, more preferably, PVD. Spin coating or inkjet printing can be preferably utilized for the formation of a layer containing one or more compounds which satisfy Formula I and have one or more C10-C20 linear chains therein. For the layers of non-Formula I compounds, persons of ordinary skill in the art would appreciate the matching technology for each compound.

EXAMPLES

Various aspects and features of the present invention including the compounds satisfying Formula I, the synthesis thereof, organic EL devices containing the compounds and manufacture of the devices will be further discussed in terms of the examples. The following examples are intended to illustrate various aspects and features of the present invention but not to limit the scope of the present invention.

Examples of Synthesis

Example 1

Synthesis of Compound 101

2,6-Diaminoanthraquinone (23.8 g, 100 mmol) was dispersed in 48 wt % of a hydrogen bromide aqueous solution. Sodium nitrite ($NaNO_2$, 14.1 g, 204 mmol) was slowly added to the mixture at −20° C., which evolved nitrogen gas. After gas evolution was completed, a solution of copper bromide (CuBr, 29.5 g, 206 mmol) dissolved in 48 wt % of a hydrogen bromide aqueous solution (63 mL) was slowly added to the mixture together with a small amount of ethanol (50 mL). The temperature of the resulting mixture was slowly elevated and then the mixture was slowly refluxed. The result was cooled to room temperature and was dilute with water. Precipitate in the mixture was filtered off with suction, washed with water, and dried in vacuo. Then, the dried precipitate was dissolved in chloroform, filtered through a short column of silica gel, and concentrated under reduced pressure. Purification by column chromatography and recrystallization from chloroform yielded Compound 101 (10.0 g, 27%). The analysis result of the compound is: 1H NMR (300 MHz, $CDCl_3$), 8.44 (d, J=2.1 Hz, 2H), 8.18 (d, J=8.0 Hz, 2H), 7.95 (dd, J=2.1, 8.0 Hz, 2H.)

Example 2

Synthesis of Compound 102

2-Bromo biphenyl (8.83 mL, 51.2 mmol) was dissolved in dry tetrahydrofurane (THF, 200 mL) under a nitrogen atmosphere at room temperature. The solution is cooled to −78° C. in a cooling bath. T-butyl lithium (60 mL, 1.7 M pentane solution) was slowly added to the solution at −78° C., and the resulting mixture was stirred for about 40 minutes at the same temperature. Thereafter, Compound 101 (7.50 g, 20.5 mmol) was added to the mixture at the same temperature. The cooling bath was removed, and the mixture was stirred at room temperature for about 15 hours. Thereafter, the mixture was quenched with diethyl ether (200 mL) and 2 N hydrochloric acid (200 mL) and was stirred at room temperature for about 40 minutes. Precipitate was filtered off with suction, and washed with water and ethyl ether. The material was dried to obtain Compound 102 (11.8 g, 85%).

Example 3

Synthesis of Compound 103

A mixture of Compound 102 (4.00 g, 5.93 mmol), potassium iodide (9.85 g, 59.3 mmol), and sodium hypophosphite hydrate (10.4 g, 98.0 mmol) was refluxed in a liquid mixture of acetic acid (80 mL) and ortho-dichlorobenzene (600 mL). The resulting mixture was cooled to room temperature. Then, the mixture was extracted with chloroform, dried over magnesium sulfate, and concentrated under reduced pressure. The concentrated solid was dissolved in chloroform, passed through a short silica gel column, and concentrated under reduced pressure. The solid was dispersed in n-hexane, agitated and filtered, and then vacuum dried to obtain Compound 103 (3.30 g, 87%) in a light yellow color. The analysis result of the compound is: m.p. 478.1° C.; 1H NMR (300 MHz, CDCl3) 7.92 (d, J=7.6 Hz, 4H), 7.46 (t, J=8.0 Hz, 4H), 7.33 (t, J=7.4 Hz, 4H), 7.21 (d, J=7.6 Hz, 4H), 6.88 (dd, J=2.1, 8.6 Hz, 2H), 6.47 (d, J=2.1 Hz, 2H), 6.22 (d, J=8.6 Hz, 2H); MS (M+) 636; Anal. Calc'd. for $C_{38}H_{22}Br_2$: C, 71.50; H, 3.47; Br, 25.03. Found: C, 71.90; H, 3.40; Br, 25.7.

Example 4

Synthesis of Compound 104

Copper bromide ($CuBr_2$, 17.9 g, 80.0 mmol) and t-butyl nitrite (12 mL, 101 mmol) were dispersed in acetonitrile (250 mL) at 65° C., and the dispersion mixture was agitated. To the mixture, 2-aminoanthraquinone (15.0 g, 67.2 mmol) was slowly added dropwise over about 5 minutes, which evolved nitrogen gas. After gas evolution was completed, the mixture was cooled to room temperature, quenched with 20% hydrochloric acid (1,000 mL), and extracted with dichloromethane. The organic extract was dried with magnesium sulfate, and concentrated under reduced pressure. Purification by column chromatography (dichloromethane/n-hexane=4/1) yielded Compound 104 (14.5 g, 75%). The analysis result of the compound: m.p. 207.5° C.; 1H NMR (500 MHz, $CDCl_3$), 8.43 (d, J=1.8 Hz, 1H), 8.30 (m, 2H), 8.17 (d, J=8.3 Hz, 1H), 7.91 (dd, J=1.8, 8.3 Hz, 1H), 7.82 (m, 2H); MS (M+) 286; Anal. Calc'd. for $C_{14}H_7BrO_2$: C, 58.57; H, 2.46; Br, 27.83; O, 11.14. Found: C, 58.88; H, 2.39; Br, 27.80; O, 10.93.

Example 5

Synthesis of Compound 105

2-Bromo biphenyl (9.0 mL, 52 mmol) was dissolved in dried tetrahydrofuran (100 mL) under a nitrogen atmosphere at room temperature. The solution was cooled to −78° C. in a cooling bath, and t-butyl lithium (40 mL, 1.7 M pentane solution) was slowly added thereto. After stirring at the same temperature for 1 hour, Compound 104 (4.9 g, 17 mmol) was added to the mixture. The cooling bath was removed, and the mixture was stirred for about 3 hours at room temperature. Aqueous ammonium chloride solution was added to the mixture, which was then extracted with methylene chloride. The organic extract was dried over magnesium sulfate and concentrated under reduced pressure. The concentrated solid was dispersed in ethanol, which was stirred for 1 hour, filtered off with suction, and washed with ethanol. After drying, Compound 105 (9.50 g, 94%) was obtained.

Example 6

Synthesis of Compound 106

Compound 105 (6.00 g, 10.1 mmol) was dispersed in 300 mL of acetic acid under a nitrogen atmosphere. Potassium iodide (16.8 g, 101 mmol) and sodium hypophosphite hydrate (17.7 g, 167 mmol) were added thereto. The resulting mixture was agitated while boiling for 3 hours. After cooling to room temperature, the mixture was filtered and washed with water and methanol, and then vacuum dried to obtain Compound 106 (5.0 g, 88%) in a light yellow color.

Example 7

Synthesis of Compound 107

Compound 105 (9.5 g, 16 mmol) was dispersed in 100 mL of acetic acid. 5 drops of concentrated sulfuric acid were added to the dispersion. The mixture was refluxed for 3 hours, and then was cooled to room temperature. Precipitate was filtered, washed with acetic acid, and then washed with water and ethanol in this order. After drying, the solid was purified by sublimation to obtain Compound 107 (8.0 g, 89%) in a white solid form.

Example 8

Synthesis of Compound 108

Compound 107 (10.0 g, 17.9 mmol) was completely dissolved in 150 mL of dry THF under a nitrogen atmosphere at room temperature. The solution was cooled to −78° C. in a cooling bath, and t-butyl lithium (31.5 mL, 1.7 M pentane solution) was slowly added thereto. The mixture had been stirred for about 1 hour at the same temperature for 1 hour, to which trimethylborate (8 mL, 71.5 mmol). Then, the cooling bath was removed, and the resulting mixture was stirred at room temperature for 3 hours. The mixture was quenched with 2 N hydrochloric acid solution (100 mL) and stirred at room temperature for 1.5 hours. Precipitate was filtered, washed with water and diethyl ether in this order, and dried in vacuo. After drying, the crude product was dispersed in diethyl ether, stirred for 2 hours, filtered, and dried to obtain Compound 108 (7.6 g, 81%) in white.

Example 9

Synthesis of Compound 109

2-Bromonaphthalene (11.0 g, 53.1 mmol) was dissolved in dry tetrahydrofuran (100 mL) under a nitrogen atmosphere at room temperature. The solution was cooled to −78° C. in a cooling bath, and t-butyllithium (47.0 mL, 1.7 pentane solution) was slowly added thereto. The mixture was stirred at the same temperature for about 1 hour, and Compound 104 (6.31 g, 22.0 mmol) was added thereto still at the same temperature. Then the cooling bath was removed, and the mixture was stirred at room temperature for about 3 hours. To the stirred mixture an aqueous ammonium chloride solution was added. The resulting mixture was extracted with methylene chloride. The organic extract was dried over magnesium sulfate and concentrated under reduced pressure. The crude product was dissolved in diethyl ether, and then petroleum ether was added thereto. The mixture was agitated for several hours to obtain a solid compound. The solid was filtered and vacuum dried to obtain dinaphthyl dialcohol (11.2 g, 93%). The dinaphtyl dialcohol (11.2 g, 20.5 mmol) was dispersed in 600 mL of acetic acid under a nitrogen atmosphere, to which potassium iodide (34.2 g, 206 mmol) and sodium hypophosphite hydrate (36.0 g, 340 mmol) were added. The resulting mixture was agitated while boiling for about 3 hours. After cooling to room temperature, the mixture was filtered and washed with water and methanol, and then vacuum dried to obtain Compound 109 (10.1 g, 96%) a light yellow color.

Example 10

Synthesis of Compound 110

To a suspension of 2-bromothiophene (8.42 g, 51.6 mmol), phenylboronic acid (9.44 g, 77.4 mmol), and sodium carbonate (16.4 g, 155 mmol) in a mixture of toluene (100 mL) and water (50 mL) was added tetrakis(triphenylphosphine)palladium (1.80 g, 1.55 mmol). The mixture was stirred at reflux for about 24 hours. Then, the resulting mixture was cooled to room temperature, and 1 N hydrochloric acid (100 mL) was added thereto. From the mixture, the organic layer was separated. The aqueous layer was extracted with ethyl acetate (3×100 mL). The combined organic extracts were dried over $MgSO_4$ and concentrated in vacuo. Purification by column chromatography afforded Compound 110 as a white solid (6.27 g, 76%). The analysis result of the compound is: 1H NMR (300 MHz, $CDCl_3$), 7.60 (m, 2H), 7.44-7.23 (m, 5H), 7.05 (m, 1H); MS (M+H) 161.

Example 11

Synthesis of Compound 111

To a solution of Compound 110 (5.00 g, 31.2 mmol) in a mixture of chloroform (80 ml) and acetic acid (80 ml) was added N-bromosuccimide (5.60 g, 31.2 mmol) at 0° C. Then the mixture was heated to 60° C. and was stirred for about 1 hour at that temperature. The mixture then was cooled to room temperature and was stirred for about 24 hours. Thereafter, the mixture was quenched with aqueous potassium hydroxide solution and extracted with chloroform. The organic layer was dried over $MgSO_4$ and concentrated in vacuo. Purification by recrystallization from ethanol afforded Compound 4-11 (3.66 g, 49%): MS (M+) calculated for $C_{50}H_{29}Br_2N$ 238, found 238.

Example 12

Synthesis of Compound 112

To a solution of Compound 111 (2.50 g, 10.4 mmol) in dry THF (50 ml) was added dropwise n-BuLi (8.4 mL of a 2.5 M solution in hexane) at −78° C. under nitrogen atmosphere. After the mixture had been stirred for about 1 hour, trimethylborate (2.40 mL, 20.9 mmol) was added dropwise at −78° C. After about 30 minutes, the cooling bath was removed, and the mixture then was stirred for about 3 hours at room temperature. The mixture was quenched with 1 N HCl (100 ml) and extracted with ethyl acetate. The organic layer was dried over magnesium sulfate and concentrated in vacuo. The crude product was slurried in petroleum ether, filtered off with suction, and dried to obtain of Compound 112 (1.04 g, 48.8%).

Example 13

Synthesis of Compound 113

Compound 111 (1.00 g, 4.18 mmol) was dissolved in dried tetrahydrofuran (30 mL) at room temperature under a nitrogen atmosphere. The solution then was cooled to −78° C. in a cooling bath, and t-butyl lithium (3.3 mL, 1.7 M pentane solution) was slowly added to the solution at that temperature. The mixture was stirred for about 1 hour at the same temperature, and Compound 104 (0.4 g, 1.4 mmol) was added thereto. After stirring for 30 minutes at −78° C., the cooling bath was removed, and the mixture was further stirred for about 3 hours at room temperature. The mixture was quenched with 1 N HCl (50 ml) and extracted with diethyl ether. The organic layer was dried over magnesium sulfate and concentrated in vacuo. The crude product was slurried in petroleum ether, filtered off with suction, and dried to obtain Compound 113 (0.70 g, 82%).

Example 14

Synthesis of Compound 114

Compound 113 (0.71 g, 1.15 mmol) was dispersed in 15 mL of acetic acid under a nitrogen atmosphere. Potassium iodide (1.91 g, 11.5 mmol) and sodium hypophosphite hydrate (2.02 g, 23.0 mmol) were added to the dispersion. The resulting mixture was stirred while boiling for about 3 hours. The boiled mixture was cooled to room temperature. The mixture was filtered and washed with water and methanol, and then vacuum dried to obtain Compound 114 (0.57 g, 86.9%): MS [M+] 572.

Example 15

Synthesis of Compound 115

9-Bromoanthracene (1.90 g, 7.35 mmol), Compound 112 (1.80 g, 8.82 mmol) and sodium carbonate (2.34 g, 22.1 mmol) were suspended in a mixture of toluene (20 mL), ethanol (3 mL) and water (10 mL). Tetrakis(triphenylphosphine)palladium (0.25 g, 0.22 mmol) was added to the suspension. The mixture was stirred at reflux for about 24 hours, and then the refluxed mixture was cooled to room temperature. The organic layer was separated and washed with water, and the aqueous layer was extracted with chloroform. The organic extract was dried over $MgSO_4$ and concentrated in vacuo to give Compound 115 (2.10 g, 84%).

Example 16

Synthesis of Compound 116

To a solution of Compound 4-15 (2.10 g, 6.24 mmol) in dry $CCl_4$ (60 ml) was added dropwise bromine (0.32 mL, 6.24 mmol) at 0° C. After the reaction mixture had been stirred for about 3 hours at room temperature, it was quenched with saturated aqueous sodium bicarbonate solution. The organic layer was separated, and the aqueous layer was extracted with chloroform. The combined organic extracts were dried over $MgSO_4$ and concentrated in vacuo. Purification by column chromatography (1:4 THF-hexane) and recrystallization from ethanol afforded Compound 116 (0.92 g, 35%).

Example 17

Synthesis of Compound 117

5,5'-dibromo-2,2'-bothiophene (5.00 g, 15.4 mmol), phenylboronic acid (2.07 g, 17.0 mmol) and sodium carbonate (4.90 g, 46.3 mmol) were suspended in a mixture of toluene (30 mL) and water (15 mL). Tetrakis(triphenylphosphine) palladium (0.50 g, 0.46 mmol) was added to the suspension. The resulting mixture was stirred at reflux for about 24 hours. The refluxed mixture was cooled to room temperature and was extracted with chloroform. The organic extract was dried over $MgSO_4$ and concentrated in vacuo. Purification by column chromatography (n-hexane) afforded Compound 117 (2.80 g, 57%).

Example 18

Synthesis of Compound 118

To a solution of Compound 4-17 (6.71 g, 20.9 mmol) in dry THF (100 ml) was added dropwise t-BuLi (18.0 mL of a 1.7 M solution in pentane) at −78° C. under nitrogen. After the mixture had been stirred for about 1 hour, trimethylborate (4.68 g, 41.8 mmol) was added thereto dropwise at −78° C. After 30 minutes, the cooling bath was removed, and the mixture was stirred for about 3 hours at room temperature. The mixture was quenched with 1 N HCl and diethyl ether was added. Precipitate was filtered off with suction, washed with diethyl ether, and dried in vacuo to obtain Compound 118 (5.33 g, 89%).

Example 19

Synthesis of Compound 119

5,5'-dibromo-2,2'-bothiophene (5.00 g, 15.4 mmol), naphthalene-2-boronic acid (1.86 g, 10.8 mmol) and potassium carbonate (30 mL, 2 M aqueous solution) were suspended in THF (50 mL). Tetrakis(triphenylphosphine)palladium (0.18 g, 0.16 mmol) was added to the suspension. The resulting mixture was stirred at reflux for about 24 hours and thereafter cooled to room temperature. Precipitate was filtered off with suction. The crude product was dissolved in THF, filtered, and washed with THF. The filtrate was concentrated in vacuo and recrystallized from ethyl acetate to give Compound 119 (2.60 g, 45%).

Example 20

Synthesis of Compound 120

Compound 4-9 (5.00 g, 9.81 mmol), bis(pinacolato)diboron (2.75 g, 10.9 mmol) and potassium acetate (2.89 g, 29.4 mmol) were suspended in dioxane (50 mL). Palladium (diphenylphosphinoferrocene)chloride (0.24 g, 3 mol %) was added to the suspension. The resulting mixture was stirred at 80° C. for about 6 hours, and cooled to room temperature. The mixture was diluted with water (50 mL) and extracted with dichloromethane (3×50 mL). The organic extracts were dried over $MgSO_4$ and concentrated in vacuo. The crude product was washed with ethanol and dried in vacuo to afford Compound 120 (5.46 g, 92%).

Example 21

Synthesis of Compound 121

To a solution of 2,2'-dibromothiophene (2.70 g, 8.30 mmol) in dry THF (50 ml) at −78° C. in a cooling bath was added dropwise t-BuLi (6.0 mL of a 1.5 M solution in pentane) under a nitrogen atmosphere. After the mixture had been stirred for 1 hour, triphenylboranyl chloride (2.35 g, 8.00 mmol) was added dropwise at −78° C. The cooling bath was removed, and the mixture was stirred for about 3 hours at room temperature. The mixture was quenched with aqueous saturated NaCl solution (50 mL) and stirred at room temperature for about 10 minutes. The organic layer was separated,

Example 22

Synthesis of Compound 122

To a solution of 2-chloroanthraquinone (3.00 g, 12.3 mmol) in THF (100 mL) were added thiophene-2-boronic acid (2.00 g, 15.6 mmol), 2 M potassium carbonate solution (20 mL), and tetrakis(triphenylphosphine)palladium (0.14 g). The mixture was stirred at reflux for about 48 hours and then was cooled to room temperature. Precipitate was filtered off with suction, washed with water and ethanol, and dried in vacuo. Purification by recrystallization from ethyl acetate afforded thiophene-2-anthraquinone (1.70 g, 47%). The thiophene-2-anthraquinone (1.70 g, 5.85 mmol) was dissolved in a mixture of chloroform (30 ml) and acetic acid (5 ml). N-bromosuccimide (1.04 g, 5.85 mmol) was added to the thiophene-2-anthraquinone solution at room temperature. After the reaction mixture had been stirred for about 4 hours at room temperature, precipitate was filtered, washed with water, and dried in vacuo to afford Compound 122 (1.80 g, 87%).

Example 23

Synthesis of Compound 123

To a solution of Compound 122 (1.80 g, 4.87 mmol) in THF (100 mL) were added 4-formylphenylboronic acid (1.00 g, 6.91 mmol), 2 M potassium carbonate solution (30 mL), and tetrakis(triphenylphosphine)palladium (0.05 g, 0.04 mmol)). The mixture was stirred at reflux for about 72 hours and then was cooled to room temperature. Precipitate was filtered off with suction, washed with water and ethanol, and dried in vacuo to give 2-(2-anthraquinone)-5-(4-formylphenyl)thiophene (1.70 g, 89%). The 2-(2-anthraquinone)-5-(4-formylphenyl)thiophene (1.70 g, 4.31 mmol) was mixed with N-phenyl-1,2-phenylenediamine (0.87 g, 4.74 mmol) in a mixture of 50 mL of toluene and 5 mL of acetic acid. The resulting mixture was refluxed for about 16 hours and cooled to room temperature. The formed solid was filtered, washed with acetic acid, and dried to obtain a solid of Compound 123 (0.75 g, 32%).

Example 24

Synthesis of Compound 4

Compound 106 (1.00 g, 1.796 mmol), Compound 112 (0.55 g, 2.67 mmol) and sodium carbonate (0.57 g, 5.34 mmol) were suspended in a mixture of toluene (20 mL), ethanol (3 mL) and water (10 mL). Tetrakis(triphenylphosphine)palladium (0.06 g, 0.05 mmol) was added to the suspension. The resulting mixture was stirred at reflux for about 48 hours and then cooled to room temperature. The organic layer was separated, and the aqueous layer was extracted with chloroform. The combined organic extracts were dried over $MgSO_4$ and concentrated in vacuo. Purification by column chromatography (chloroform/n-hexane=1/5) afforded Compound 4 (0.50 g, 44%): mp 113.17° C.; $^1$H NMR (300 MHz, $CDCl_3$) 7.75 (s, 1H), 7.64-7.46 (m, 12H), 7.44-7.28 (m, 4H), 7.26-7.18 (m, 5H), 6.99 (t, 4H), 6.86 (d, 6H); MS [M+H] 641; Anal. Calcd for $C_{48}H_{32}S$: C, 89.96; H, 5.03; S, 5.00. Found: C, 90.82; H, 5.17; S, 4.8.

Example 27

Synthesis of Compound 12

Compound 109 (1.00 g, 1.96 mmol), Compound 118 (0.84 g, 2.94 mmol) and sodium carbonate (0.62 g, 5.88 mmol) were suspended in a mixture of toluene (50 mL), ethanol (5 mL) and water (25 mL). Tetrakis(triphenylphosphine)palladium (0.05 g, 0.05 mmol) was added to the suspension. The resulting mixture was stirred at reflux for about 48 hours and then cooled to room temperature. The organic layer was separated and the aqueous layer was extracted with chloroform. The combined organic extracts were dried over $MgSO_4$ and concentrated in vacuo. Purification by column chromatography (chloroform/n-hexane=1/2) afforded Compound 12 (0.83 g, 63%): mp 304.49° C.; MS [M+H] 671.

Example 25

Synthesis of Compound 14

Compound 106 (0.85 g, 1.51 mmol), Compound 118 (0.65 g, 2.27 mmol) and sodium carbonate (0.48 g, 5.53 mmol) were suspended in a mixture of toluene (40 mL), ethanol (5 mL) and water (20 mL). Tetrakis(triphenylphosphine)palladium (0.05 g, 0.05 mmol) was added to the suspension. The resulting mixture was stirred at reflux for about 48 hours and then cooled to room temperature. The organic layer was separated and the aqueous layer was extracted with chloroform. The combined organic extracts were dried over $MgSO_4$ and concentrated in vacuo. Purification by column chromatography (chloroform/n-hexane=1/4) afforded a compound of the Compound 14 (0.70 g, 64%): mp 117.86° C.; MS [M+H] 723.

Example 26

Synthesis of Compound 19

Compound 103 (1.00 g, 1.80 mmol), Compound 118 (1.23 g, 4.31 mmol) and sodium carbonate (1.14 g, 10.8 mmol) were suspended in a mixture of toluene (40 mL), ethanol (5 mL) and water (10 mL). Tetrakis(triphenylphosphine)palladium (0.05 g, 0.05 mmol) was added to the suspension. The resulting mixture was stirred at reflux for about 48 hours and then cooled to room temperature. The organic layer was separated and the aqueous layer was extracted with chloroform. The combined organic extracts were dried over $MgSO_4$ and concentrated in vacuo. Purification by column chromatography (chloroform/n-hexane=1/2) afforded Compound 19 (0.18 g, 10%): mp 326.07° C.; MS [M+H] 963; Anal. Calcd for $C_{66}H_{42}S_4$: C, 82.29; H, 4.39; S, 13.31. Found: C, 80.89; H, 4.39; S, 12.70.

Example 29

Synthesis of Compound 21

A mixture of Compound 108 (1.34 g, 2.56 mmol), Compound 116 (0.80 g, 1.93 mmol), potassium phosphate (0.82 g, 3.86 mmol) and tetrakis(triphenylphosphine)palladium (0.07 g, 0.06 mmol) in DMF (25 mL) was prepared. The mixture was stirred at 80° C. for about 48 hours and then cooled to room temperature. Precipitate was filtered off with suction, washed with water and methanol, and then vacuum dried to obtain Compound 21 (1.10 g, 53%): mp 438.50° C.; MS [M+H] 815.

Example 28

Synthesis of Compound 23

A mixture of Compound 108 (0.45 g, 0.86 mmol), Compound 114 (0.45 g, 0.78 mmol), potassium phosphate (0.33 g, 1.56 mmol), and tetrakis(triphenylphosphine)palladium (0.03 g, 0.02 mmol) in DMF (10 mL) was prepared. The mixture was stirred at 80° C. for about 48 hours and cooled to room temperature. Precipitate was filtered off with suction, washed with water and methanol, and then vacuum dried to obtain Compound 23 (0.30 g, 36%): mp 396.70° C.; MS [M+H] 973.

Example 30

Synthesis of Compound 25

Compound 120 (4.50 g, 5.39 mmol), Compound 119 (2.00 g, 5.39 mmol) and 2 N potassium carbonate (20 mL) were suspended in a mixture of toluene (50 mL) and ethanol (20 mL). Tetrakis(triphenylphosphine)palladium (0.13 g) was added to the suspension. The resulting mixture was stirred at reflux for about 15 hours and then cooled to room temperature. Precipitate was filtered off with suction, washed with water and ethanol, and then vacuum dried to obtain Compound 25 (3.38 g).

Example 31

Synthesis of Compound 27

Compound 121 (1.00 g, 2.00 mmol), Compound 120 (1.10 g, 2.00 mmol) and 2 M sodium carbonate (2 mL) were suspended in THF (25 mL). Tetrakis(triphenylphosphine)palladium (0.02 g, 0.02 mmol) was added to the suspension. The resulting mixture was stirred at reflux for about 10 hours and then cooled to room temperature. The mixture was extracted with THF. The organic extract was dried over $MgSO_4$ and concentrated in vacuo. Purification by column chromatography (chloroform/n-hexane=1/5) afforded Compound 27 (1.20 g, 70%): mp 156.4° C.; MS [M+H] 853.

Example 32

Synthesis of Compound 29

2-Bromonaphthalene (0.83 g, 4.03 mmol) was dissolved in dried THF (40 mL) under a nitrogen atmosphere. The solution was cooled to −78° C. in a cooling bath, and t-butyl lithium (3.15 mL, 1.7 M pentane solution) was slowly added to the chilled solution over 10 minutes. The mixture had been stirred for about 40 minutes at −78° C. Then, Compound 123 (0.75 g, 1.75 mmol) was added thereto, and the resulting mixture was further stirred for about 3 hours at −78° C. Thereafter, the cooling bath was removed and the mixture was stirred at room temperature for about 1 hour. The mixture was quenched with aqueous ammonium chloride solution (50 mL). The organic layer was separated and the aqueous layer was extracted with diethyl ether (40 mL). The combined organic extracts were dried over magnesium sulfate and concentrated under reduced pressure. The obtained solid was dispersed in diethyl ether, stirred for 1 hour, filtered off with suction. After drying, a dialcohol compound (0.80 g, 73%) was obtained.

The dialcohol compound (0.80 g, 0.98 mmol) was dispersed in acetic acid (100 mL) under a nitrogen atmosphere. Potassium iodide (1.66 g, 10 mmol) and sodium hypophosphite hydrate (1.76 g, 20 mmol) were added to the dispersion. The mixture was boiled for about 3 hours with continuous stirring and then cooled to room temperature. The mixture was filtered and washed with water, and then vacuum dried to obtain Compound 29 (0.80 g).

Example 33

Organic EL Device with Light-Emitting Layer Using Compound 12

A glass substrate coated with about 1500 Å of ITO (indium tin oxide) was cleaned in an ultrasonic bath filled with a detergent solution. After the ultrasonic cleaning for about 30 minutes, the substrate was washed with distilled water twice for about 10 minutes each time to remove remaining detergent from the substrate. The substrate was further cleaned with in the order of isopropyl alcohol, acetone and methanol in an ultrasonic bath. After drying the in the air, the substrate was transferred into a plasma cleaning chamber connected with a thermal vacuum evaporator. The substrate was further cleaned in an oxygen plasma condition for about 5 minutes and the cleaning chamber was evacuated by a turbo-molecular pump to transfer the substrate to the thermal vacuum evaporator.

Over the ITO film as the anode, about 500 Å of hexanitrile hexaazatriphenylene was deposited as a hole-injecting material by thermal vacuum evaporation at about $5\times10^{-7}$ torr. About 600 Å of NPB, a hole-transporting material, was deposited on the hole-injecting layer, which was followed by the deposition of about 200 Å thickness of Compound 12 as the light-emitting material. On top of the light-emitting layer, about 300 Å of Compound 301 (2-[4-[(N-phenylbenzimidazol-2-yl)phenyl-9,10-bis(2-naphtyl)anthracene) was formed as an electron-transporting and/or electron-injecting layer. Then, about 5 Å thickness of lithium fluoride and about 2500 Å of aluminum were deposited on the electron-transporting/injecting layer to form a LiF/Al bilayer cathode. The deposition rates of the organic materials were maintained at about 1 Å/sec, for the lithium fluoride at about 0.2 Å/sec and for the aluminum at about 3~7 Å/sec.

Compound 301

When 3.3 V of forward bias was applied across the device, at 10 mA/cm² of current density, 358 nit of green emission corresponding to x=0.30, y=0.56 of the 1931 CIE color coordination was observed. At 50 mA/cm² of constant DC current density, it took 54.6 hours until the brightness drops to 90% level of the initial brightness.

Example 34

Organic EL Device with Light-Emitting Layer Using Compound 21

An organic light-emitting diode was fabricated in the same manner in as described in Example 33 except that Compound 21 and Alq3 were used as the light-emitting material and electron transporting/injecting material respectively instead of Compound 12 and Compound 301. When 5.66 V of forward bias was applied across the resulting device, at 10 mA/cm² of current density, 151 nit of green emission corresponding to x=0.20, y=0.44 of the 1931 CIE color coordination was observed. At 50 mA/cm² of constant DC current density, it took 11.9 hours until the brightness drops to 90% level of the initial brightness.

Example 35

Organic EL Device with Light-Emitting Layer Using Compound 19

An organic light-emitting diode was fabricated in the same manner in as described in Example 34 except that Compound 19 was used as the light-emitting material instead of Compound 21. When 3.74 V of forward bias was applied across the device, at 10 mA/cm² of current density, 404 nit of green emission corresponding to x=0.39, y=0.57 of the 1931 CIE color coordination was observed. At 50 mA/cm² of constant DC current density, it took 19.8 hours until the brightness drops to 90% level of the initial brightness.

Example 36

Organic EL Device with Light-Emitting Layer Using Compound 14

An organic light-emitting diode was fabricated in the same manner in as described in Example 34 except that Compound 14 was used as the light-emitting material instead of Compound 21. When 4.06 V of forward bias was applied across the device, at 10 mA/cm² of current density, 486 nit of green emission corresponding to x=0.28, y=0.58 of the 1931 CIE color coordination was observed. At 50 mA/cm² of constant DC current density, it took 10.6 hours until the brightness drops to 90% level of the initial brightness.

Example 37

Organic EL Device with Light-Emitting Layer Using Compound 12 and DCJTB

An organic light-emitting diode was fabricated in the same manner in as described in Example 33 except that DCJTB (2 wt. %) was co-deposited with Compound 12 in which Compound 12 serves as a host and DCJTB service a dopant. When 3.26 V of forward bias was applied across the device, at 10 mA/cm² of current density, 404 nit of red emission corresponding to x=0.59, y=0.40 of the 1931 CIE color coordination was observed. At 50 mA/cm² of constant DC current density, it took 132.5 hours until the brightness drops to 90% level of the initial brightness.

Example 38

Organic EL Device with Light-Emitting Layer Using Alq3

An organic light-emitting diode was fabricated in the same manner in as described in Example 33 except that 500 Å of Alq3 was deposited in replace of both the light-emitting layer of Compound 12 and the electron-transporting/injecting layer of Compound 301. When 5.20 V of forward bias was applied across the device, at 10 mA/cm² of current density, 326 nit of green emission corresponding to x=0.33, y=0.53 of the 1931 CIE color coordination was observed. At 50 mA/cm² of constant DC current density, it took 1 hour until the brightness drops to 90% level of the initial brightness.

Discussion of Stability of Organic EL Devices

As briefly noted above, electrical stability of materials used in light-emission is one of the very important characteristics in that it can determine the lifetime and driving voltage of organic EL devices. For example, if light-emitting material of an organic EL device is not electrically stable, the material may decompose during the course of electroluminescence processes, resulting in drop of brightness and requiring higher driving voltage. It has been known that Alq3 is very stable among organic EL compounds used in organic EL devices.

Electrical stability of organic EL compounds are normally determined or compared in terms of the time period for which brightness of light emission from a light-emitting layer made of a material drops to a certain level, for example 90% of the initial brightness, when a constant current density is applied to the device. In Examples 33-38, the time for 10% of initial brightness drop was measured for organic EL devices having various light-emitting materials. Examples 33-37 used compounds satisfying Formula I in light-emitting layers whereas Example 38 used Alq3. The time for the 10% drop of the initial brightness in Examples 33-37 are extraordinarily higher than that of Alq3 of Example 38. The use of organic compounds satisfying Formula I in organic EL devices, particularly as the light-emitting material would substantially improve organic EL devices in respect of driving voltage and device lifetime.

What is claimed is:

1. An organic electroluminescent ("EL") device comprising of an anode; a cathode; and at least one layer located between the anode and the cathode, wherein the layer comprises a light-emitting layer having a light-emitting the compound of the Formula I generating visible light of colors ranging from green to red:

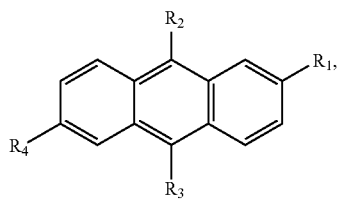

Formula I wherein at least one of R1 through R4 is represented by Formula II:

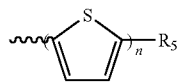

Formula II wherein n is an integer from 1 to 10, and wherein R5 and each of R1-R4 that is not Formula II are non double-spiral substituent groups selected from the group consisting of: hydrogen; halo; hydroxyl; mercapto; cyano; nitro; carbonyl; carboxyl; formyl; substituted or unsubstituted C1-C20 alkyl; substituted or unsubstituted C2-C10 alkenyl; substituted or unsubstituted C2-C7 alkynyl; substituted or unsubstituted aryl; substituted or unsubstituted heteroaryl; substituted or unsubstituted C3-C7 cycloalkyl, in which a carbon atom in the ring can optionally be replaced by an oxygen, nitrogen or sulfur atom; substituted or unsubstituted C4-C7 cycloalkenyl, in which a carbon atom in the ring can be optionally replaced by an oxygen, nitrogen or sulfur atom; substituted or unsubstituted C1-C20 alkoxy; substituted or unsubstituted C2-C10 alkenyloxy; substituted or unsubstituted C2-C7 alkynyloxy; substituted or unsubstituted aryloxy; substituted or unsubstituted C1-C20 alkylamine; substituted or unsubstituted C2-C10 alkenylamine; substituted or unsubstituted C2-C7 alkynylamine; substituted or unsubstituted arylamine; substituted or unsubstituted alkylarylamine; substituted or unsubstituted C1-C20 alkylsilyl; substituted or unsubstituted C2-C10 alkenylsilyl; substituted or unsubstituted C2-C7 alkynylsilyl; substituted or unsubstituted arylsilyl; substituted or unsubstituted alkylarylsilyl; substituted or unsubstituted C1-C20 alkylboranyl; substituted or unsubstituted C2-C10 alkenylboranyl; substituted or unsubstituted C2-C7 alkynylboranyl; substituted or unsubstituted arylboranyl; substituted or unsubstituted alkylarylboranyl; substituted or unsubstituted C1-C20 alkylthio; substituted or unsubstituted C2-C10 alkenylthio; substituted or unsubstituted C2-C7 alkynylthio; and substituted or unsubstituted arylthio groups; and wherein R1 and R4 are different when both R1 and R4 are not Formula II.

2. The EL device of claim 1, wherein R5 and each of R1-R4 that is not Formula II are selected from the group consisting of: hydrogen, cyano, nitro, substituted or unsubstituted C1-20 alkyl, substituted or unsubstituted C2-C10 alkenyl, substituted or unsubstituted C3-C7 cycloalkyl, substituted or unsubstituted C4-C7 cycloalkenyl, substituted or unsubstituted aryl, substituted or unsubstituted heteroaryl, substituted or unsubstituted C1-C20 alkoxy, substituted or unsubstituted aryloxy, substituted or unsubstituted C1-C20 alkylamine, substituted or unsubstituted arylamine, substituted or unsubstituted alkylarylamine, substituted or unsubstituted C1-C20 alkylsilyl; substituted or unsubstituted arylsilyl; substituted or unsubstituted alkylarylsilyl, substituted or unsubstituted C1-C20 alkylboranyl, substituted or unsubstituted arylboranyl, substituted or unsubstituted alkylarylboranyl, substituted or unsubstituted C1-C20 alkylthio, and substituted or unsubstituted arylthio groups.

3. The EL device of claim 1, wherein the substituent groups are further mono- or poly-substituted with identical or different substituent groups selected from the group consisting of: halo, hydroxyl, mercapto, cyano, nitro, amino, carbonyl, carboxyl, formyl, C1-C20 alkyl, C2-10 alkenyl, C2-C7 alkynyl, aryl, heteroaryl, C3-C7 cycloalkyl, 3-7 membered heterocyclic saturated or unsaturated ring, acryl, C1-C20 alkoxy, C2-C10 alkenyloxy, C2-C7 alkynyloxy, C1-C20 alkylamine, C2-C10 alkenylamine, C2-C7 alkynylamine, arylamine, alkylarylamine, C1-C20 alkylsilyl, C2-C10 alkenylsilyl, C2-C7 alkynylsilyl, alkoxysilyl, arylsilyl, alkylarylsilyl, C1-C20 alkylboranyl, C2-C10 alkenylboranyl, C2-C7 alkynylboranyl, arylboranyl, alkylarylboranyl, C1-C20 alkylthio, C2-C10 alkenylthio, C2-C7 alkynylthio and arylthio groups.

4. The EL device of claim 1, wherein the substituent groups are further mono- or poly-substituted with identical or different substituent groups selected from the group consisting of: cyano, nitro, formyl, methyl, ethyl, proply, phenyl, naphthyl, biphenyl, anthracenyl, imidazolyl, thiazolyl, oxazolyl, thiophenyl, pyridyl, pyrimidyl, pyrrolyl, cyclobutenyl, cyclopetenyl, methoxy, ethoxy, propoxy, phenoxy, naphthoxy, methylamine, ethylamine, propylamine, phenylamine, naphthylamine, methylphenylamine, ethylphenylamine, ethylnaphthylamine, dimethylboranyl, diethylboranyl, dipropylboranyl, diphenylboranyl, dinaphthylboranyl, phenylnaphthylboranyl, phenylmethylboranyl, naphthylmethylboranyl, naphthylethylboranyl, trimethylsilyl, triethylsilyl, tripropylsilyl, triphenylsilyl, trinaphthylsilyl, dimethylphenylsilyl, diethylphenylsilyl, diphenylmethylsilyl, methylthio, ethylthio, propylthio, butylthio, phenylthio and naphthylthio groups.

5. The EL device of claim 1, wherein the C3-C7 cycloalkyl and C4-C7 cycloalkenyl groups are C5-C7 cycloalkyl and C5-C7 cycloalkenyl groups respectively, and are 5-6 membered, unsubstituted or substituted, saturated or unsaturated heterocyclic rings.

6. The EL device of claim 1, wherein R5 and each of R1-R4 that is not Formula II are selected from the group consisting of: methyl, ethyl, propyl, butyl, isopropyl, n-butyl, t-butyl, isobutyl, n-pentyl, neo-pentyl, n-hexyl, ethenyl, propenyl, butenyl, pentenyl, hexenyl, 2-methyl-ethenyl, 2-methyl-propenyl, 2-methyl-butenyl, 2-methyl-pentenyl, 2-methyl-hexenyl, imidazolyl, thiazolyl, oxazoly, thiophenyl, pyridyl, pyrimidyl, pyrrolyl, 2-methylimidazolyl, 2-methylthiazolyl, 2-methyloxazoly, 2-methylthiophenyl, 2-methylpyridyl, 2-methylpyrimidyl, 2-methylpyrrolyl, phenyl, naphthyl, anthracenyl, biphenyl, terphenyl, tetracenyl, 3-methyl-phenyl, 4-methyl-naphthyl, 9-methyl-anthracenyl, 4-methyl-tetracenyl, 2-methyl-imidazolyl, 2-methyl-oxazolyl, 2-methyl-thiazolyl, 2-methyl-furanyl, 2-methyl-thiophenyl, 2-methyl-pyrazolyl, 2-methyl-pyridyl, 2-methyl-pyrimidinyl, methoxy, ethoxy, propoxy, butoxy, pentoxy, hexoxy, isopropoxy, isobutoxy, t-butoxy, neo-pentoxy, phenoxy, naphthoxy, biphenoxy, 3-methyl-phenoxy, 4-methyl-naphthoxy, 2-methyl-biphenoxy, methylamine, ethylamine, propylamine, butylamine, pentylamine, hexylamine, heptylamine, isopropylamine, isobutylamine, t-butylamine, 2-pentylamine, neopentylamine, phenylamine, naphthylamine, biphenylamine, anthracenylamine, 3-methyl-phenylamine, 4-methyl-naphthylamine, 2-methyl-biphenylamine, 9-methyl-anthracenylamine, phenylmethylamine, phenylethylamine, naphthylmethylamine, naphthylethylamine, biphenylmethylamine, 3-methyl-phenylmethylamine, phenylisopropylamine, naphthylisopropylamine, naphthylisobutylamine, biphenylisopropylamine, trimethylsilyl, triethylsilyl, tributylsilyl, tri(isopropyl)silyl, tri(isobutyl)silyl, tri(t-butyl)silyl, tri(2-butyl)silyl, triphenylsilyl, trinaphthylsilyl, tribiphenylsilyl, tri(3-methylphenyl)silyl, tri(4-methylnaphthyl)silyl, tri(2-methylbiphenyl)silyl, phenylmethylsilyl, phenylethylsilyl, naphthylmethylsilyl, naphthylethylsilyl, biphenylmethylsilyl, 3-methyl-phenylmethylsilyl, phenylisopropylsilyl, naphthylisopropylsilyl, naphthylisobutylsilyl, biphenylisopropylsilyl, dimethylboranyl, diethylboranyl, dipropylamine, dibutylamine, dipentylamine, diisopropylboranyl, diisobutylboranyl, di(t-butyl)boranyl, isopropylisobutylamine, diphenylboranyl, dinaphthylboranyl, dibiphenylboranyl, di(3-methylphenyl)boranyl, di(4-methylnaphthyl)boranyl, di(2-methylbiphenyl)boranyl, phenylmethylboranyl, phenylethylboranyl, naphthylmethylboranyl, naphthylethylboranyl, biphenylmethylboranyl, 3-methyl-phenylmethylboranyl, phenylisopropylboranyl, naphthylisopropylboranyl, naphthylisobutylboranyl, biphenylisopropylboranyl, methylthio, ethylthio, propylthio, butylthio, pentylthio, hexylthio, tri(isopropyl)thio, tri(isobutyl)thio, tri(t-butyl)thio, tri(2-butyl)thio, phenylthio, naphthylthio, biphenylthio, (3-methylphenyl)thio, (4-methylnaphthyl)thio and (2-methylbiphenyl)thio groups.

7. The EL device of claim 1, wherein R5 and each of R1-R4 that is not Formula II are selected from the group consisting of: methyl, ethyl, isopropyl, t-butyl, ethenyl, propenyl, 2-methyl-ethenyl, 2-methyl-propenyl, imidazolyl, thiazolyl, oxazolyl, 2-methylimidazolyl, 2-methyithiazolyl, 2-methyloxazoly, phenyl, naphthyl, biphenyl, terphenyl, anthracenlyl, 3-methyl-phenyl, 4-methyl-naphthyl, methoxy metoxy, ethoxy, isopropoxy, isobutoxy, phenoxy, naphthoxy, 3-methyl-phenoxy, 4-methyl-naphthoxy, methylamine, ethylamine, isopropylamine, isobutylamine, t-butylamine, phenylamine, naphthylamine, 3-methyl-phenylamine, 4-methyl-naphthylamine, phenylmethylamine, phenylethylamine, naphthylmethylamine, 3-methyl-phenylmethylamine, phenylisopropylamine, trimethylsilyl, triethylsilyl, tri(isopropyl)silyl, tri(isobutyl)silyl, triphenylsilyl, trinaphthylsilyl, tri(3-methylphenyl)silyl, tri(4-methylnaphthyl)silyl, phenylmethylsilyl, phenylethylsilyl, 3-methyl-phenylmethylsilyl, phenylisopropylsilyl, dimethylboranyl, diethylboranyl, diisopropylboranyl, diisobutylboranyl, diphenylboranyl, dinaphthylboranyl, di(3-methylphenyl)boranyl, di(4-methylnaphthyl)boranyl, phenylmethylboranyl, phenylethylboranyl, 3-methyl-phenylmethylboranyl, phenylisopropylboranyl, methylthio, ethylthio, tri(isopropyl)thio, tri(isobutyl)thio, phenylthio, naphthylthio, (3-methylphenyl)thio and (4-methylnaphthyl)thio groups.

8. The EL device of claim 1, wherein R5 and each of R1-R4 that is not Formula II are selected from the group consisting of substituted or unsubstituted phenyl, substituted or unsubstituted naphthyl, substituted or unsubstituted biphenyl, substituted or unsubstituted terphenyl, and substituted or unsubstituted anthracenyl.

9. The EL device of claim 1, wherein the substituted phenyl, naphthyl, biphenyl, terphenyl, and anthracenyl are substituted with one or more selected from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio.

10. The EL device of claim 1, wherein only one of R1 through R4 is represented by Formula II.

11. The EL device of claim 1, wherein two of R1 through R4 is represented by Formula II.

12. The EL device of claim 1, wherein R1 and R4 are represented by Formula II.

13. The EL device of claim 1, wherein R2 and R3 are represented by Formula II.

14. The EL device of claim 1, wherein three of R1 through R4 is represented by Formula II.

15. The EL device of claim 1, wherein all of R1 through R4 is represented by Formula II.

16. The EL device of claim 1, wherein at least one of R1-R4 is represented by Formula II, and wherein the remaining R1-R4 is or are selected from the group consisting of:

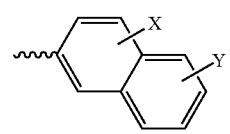

Formula 1-1

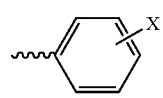

Formula 1-2

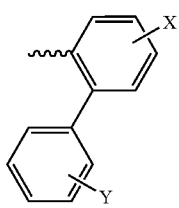

Formula 1-3

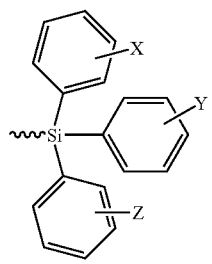

Formula 1-4

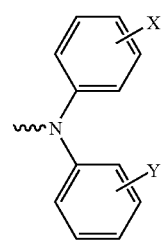

Formula 1-5

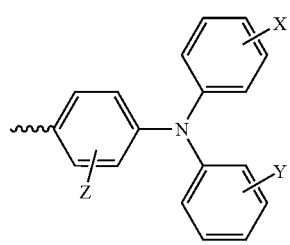

Formula 1-6

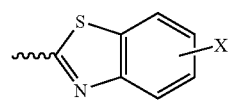

Formula 1-7

-continued

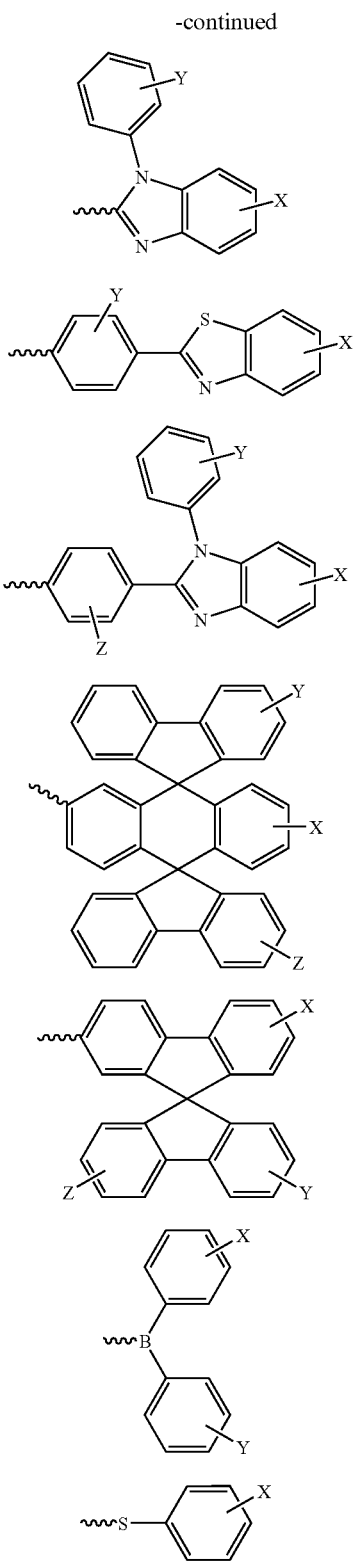

Formula 1-8

Formula 1-9

Formula 1-10

Formula 1-11

Formula 1-12

Formula 1-13

Formula 1-14 wherein X, Y and Z are identical or different substituent groups, and wherein each ring moiety where X, Y or Z is attached may be substituted with more than one, identical or different, substituent groups like X, Y or Z.

17. The EL device of claim 16, wherein X, Y and Z are selected from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio.

18. The EL device of claim 16, wherein X, Y and Z are selected from the group consisting of cyano, nitro, methyl, ethyl, isopropyl, t-butyl, methoxy, ethoxy, propoxy, methylthio, immidazolyl, pyridyl, thioazolyl, oxazolyl furanyl, thiophenyl, pyrrolyl, pyridyl and pyrimidyl.

19. The EL device of claim 16, wherein Formula II is selected from the group consisting of:

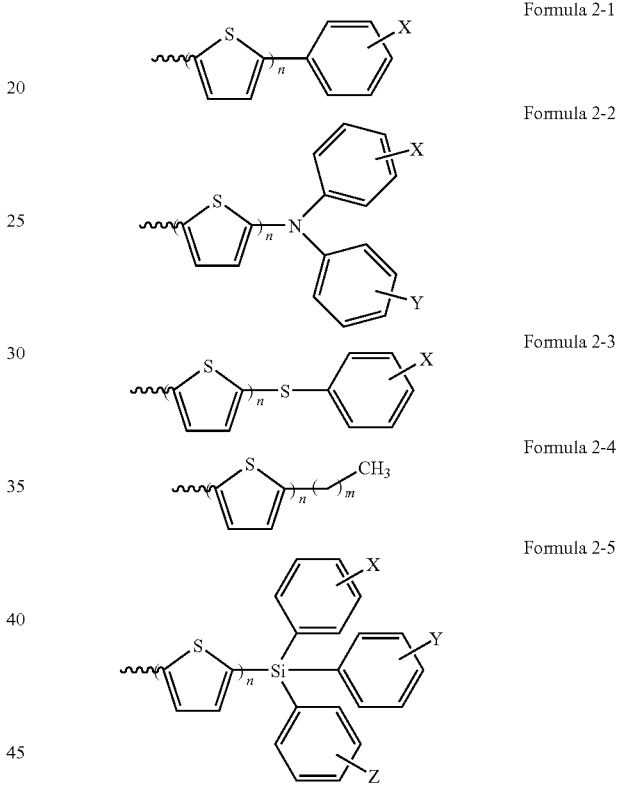

Formula 2-1

Formula 2-2

Formula 2-3

Formula 2-4

Formula 2-5 wherein n is an integer from 1 to 4;

wherein m is an integer from 0 to 20;

wherein X, Y and Z are identical or different substituent groups; and wherein each ring moiety where X, Y or Z is attached may be substituted with more than one, identical or different, substituent groups like X, Y or Z.

20. The EL device of claim 19, wherein X, Y and Z are selected from the group consisting of cyano, nitro, formyl, substituted or unsubstituted C1-C20 alkyl, aryl heteroaryl, C4-C7 cycloalkenyl, substituted or unsubstituted C1-C20 alkoxy, aryloxy, C1-C20 alkylamine, arylamine, alkylarylamine, C1-C20 silyl, arylsilyl, and alkylarylsilyl, C1-C20 alkylboranyl, arylboranyl, alkylarylboranyl, C1-C20 alkylthio and arylthio.

21. The EL device of claim 19, wherein X, Y and Z are selected from the group consisting of cyano, nitro, methyl, ethyl, isopropyl, t-butyl, methoxy, ethoxy, propoxy, methylthio, immidazolyl, pyridyl, thioazolyl, oxazolyl furanyl, thiophenyl, pyrrolyl, pyridyl and pyrimidyl.

22. The EL device of claim 1, wherein the compound is selected from the group consisting of:
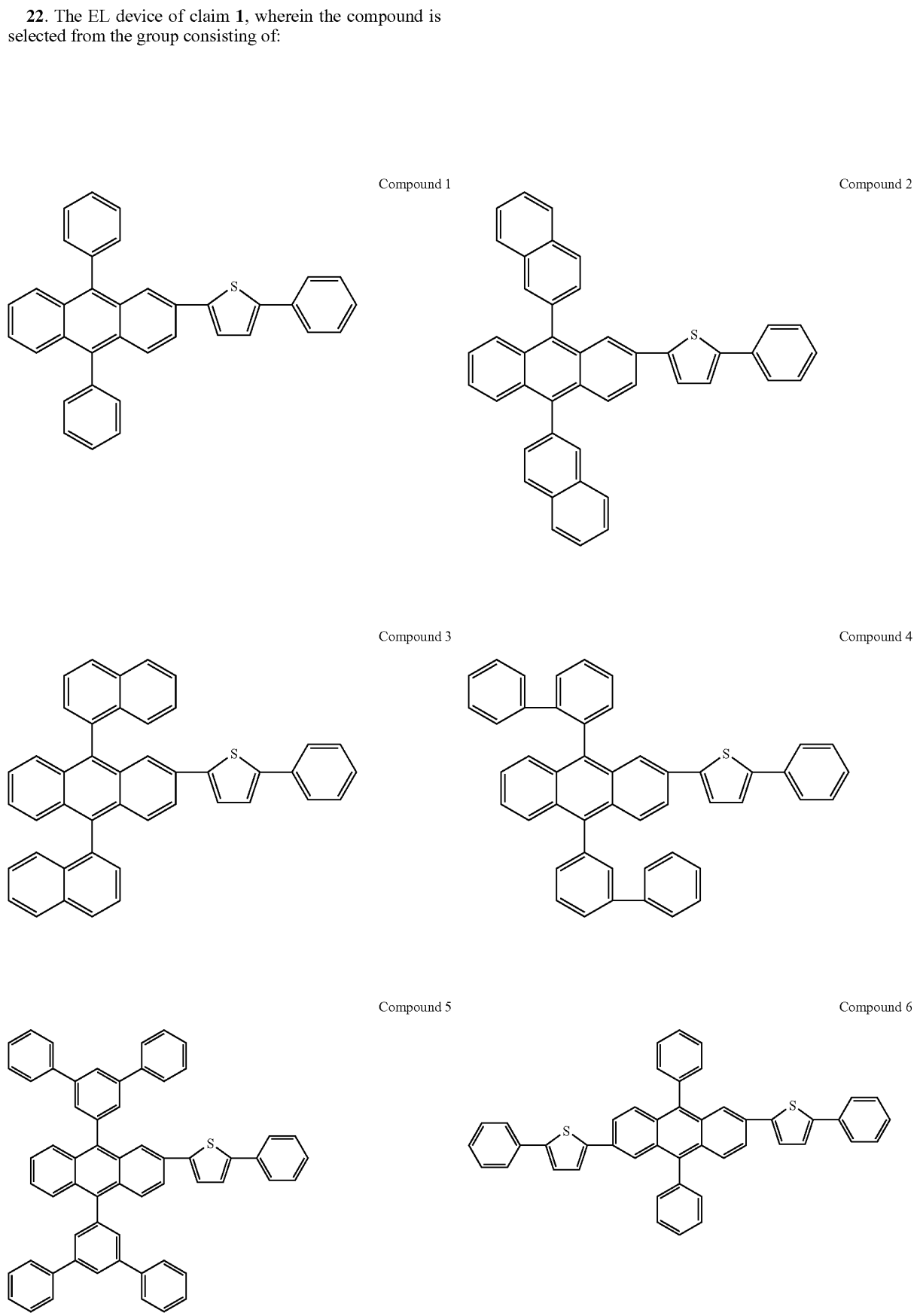

-continued
Compound 7
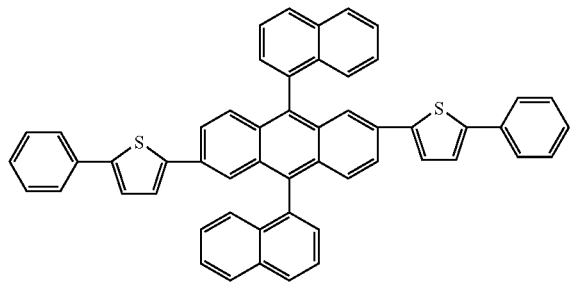
Compound 8
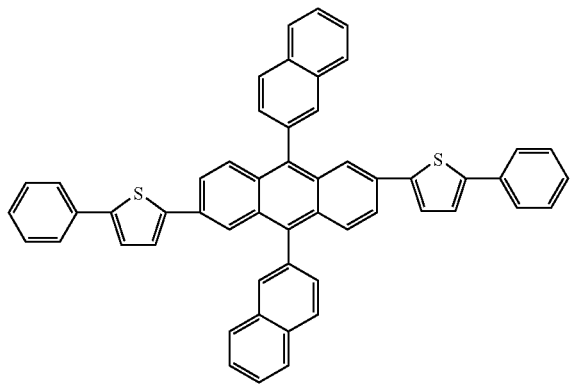
Compound 9
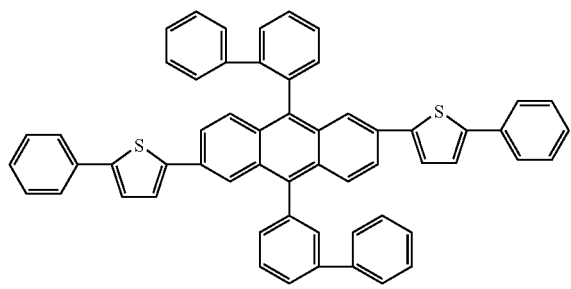
Compound 10
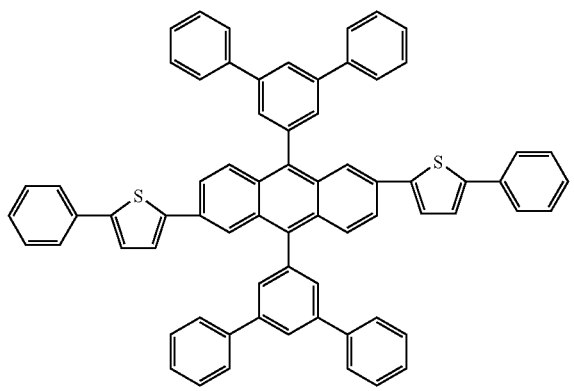
Compound 11
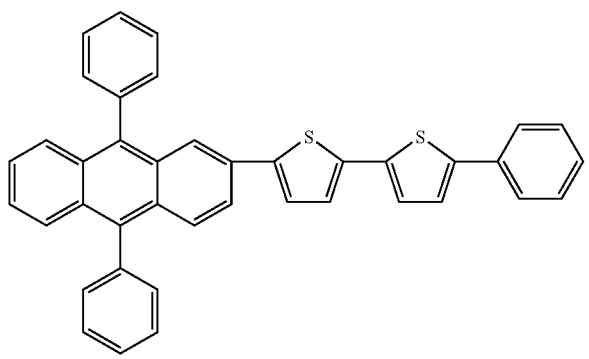
Compound 12
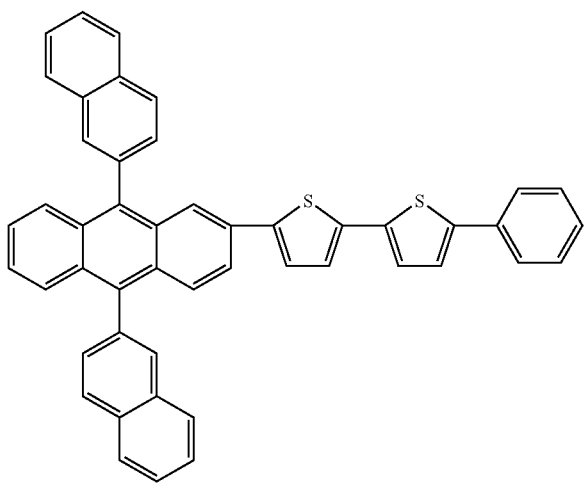

-continued
Compound 13
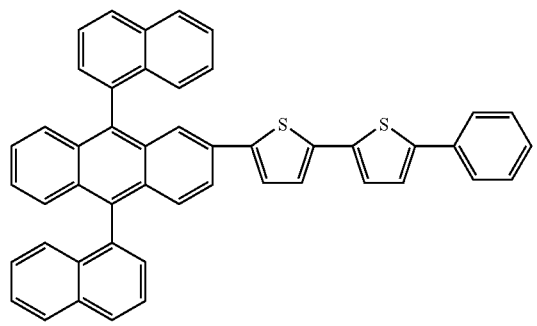
Compound 14
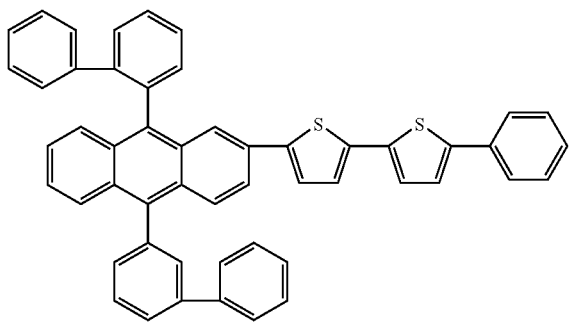
Compound 15
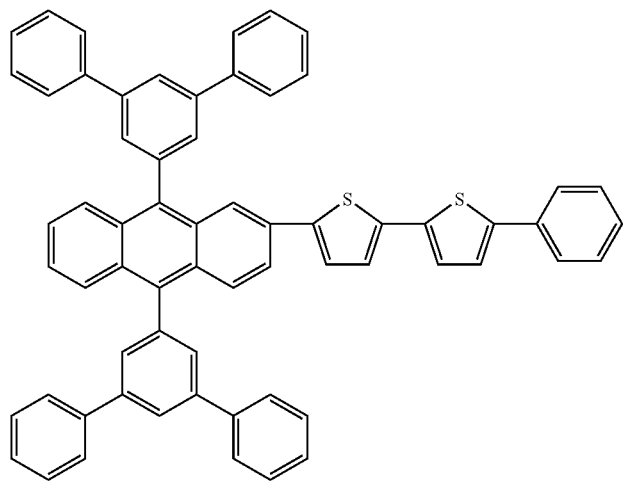
Compound 16
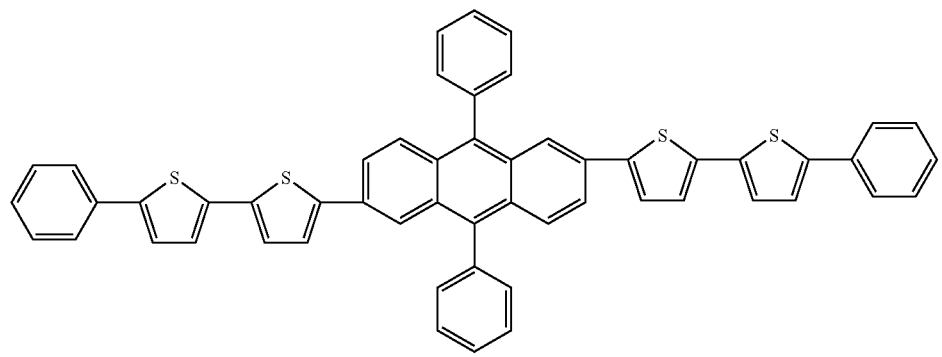
Compound 17
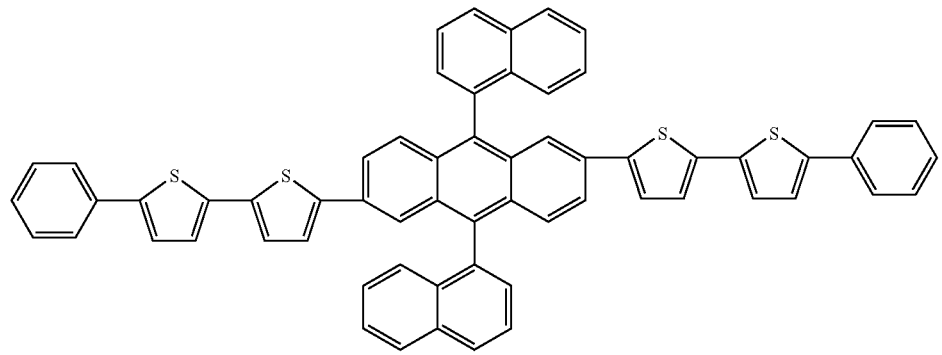

-continued
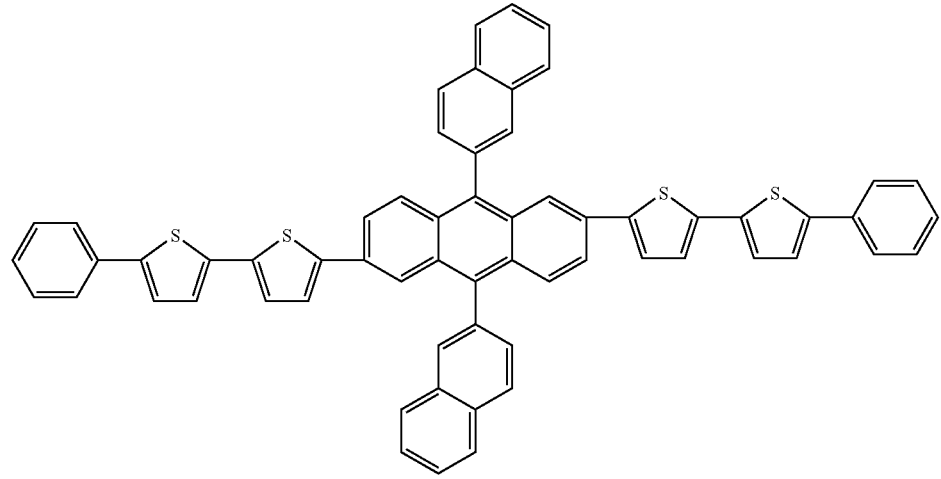
Compound 18
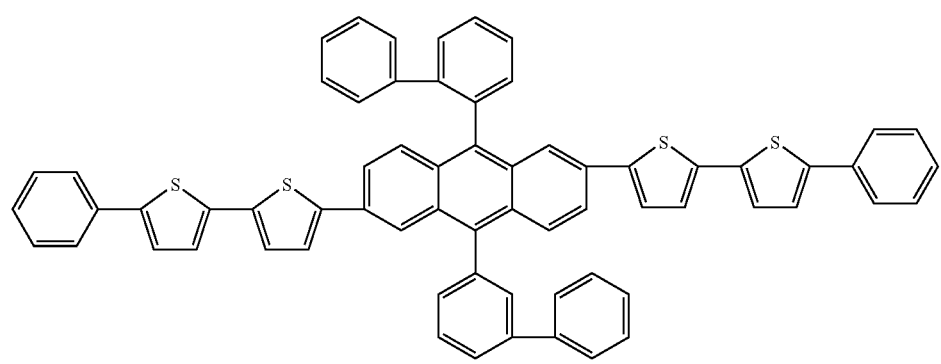
Compound 19
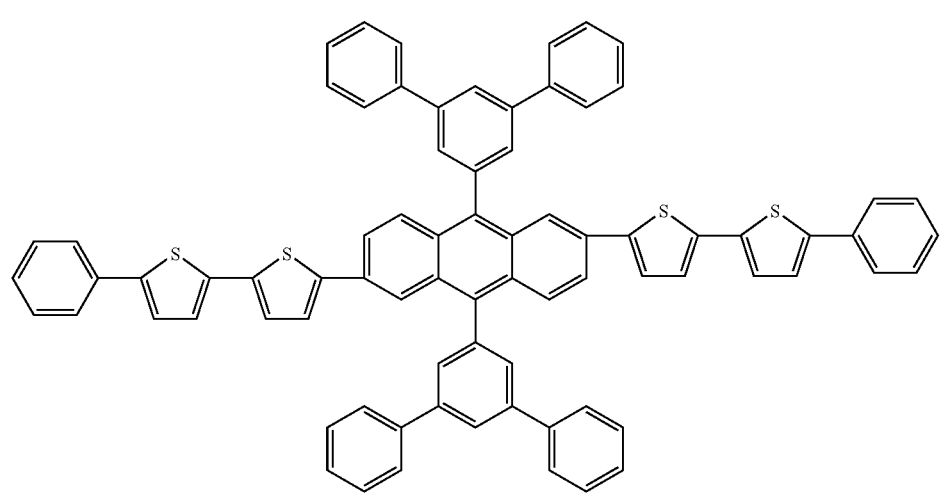
Compound 20

-continued
Compound 21
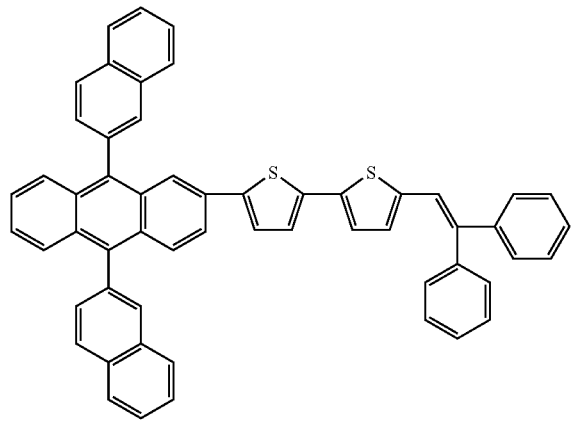
Compound 22
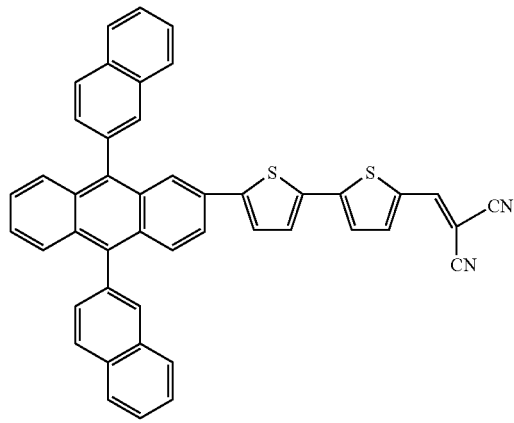
Compound 23
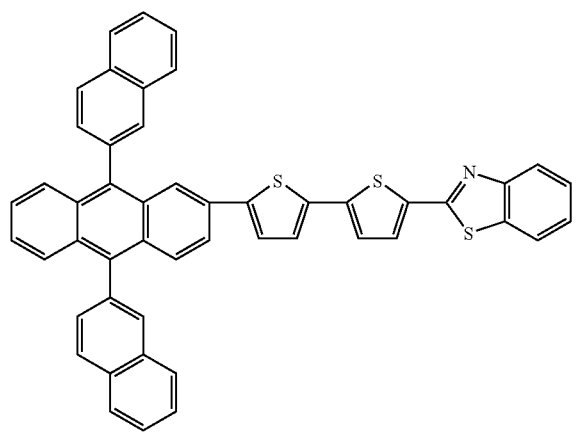
Compound 24
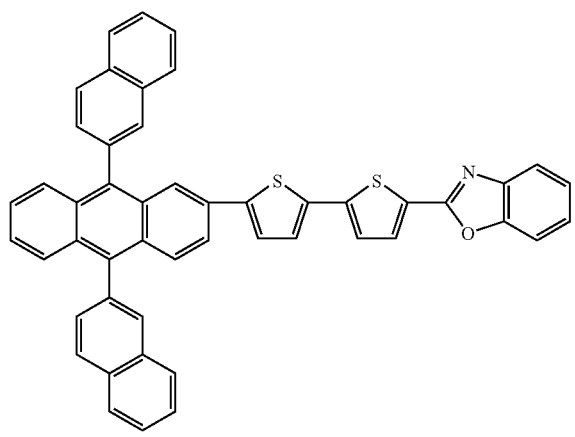
Compound 25
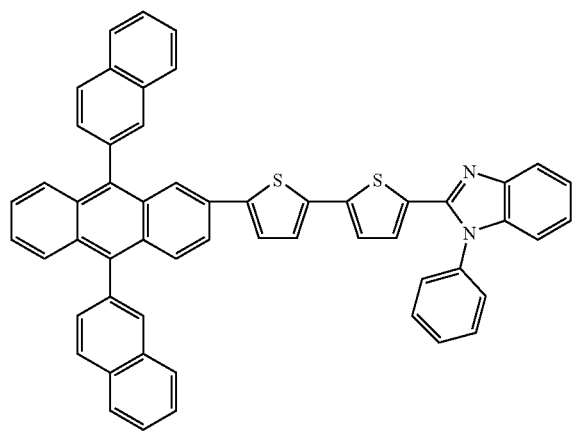
Compound 26
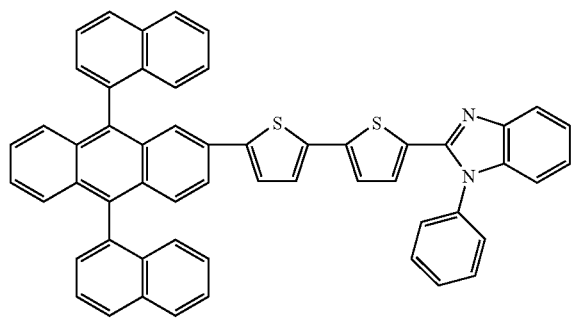

Compound 27
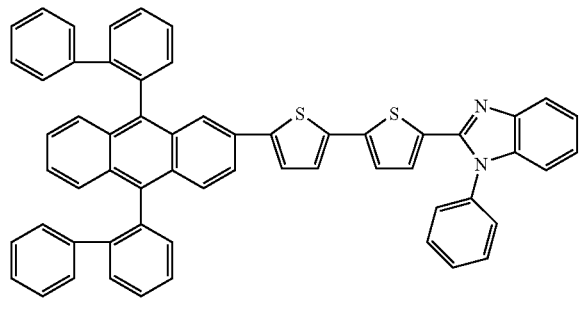
Compound 28
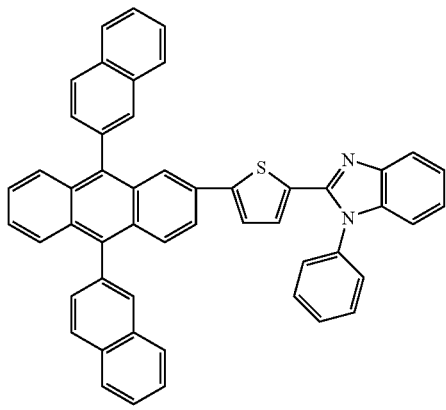
Compound 29
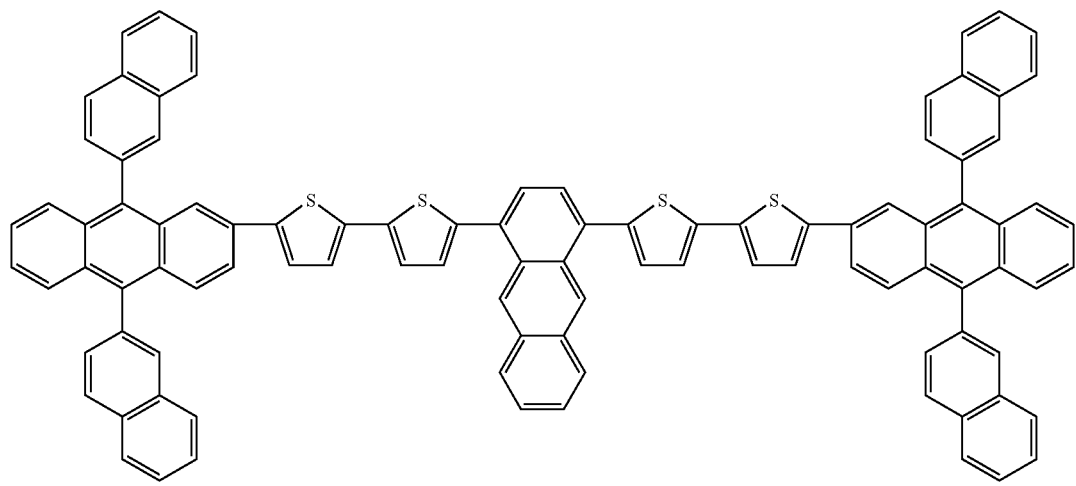
Compound 30
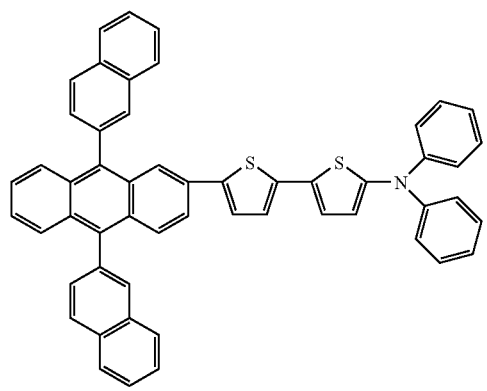
Compound 31
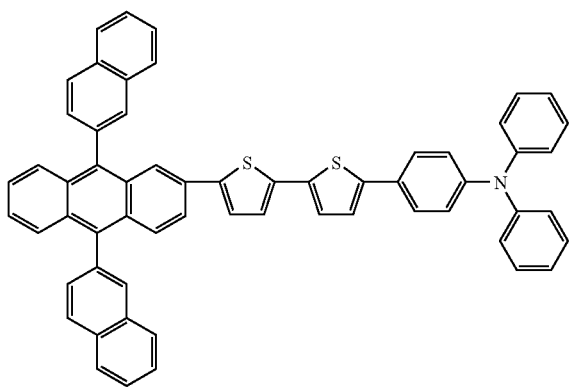

-continued
Compound 32
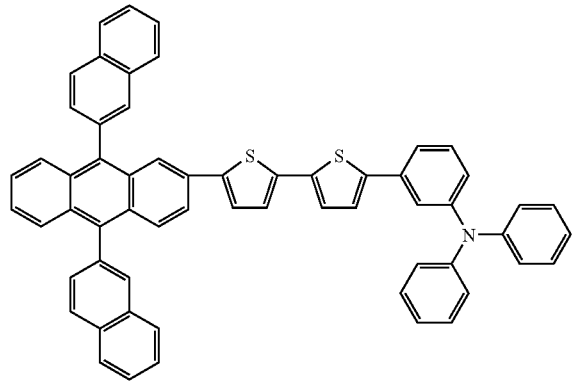
Compound 33
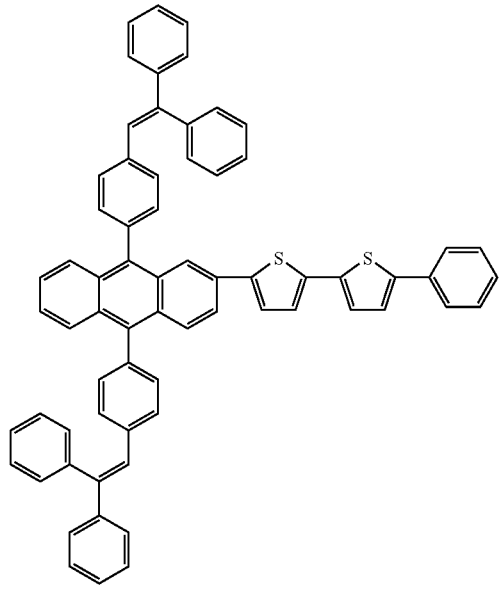
Compound 34
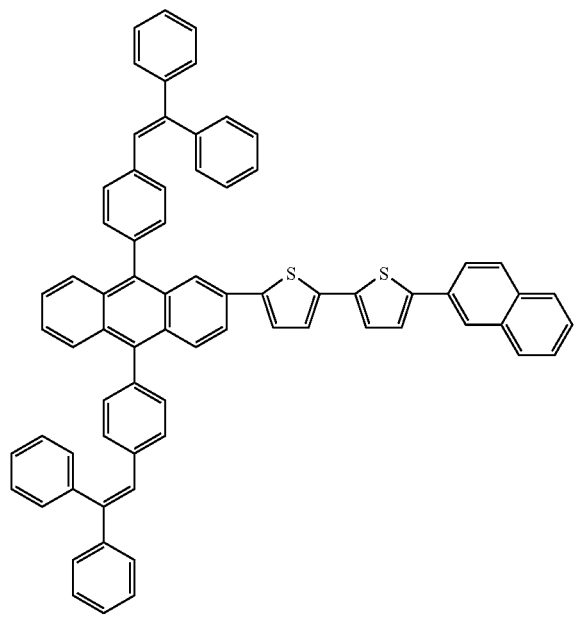
Compound 35
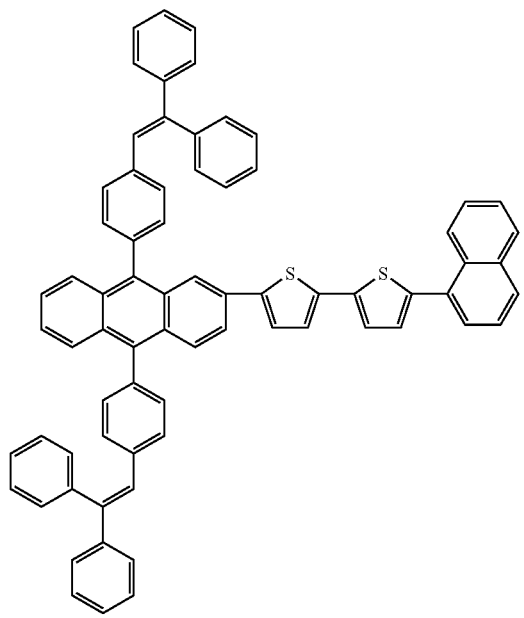
Compound 36
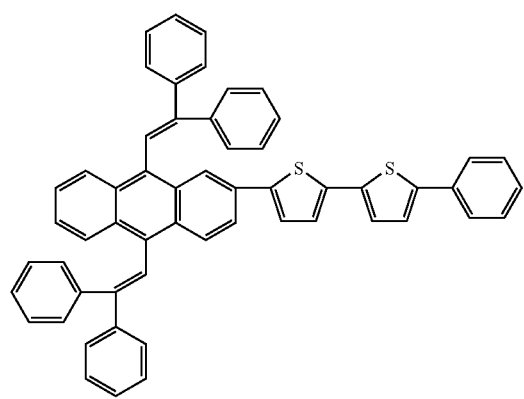
Compound 37
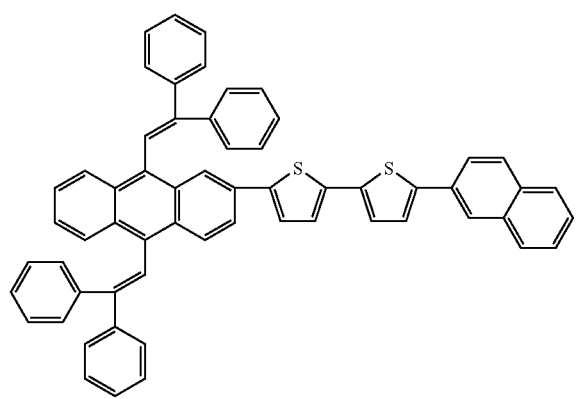

-continued
Compound 38
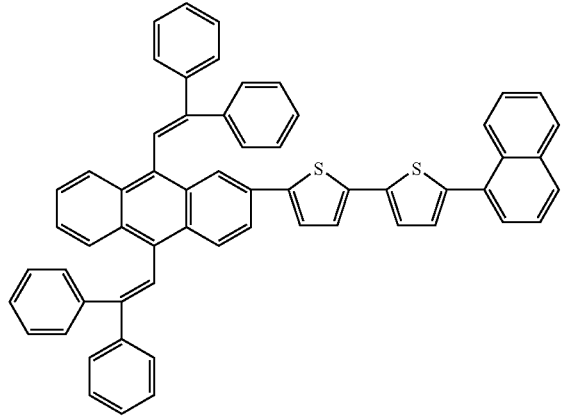
Compound 39
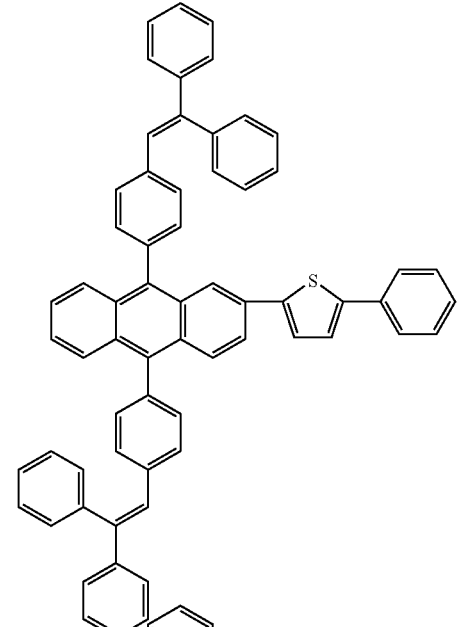
Compound 40
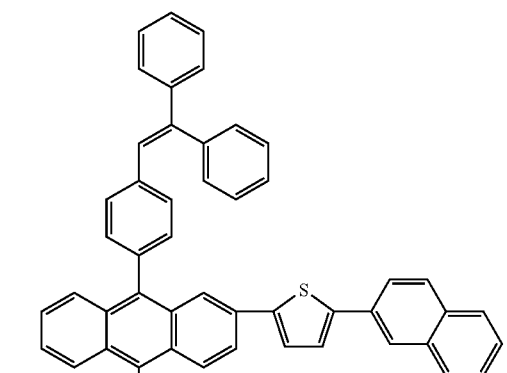
Compound 41
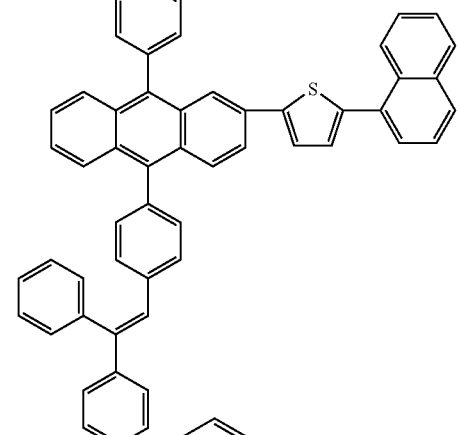
Compound 42
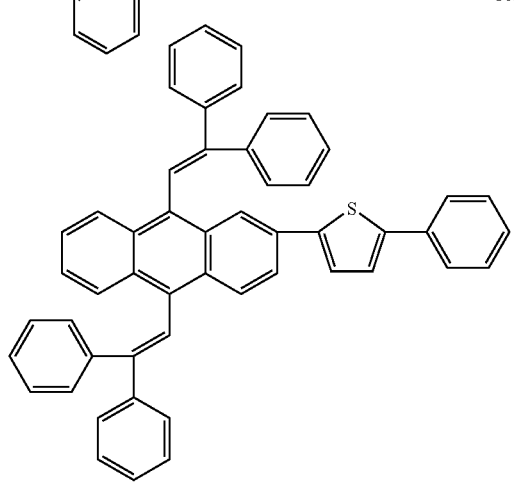
Compound 43
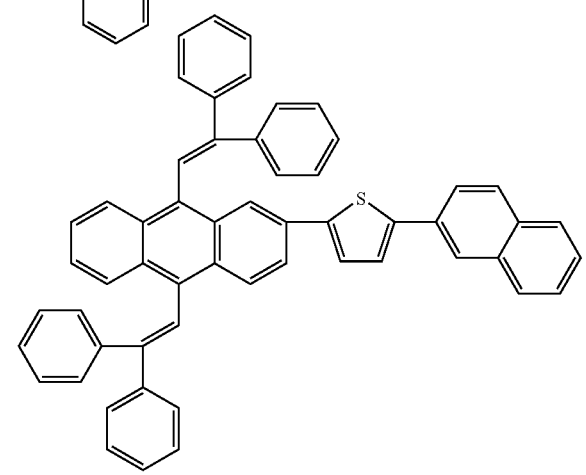

-continued
Compound 44
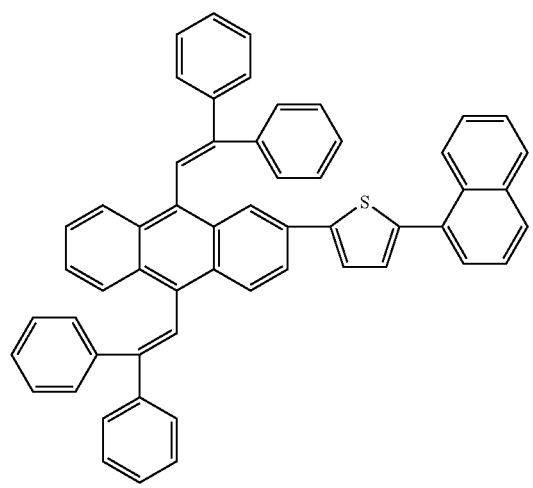
Compound 45
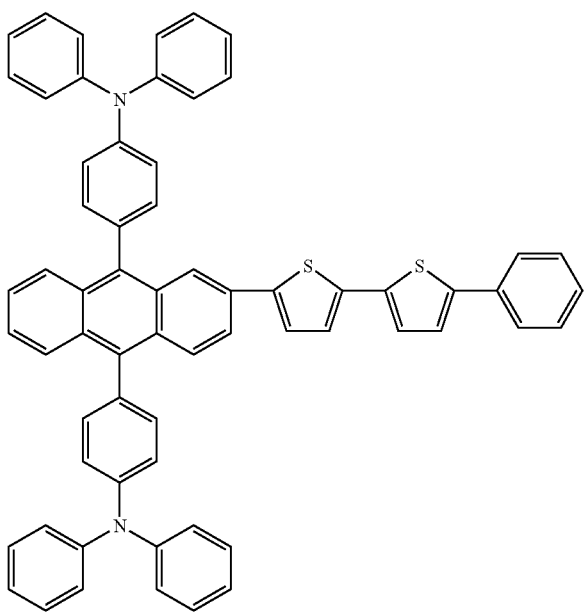
Compound 46
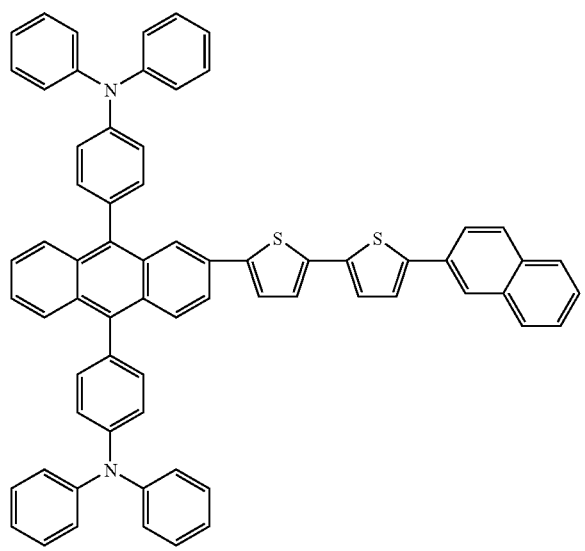
Compound 47
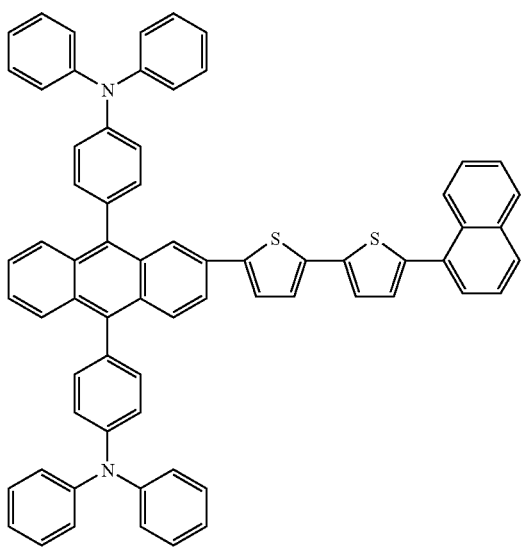
Compound 48
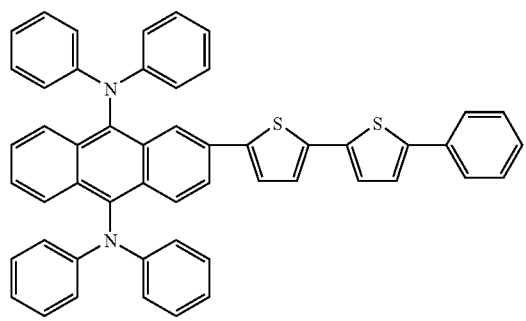
Compound 49
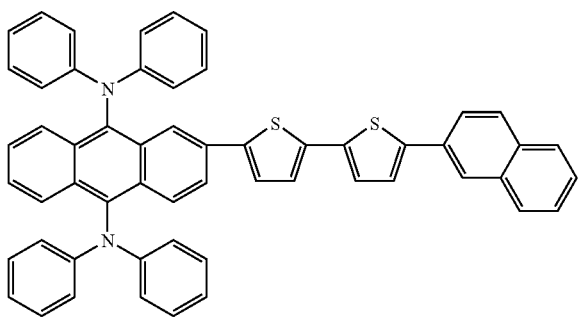

-continued
Compound 50
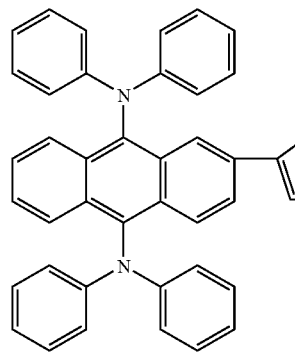
Compound 51
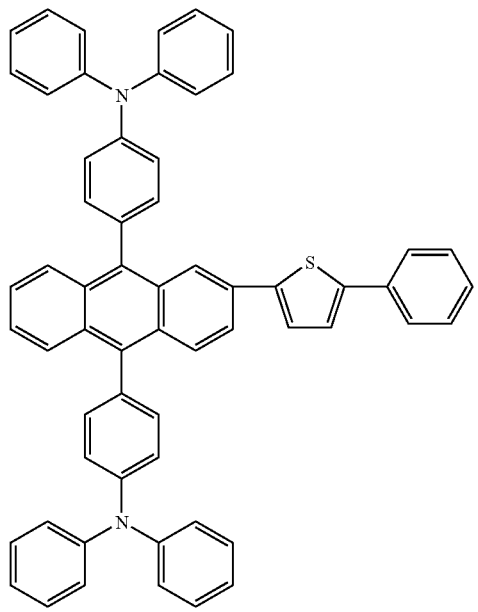
Compound 52
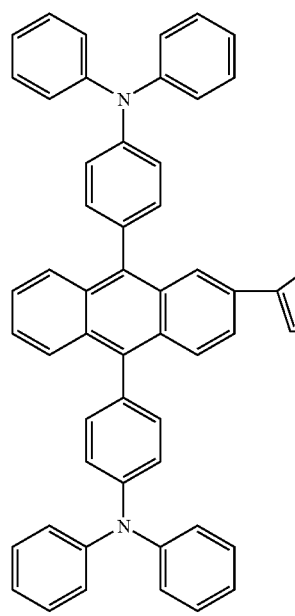
Compound 53
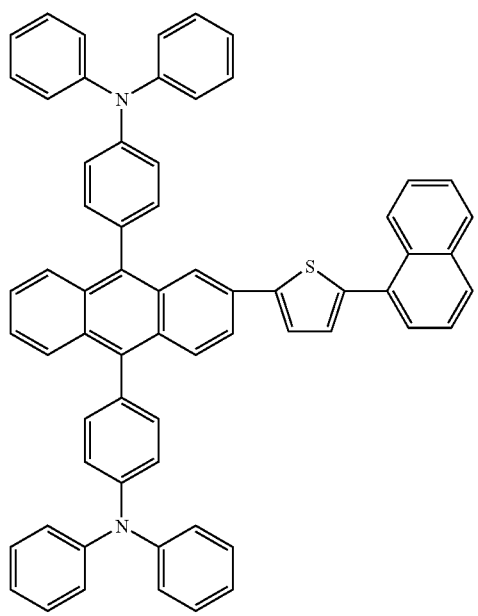
Compound 54
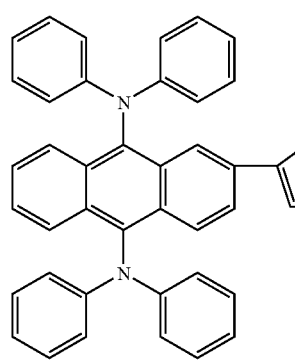
Compound 55
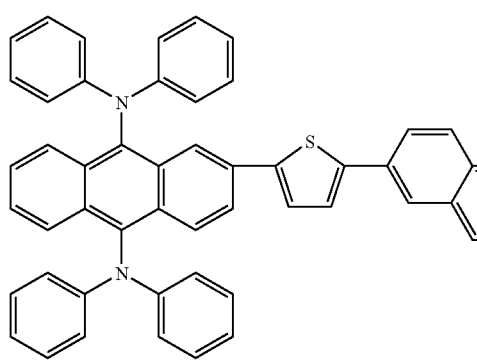

-continued
Compound 56
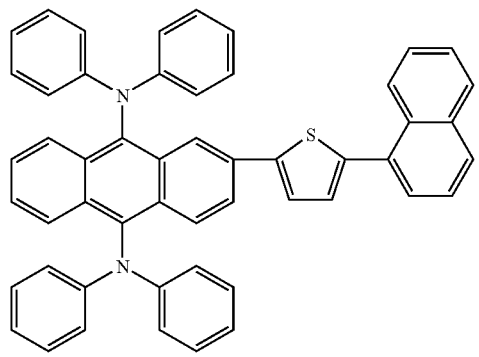
Compound 57
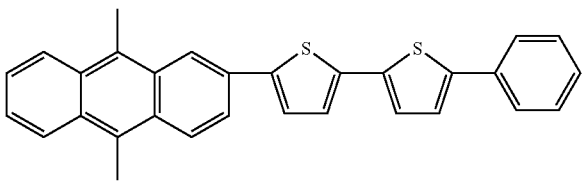
Compound 58
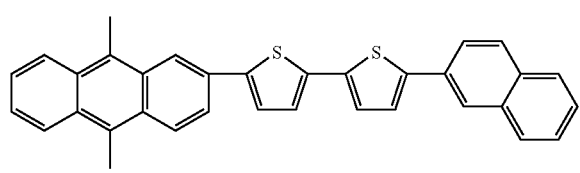
Compound 59
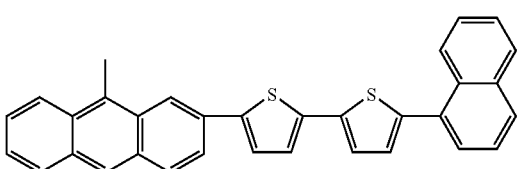
Compound 60
Compound 61
Compound 62
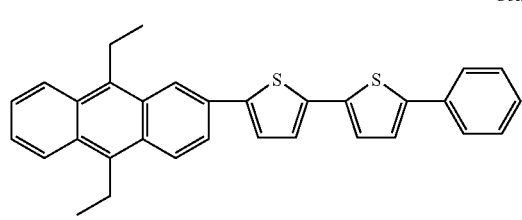
Compound 63
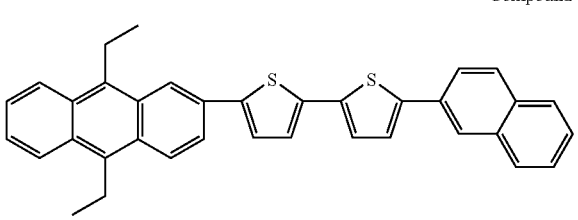
Compound 64
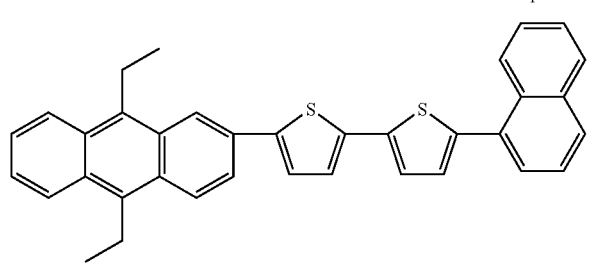
Compound 65
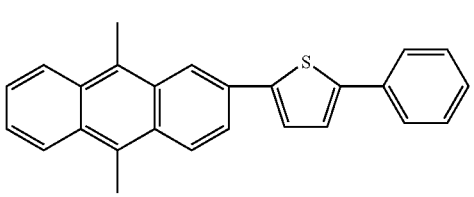
Compound 66
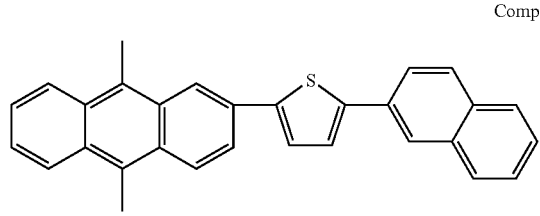
Compound 67
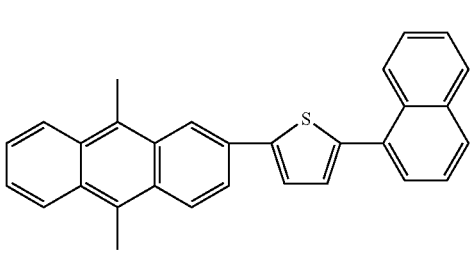
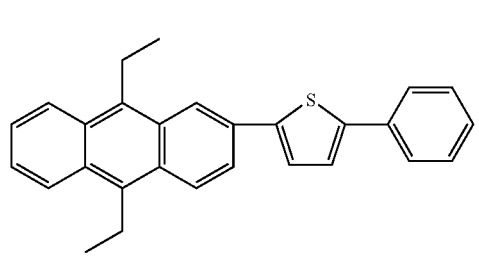
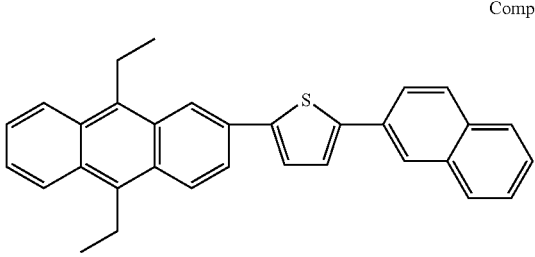

-continued
Compound 68
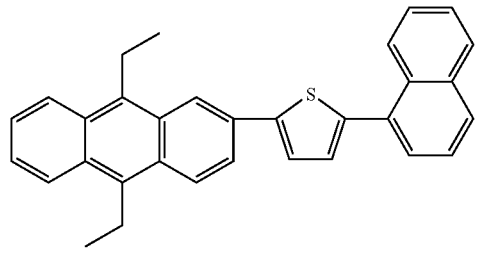
Compound 69
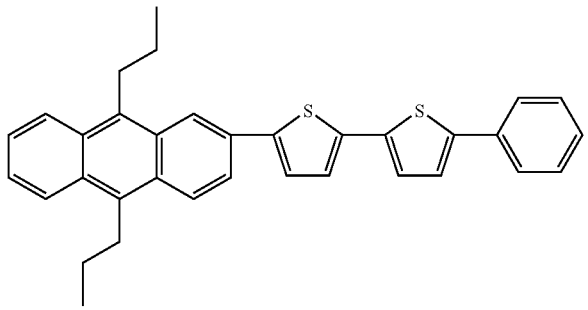
Compound 70
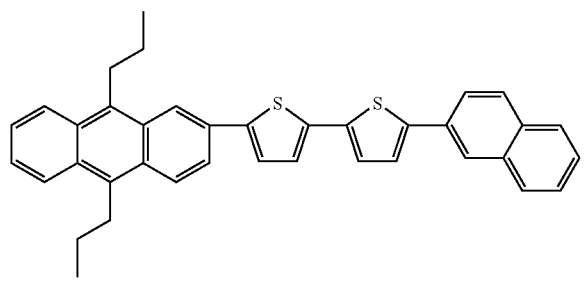
Compound 71
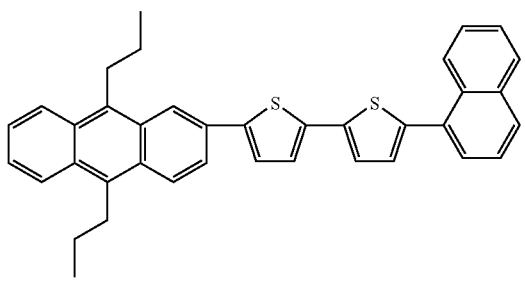
Compound 72
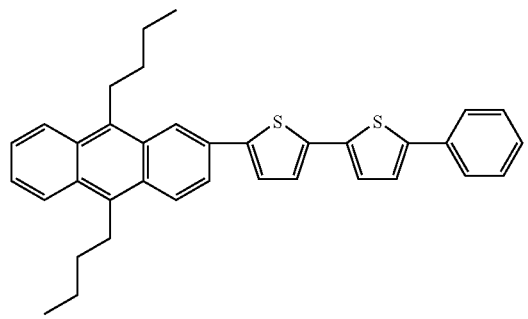
Compound 73
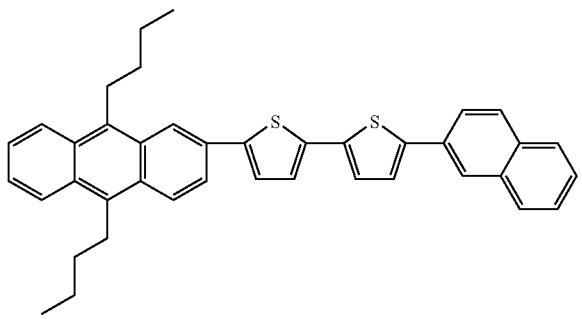
Compound 74
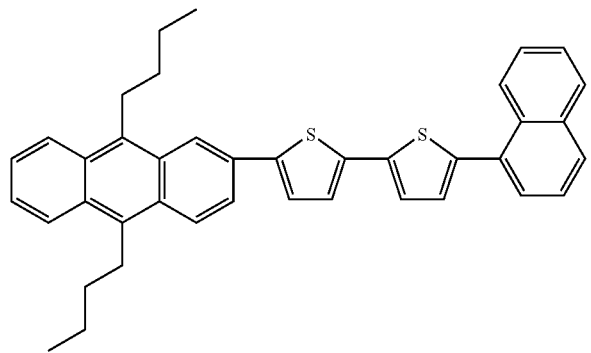
Compound 75
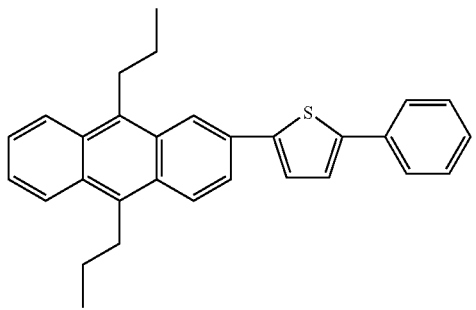

-continued
Compound 76
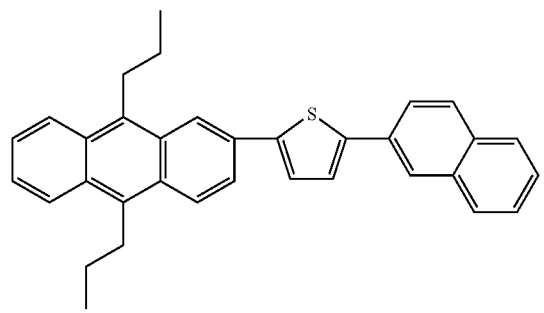
Compound 77
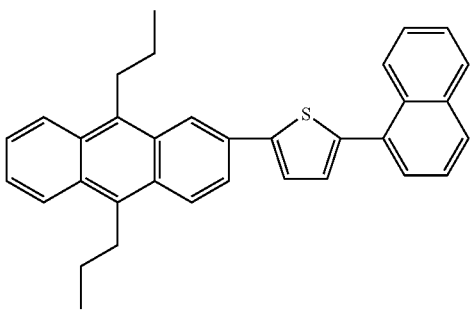
Compound 78
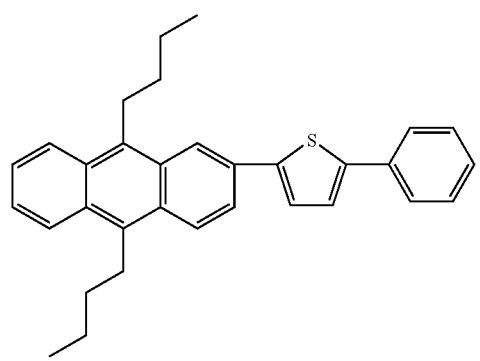
Compound 79
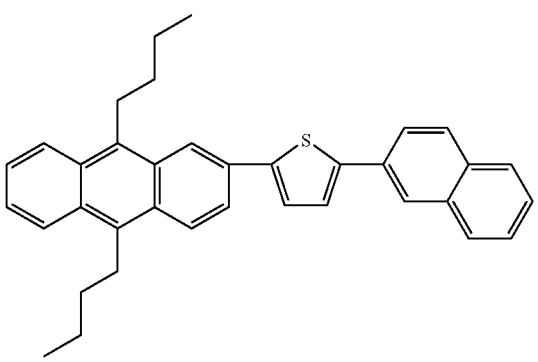
Compound 80
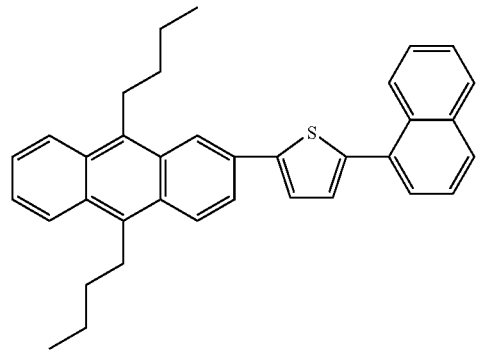
Compound 81
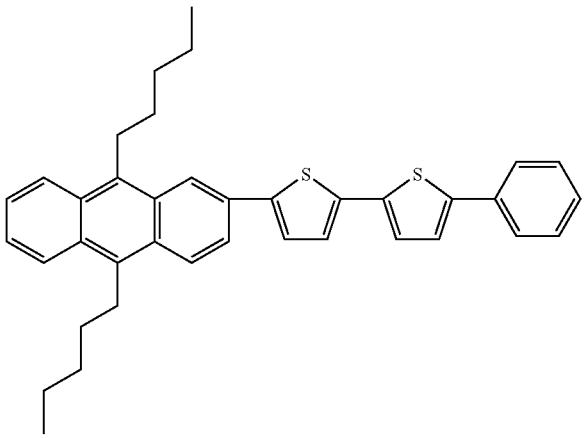
Compound 82
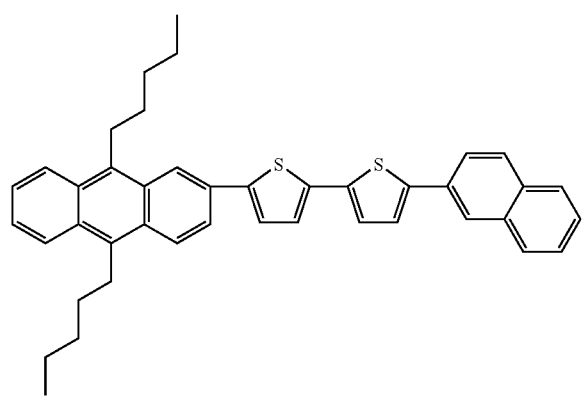
Compound 83
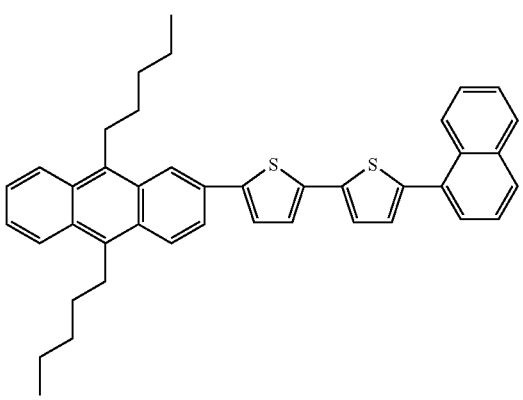

-continued
Compound 84
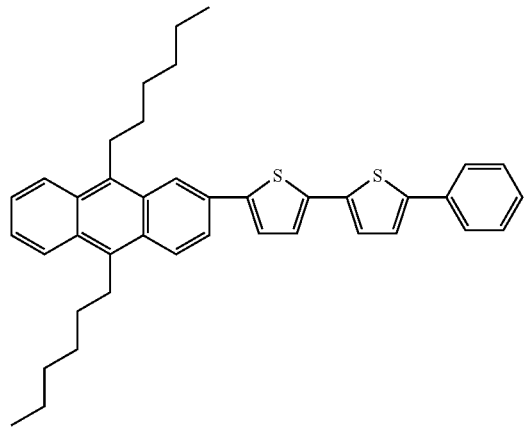
Compound 85
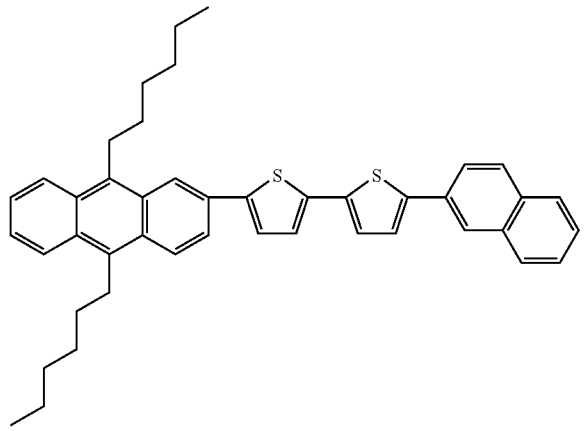
Compound 86
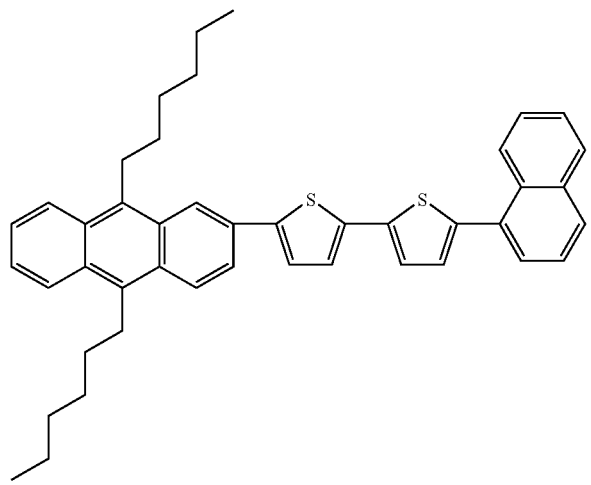
Compound 87
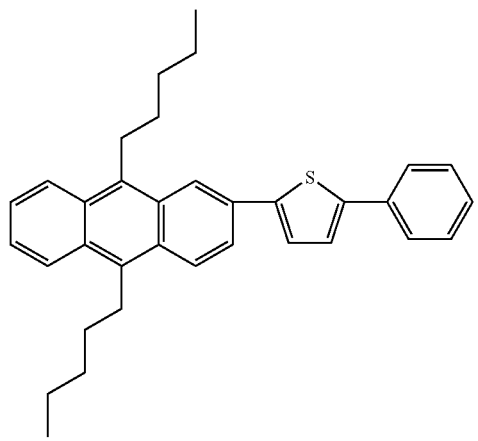
Compound 88
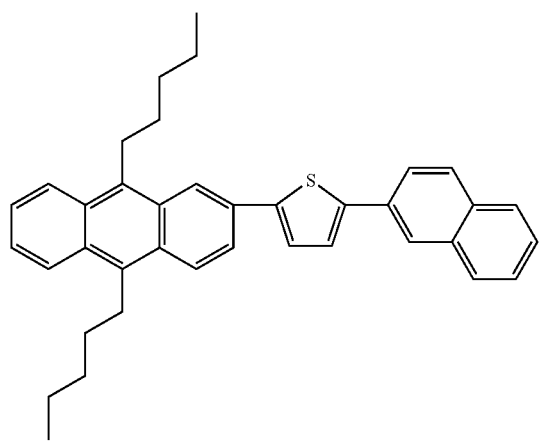
Compound 89
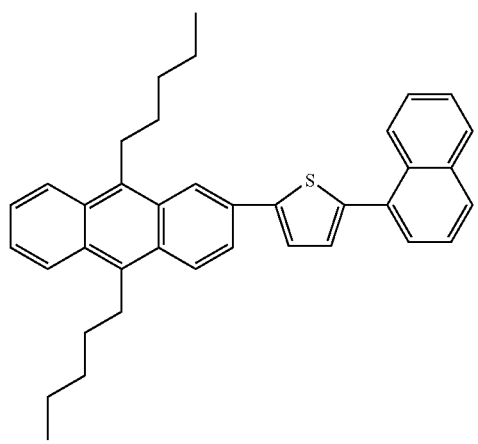

-continued

Compound 90

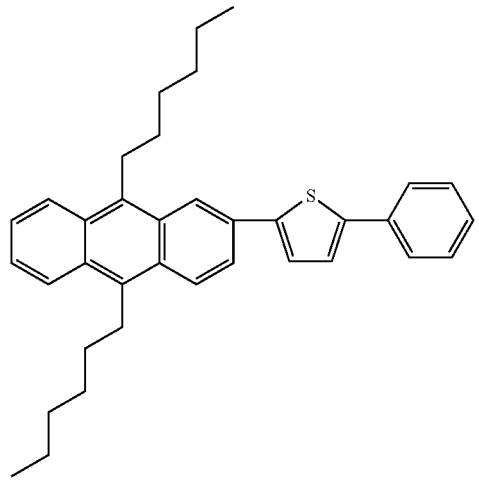

Compound 91

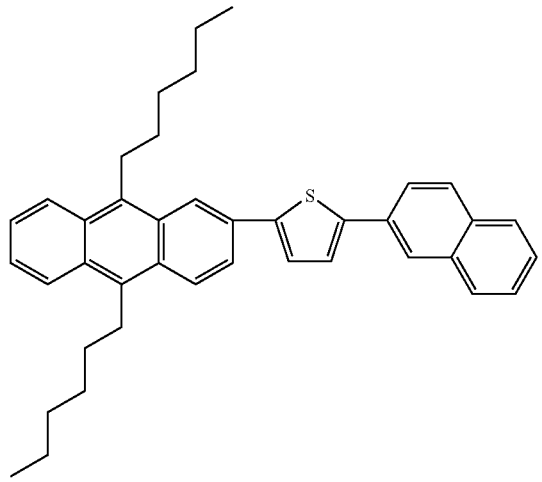

Compound 92

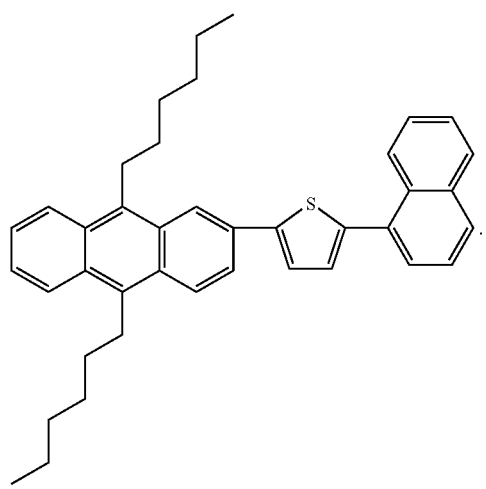

23. The EL device of claim 22, wherein the compound is selected from the group consisting of Compounds 1 through 56.

24. The EL device of claim 22, wherein the compound is selected from the group consisting of Compounds 1 through 32.

25. The EL device of claim 22, wherein the compound is selected from the group consisting of Compounds 1 through 20.

26. The EL device of claim 22, wherein the compound is selected from the group consisting of Compounds 4, 12, 14, 19, 21, 23 and 25.

27. The EL device of claim 22, wherein the compound has a melting point above about 300° C.

28. The EL device of claim 22, wherein the compound has a band-gap corresponding to visible light emission.

29. The EL device of claim 28, wherein the band-gap for the visible light emission is from about 1.8 eV to about 3.5 eV.

30. The organic EL device of claim 1, further comprising at least one additional layer selected from the group consisting of light-emitting layer, hole-injecting layer, hole-transporting layer, electron-transporting layer and electron-injecting layer which are located between the anode and cathode.

31. The organic EL device of claim 1, wherein the organic EL device is supported by a substrate, and wherein the substrate contacts either the anode or the cathode.

32. The organic EL device of claim 1, wherein the light-emitting layer further comprises one or more fluorescent or phosphorescent light-emitting materials.

33. The organic EL device of claim 30, wherein the hole-injecting layer and the hole-transporting layer are located between the anode and the light-emitting layer.

34. The organic EL device of claim 30, wherein the electron-injecting layer and the electron-transporting layer are located between the cathode and the light-emitting layer.

35. The organic EL device of claim 1, wherein the light-emitting layer comprises at least two compounds capable of emitting light therein.

36. The organic EL device of claim 1, wherein the light-emitting layer further comprises at least one additional light-emitting compound, which is represented by Formula I or not.

37. The organic EL device of claim 36, wherein the additional light-emitting compound has a quantum efficiency equal or higher than that of the at least one compound represented by Formula I.

38. The organic EL device of claim 36, wherein the additional light-emitting compound has a band gap equal or smaller than that of the at least one compound represented by Formula I.

39. The organic EL device of claim 36, wherein the band gap of the additional compound is from about 70% up to 100% of the band gap of the compound represented by Formula I.

40. The organic EL device of claim 36, wherein the band gap of the additional compound is from about 80% up to 100% of the band gap of the compound represented by Formula I.

41. The organic EL device of claim 36, wherein the band gap of the additional compound is from about 90% up to 100% of the band gap of the compound represented by Formula I.

42. The organic EL device of claim 36, wherein the additional light-emitting compound is a phosphorescent light-emitting compound, which is not represented by Formula I.

43. The organic EL device of claim 36, wherein the additional light-emitting compound is selected from the group consisting of BCzVBi, perylene, rubrene, DCJTB, quinacridone, coumarine, nile red, DCM1, DCM2, tetradiphenylamino pyrimido-pyrimidine, pyrydinothiadiazole and Compounds 201-220:

Compound 201

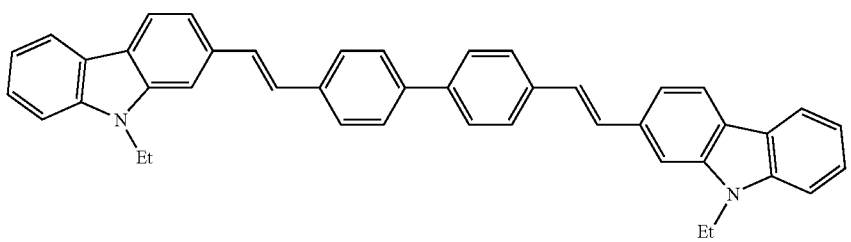

Compound 202

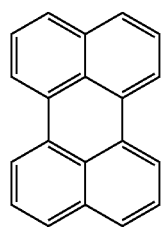

Compound 203

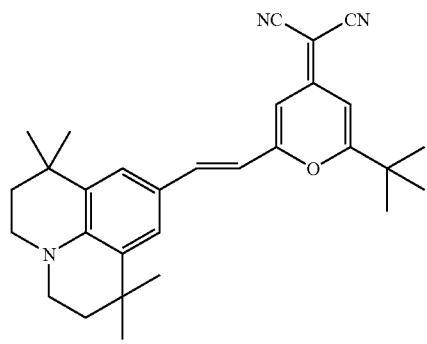

Compound 204

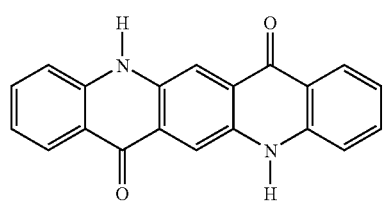

Compound 205

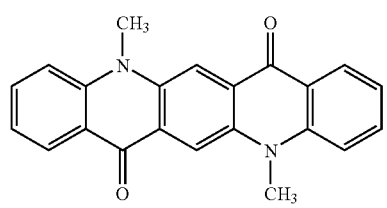

Compound 206

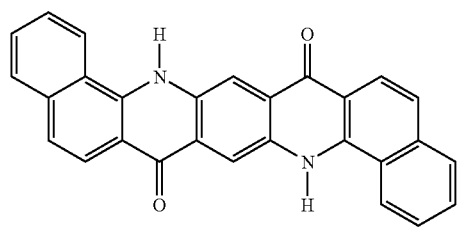

Compound 207

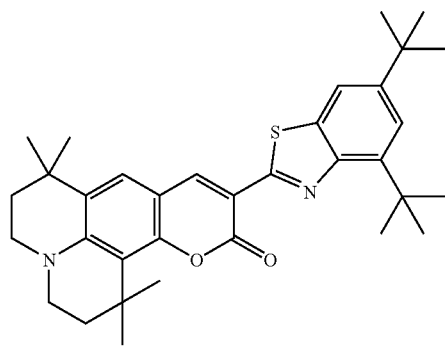

-continued
Compound 208
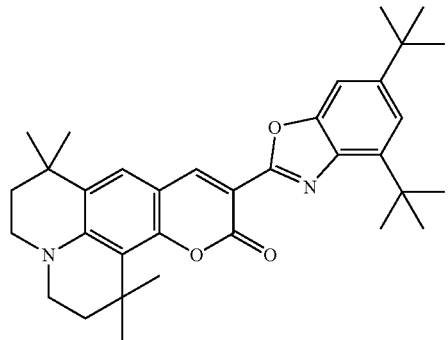
Compound 209
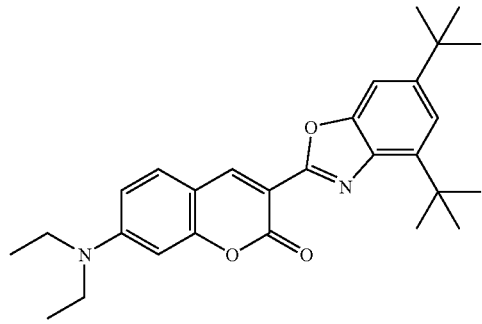
Compound 210
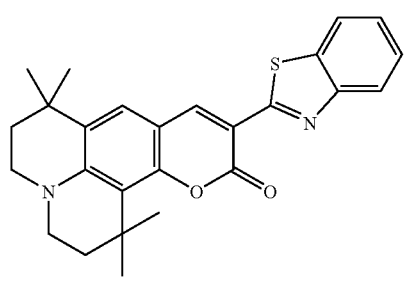
Compound 211
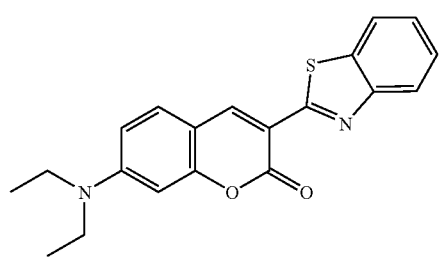
Compound 212
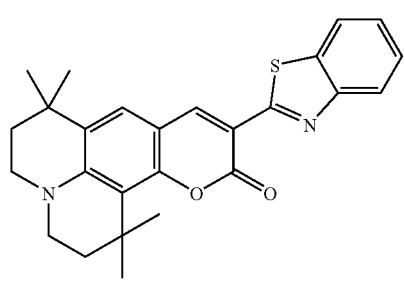
Compound 213
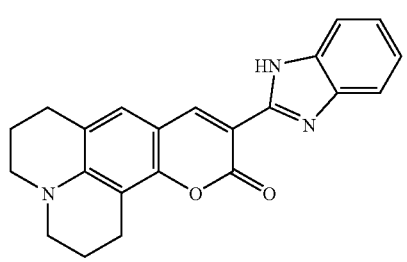
Compound 214
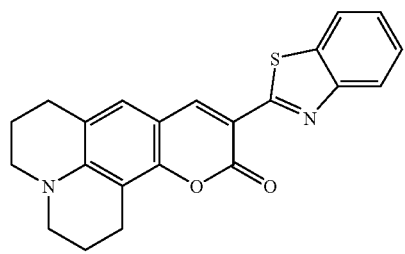
Compound 215
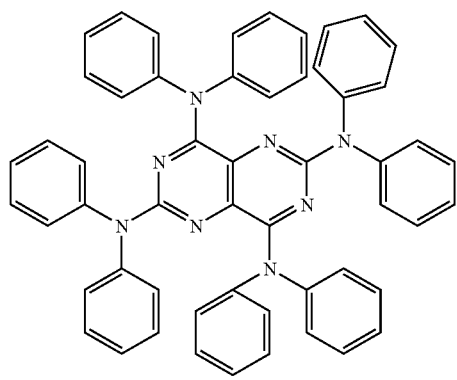

Compound 216
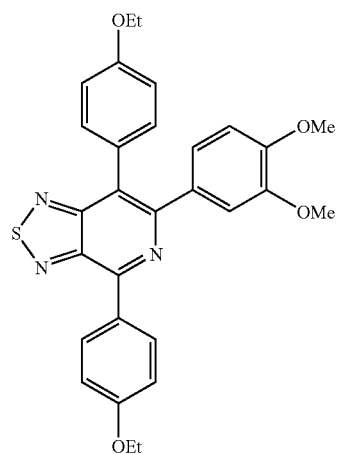
Compound 217
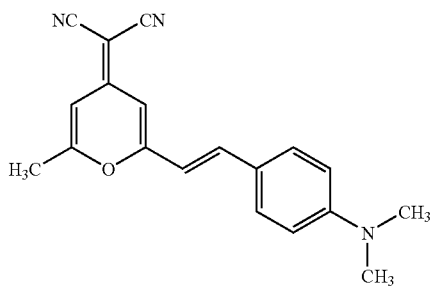
Compound 218
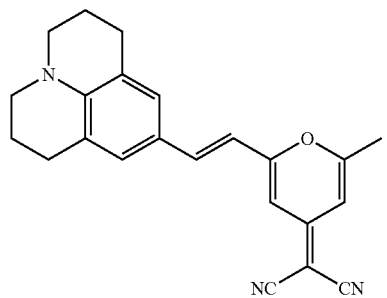
Compound 219
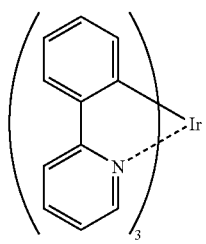
Compound 220
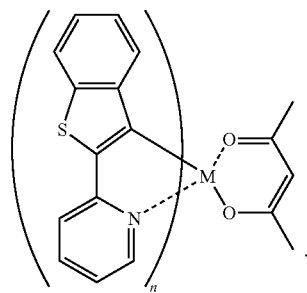
44. An electronic apparatus comprising a display having the organic EL device of claim 1.
* * * * *